US010292596B2

(12) United States Patent
Shadforth et al.

(10) Patent No.: US 10,292,596 B2
(45) Date of Patent: May 21, 2019

(54) METHOD AND SYSTEM FOR VISUALIZATION OF HEART TISSUE AT RISK

(71) Applicant: Analytics For Life, Ganaoque (CA)

(72) Inventors: Ian Shadforth, Morrisville, NC (US); Meng Lei, North York (CA); Timothy Burton, Ottawa (CA); Don Crawford, Fernandina Beach, FL (US); Sunny Gupta, Amherstview (CA); Paul Douglas Souza, Novato, CA (US); Cody James Wackerman, Chico, CA (US); Andrew Hugh Dubberly, Palo Alto, CA (US)

(73) Assignee: Analytics For Life Inc., Toronto (CA)

( * ) Notice: Subject to any disclaimer, the term of this patent is extended or adjusted under 35 U.S.C. 154(b) by 42 days.

(21) Appl. No.: 15/712,104

(22) Filed: Sep. 21, 2017

(65) Prior Publication Data

US 2018/0078146 A1 Mar. 22, 2018

Related U.S. Application Data

(60) Provisional application No. 62/397,895, filed on Sep. 21, 2016.

(51) Int. Cl.
*G06K 9/00* (2006.01)
*A61B 5/01* (2006.01)
(Continued)

(52) U.S. Cl.
CPC ............ *A61B 5/015* (2013.01); *A61B 5/0033* (2013.01); *A61B 5/02007* (2013.01);
(Continued)

(58) Field of Classification Search
CPC ..................................................... G16H 50/20
See application file for complete search history.

(56) References Cited

U.S. PATENT DOCUMENTS

| 5,954,660 A | 9/1999 | Legay et al. |
| 8,790,255 B2 * | 7/2014 | Behar .................. A61B 5/0002 600/300 |

(Continued)

FOREIGN PATENT DOCUMENTS

| WO | 2012021307 | 2/2012 |
| WO | 2012139116 | 10/2012 |

OTHER PUBLICATIONS

Wavelet Based ECG Denoising Using Signal-Noise Residue Method, Khan et al., May 2011, 5th International Conference on Bioinformatics and Biomedical Engineering (abstract, section III, Figure 1).

(Continued)

*Primary Examiner* — Oneal R Mistry
(74) *Attorney, Agent, or Firm* — Meunier Carlin & Curfman LLC

(57) ABSTRACT

Exemplified methods and systems facilitate presentation of data derived from measurements of the heart in a non-invasive procedure (e.g., via phase space tomography analysis). In particular, the exemplified methods and systems facilitate presentation of such measurements in a graphical user interface, or "GUI" (e.g., associated with a healthcare provider web portal to be used by physicians, researchers, or patients, and etc.) and/or in a report for diagnosis of heart pathologies and disease. The presentation facilitates a unified and intuitive visualization that includes three-dimensional visualizations and two-dimensional visualizations that are concurrently presented within a single interactive interface and/or report.

22 Claims, 41 Drawing Sheets

(51) Int. Cl.
| | |
|---|---|
| A61B 5/00 | (2006.01) |
| A61B 5/02 | (2006.01) |
| A61B 6/00 | (2006.01) |
| G16H 50/20 | (2018.01) |
| G16H 30/00 | (2018.01) |
| G06T 19/20 | (2011.01) |
| A61B 6/03 | (2006.01) |
| A61B 5/053 | (2006.01) |
| A61B 17/00 | (2006.01) |
| A61B 5/026 | (2006.01) |

(52) U.S. Cl.
CPC ............ *A61B 5/743* (2013.01); *A61B 5/7425* (2013.01); *A61B 6/032* (2013.01); *A61B 6/503* (2013.01); *G06T 19/20* (2013.01); *G16H 30/00* (2018.01); *G16H 50/20* (2018.01); *A61B 5/026* (2013.01); *A61B 5/0536* (2013.01); *A61B 5/748* (2013.01); *A61B 5/7435* (2013.01); *A61B 2017/00243* (2013.01); *A61B 2576/023* (2013.01); *G06T 2210/41* (2013.01); *G06T 2219/028* (2013.01); *G06T 2219/2012* (2013.01)

(56) References Cited

U.S. PATENT DOCUMENTS

| | | |
|---|---|---|
| 2013/0303871 A1 | 11/2013 | Brest Van Kempen et al. |
| 2014/0023255 A1 | 1/2014 | Lim et al. |
| 2014/0194758 A1 | 7/2014 | Korenberg et al. |
| 2015/0342537 A1 | 12/2015 | Taylor et al. |
| 2016/0140707 A1* | 5/2016 | Abe ........................ G06T 15/00 382/131 |
| 2016/0249885 A1* | 9/2016 | Schneider ............ A61B 8/0883 382/131 |
| 2018/0060524 A1* | 3/2018 | Krimsky ................. G06F 19/00 |

OTHER PUBLICATIONS

Cardiac Arrhythmia Recognition with Robust Discrete Wavelet-Based and Geometrical Feature Extraction via Classifiers of SVM and MLP-BP and PNN Neural Networks, Asadi et al., 2015, Computing in Cardiology, issue 43, pp. 933-936 (abstract, Figure 1).

A machine-learning approach for computation of fractional flow reserve from coronary computed tomography, Itu et al., Apr. 14, 2016 (Apr. 14, 2016), Journal of Applied Physiology, 121(1), pp. 42-52.

International Search Report, dated Oct. 24, 2017, received in connection with International Patent Application No. PCT/IB2017/053814.

International Search Report and Written Opinion dated Jan. 15, 2018, received in connection with International Patent Application No. PCT/IB2017/055748, 11 pages.

International Search Report and Written Opinion dated Feb. 27, 2018, from International Application No. PCT/IB2016/055125, 8 pages.

Non-Final Office Action dated Jul. 9, 2018, issued in related U.S. Appl. No. 15/633,330, 13 pages.

* cited by examiner

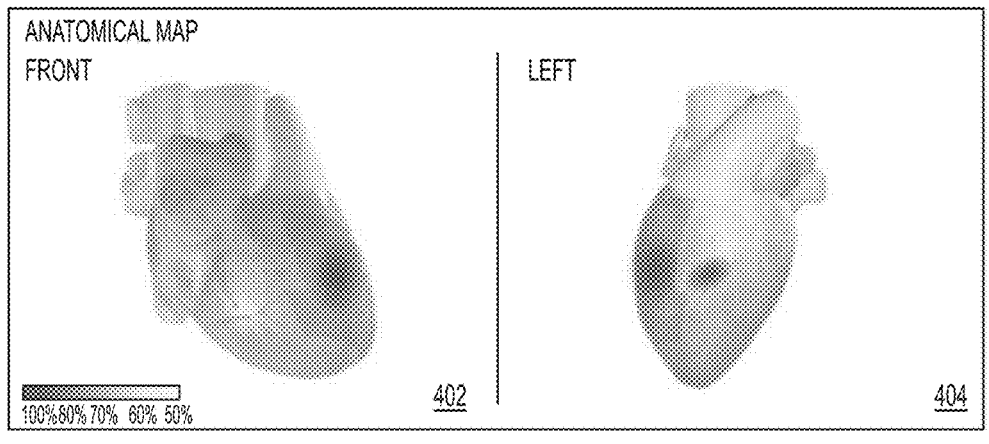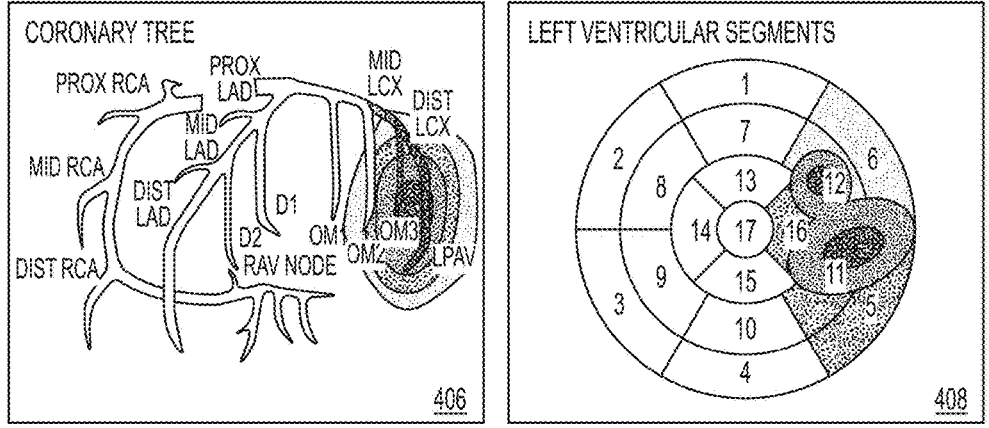
FIG. 4A

400 →

CARDIOANALYSIS REPORT          PATIENT:       JAKE S
                                RECORDING ID:  29449
DOCTOR: DR. RIC                 DATE:          MAR 29, 2016

415 — SIGNIFICANT CORONARY ARTERY DISEASE DETECTED

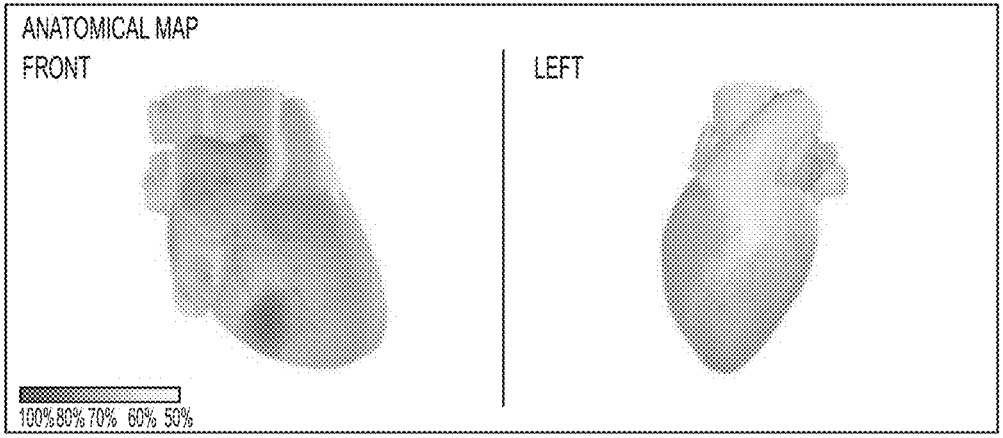

ANATOMICAL MAP
FRONT                                          LEFT

100% 80% 70% 60% 50%

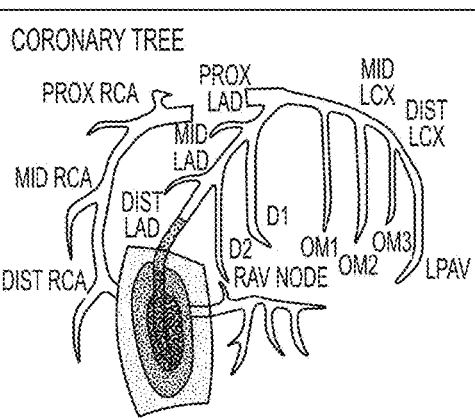

CORONARY TREE

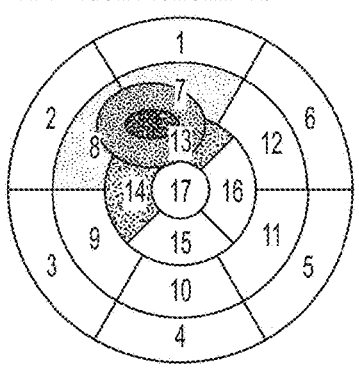

LEFT VENTRICULAR SEGMENTS

417 {
FINDINGS
ONE OF THE MAJOR ARTERIES HAS BLOCKAGE
GREATER THAN 70%.
15% OF MYOCARDIUM AT RISK:

NOTE:
A NORMAL HEART HAS LESS THAN 40% BLOCKAGE IN ANY OF THE
MAJOR ARTERIES WITH NO MYOCARDIUM AT RISK.
FINDINGS HAVE A 95% DEGREE OF ACCURACY AND SHOULD BE
CONFIRMED WITH ADDITIONAL TESTS

SEGMENT 7 - MID ANTERIOR        SEGMENT 14 - APICAL SEPTAL
SEGMENT 8 - MID ANTEROSEPTAL
SEGMENT 13 - APICAL ANTERIOR

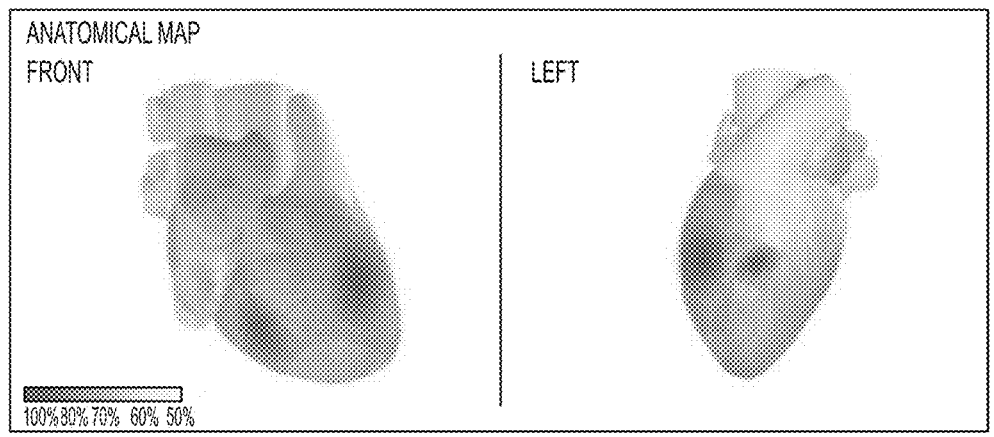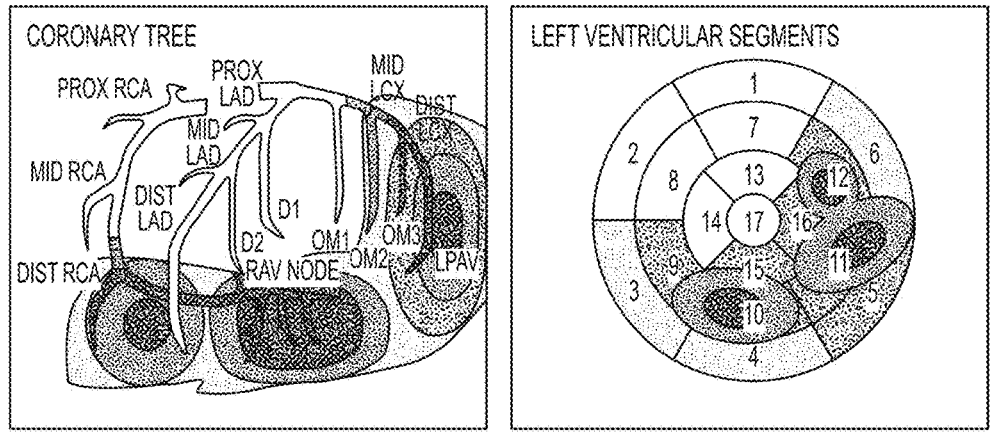
FIG. 4C

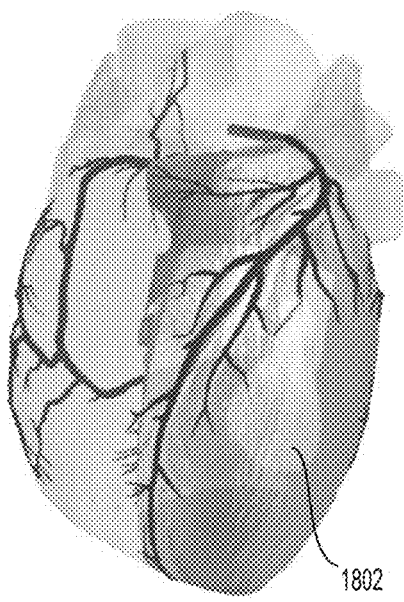 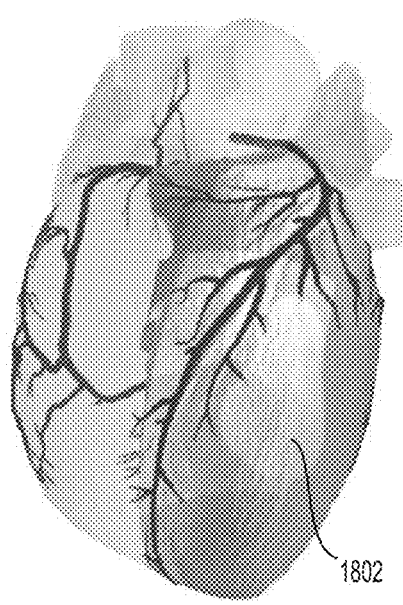
*FIG. 18A*    *FIG. 18B*

METHOD AND SYSTEM FOR VISUALIZATION OF HEART TISSUE AT RISK

CROSS-REFERENCE TO RELATED APPLICATION

This application claims priority to, and the benefit of, U.S. Provisional Appl. No. 62/397,895, filed Sep. 21, 2016, which is incorporated by reference herein in its entirety.

FIELD OF THE INVENTION

The present disclosure generally relates to methods and systems for visualizing medical and diagnosis information from a clinical study. More specifically, the present disclosure relates to methods to visualize localization and severity coronary artery blockages and myocardium at risk of coronary disease.

BACKGROUND

Vascular diseases are often manifested by reduced blood flow due to atherosclerotic occlusion of vessels. For example, occlusion of the coronary arteries supplying blood to the heart muscle is a major cause of heart disease. Invasive procedures for relieving arterial blockage such as bypass surgery and stent placement with a catheter rely on estimates of occlusion characteristics and blood flow through the occluded artery. These estimates are based on measurements of occlusion size and/or blood flow. Unfortunately, current methods of occlusion size and blood flow measurement require invasive procedures such as coronary angiography, which requires cardiac catheterization. This procedure involves a long, thin, flexible catheter being placed into a blood vessel in the arm, groin (upper thigh), or neck; the catheter is then threaded to the heart. Through the catheter, a physician can perform a visual evaluation of the inner diameter of a vessel with cineangiography or fluoroscopy and/or use a small sensor on the tip of the wire (commonly a transducer) to measure parameters such as pressure, temperature, and flow to determine the severity of the lesion; and fractional flow reserve (FFR). These minimally invasive diagnostic tests on the heart carry the risk of stroke, heart attack, injury to the catheterized artery/heart, irregular heart rhythms, kidney damage, infection, and radiation exposure from X-rays. These procedures are time consuming, require expertise in the interpretation of the results and are expensive.

Stenosis geometry is also important in the therapeutic phase when balloon angioplasty, stenting or drug delivery procedures are subsequently performed. For example, precise stent placement is critical for reducing the risk of restenosis. Thus, decisions on whether or not to use any of the blockage relieving methods and which of the methods should be used are often based on partial information and do not take into account coronary collateralization. The ischemic stress often induces the increase in collateral circulation in coronary small vessel which at times will compensate for distal vessel blockage. Further, the evaluation of therapeutic success is also problematic, where both occlusion opening and stent position have to be evaluated. One class of methods, predominantly used today, require a lengthy procedure to find and determine severity, blockage to blood flow, of the lesion or lesions. Contemporary techniques evaluate the cardiac gradient phase-space changes and correlate the changes with cardiac computed tomography (CT), myocardial perfusion imaging, and cardiac angiography. The surface cardiac gradient contains detailed information on the electrophysiology of the chambers recorded. Because surface cardiac gradient represents the summation of the individual action potentials from each and every cardiac cell in syncytium, in theory, any information that might be determined from measurement of the orchestrated cellular action potential should be available on a "global" level in the surface. Moreover, although information relating to the influence of myocardial tissue architecture on conduction properties is inherent in the surface cardiac gradient, the challenge is in the discrimination of the pertinent information from these long quasi-periodic cardiac gradient signals while excluding noise contamination. Still further, there is a distinct lack of non-invasive tools available to enhance identification of high-risk patients and thus to trial preventive strategies in a non-invasive manner.

SUMMARY

Exemplified methods and systems facilitate presentation of data derived from measurements of the heart in a non-invasive procedure (e.g., via phase space tomography analysis). In particular, the exemplified methods and systems facilitate presentation of such measurements in a graphical user interface, or "GUI" (e.g., associated with a healthcare provider portal to be used by physicians, researchers, patients, etc.) and/or in a report for diagnosis of heart pathologies and disease, particularly coronary disease. The presentation facilitates a unified and intuitive visualization that includes three-dimensional visualizations and two-dimensional visualizations that are concurrently presented within a single interactive interface and/or report.

In particular, the system displays the results as a phase-space computed tomography model and analyzes the signals using a machine-learned analyses to report on a predictor of the presence of significant coronary artery disease (CAD) in the major coronary arteries. Additional predictors for specific localized regions of the heart may be similarly evaluated. The consequence of significant CAD is insufficient perfusion adversely affecting the associated myocardium, for example, due to ischemia. This exemplified methods represents an improved, elegant, and efficient process to assess the presence of ischemic heart disease compared to conventional angiographic tests by locating and imaging architectural features of the myocardium to characterize abnormalities in heart and cardiovascular function.

The phase space computed tomography imagery provides contextual information on cardiac health. The color and shape of the phase space tomographic image synthesizes and displays the electrical and functional status of the heart. The analysis of the physiological signals predicts the presence and location of significant coronary artery disease. The outcome is reported along with a display of the areas of affected myocardium associated with the underlying disease. These visualizations, together with a machine-learned prediction of CAD status, are presented in the healthcare provider portal.

In an aspect, a computer-implemented method is disclosed for formatting a display (e.g., a graphical user interface and/or a report) to present summary information and visualizations of myocardial tissue overlaid with visualizations of data (e.g., generated from phase space tomography analysis) that identifies myocardium at risk and/or coronary arteries that are blocked (e.g., to be used, at least in part, to direct treatment of a patient associated with the data). The method includes generating, by a processor, for a graphical user interface and/or for a report (e.g., either comprising a two or more displayable panels) (e.g., to be displayed on a stationary or mobile computing device associated with a client), one or more graphical visualizations including a first graphical visualization and, optionally, a second graphical visualization, from a data set that identifies myocardium at risk and coronary arteries that are blocked, the data set comprising a plurality of parameters (e.g., coronary risk values or artery blockage percent values, etc.) each associated with a corresponding heart segment of a plurality of heart segments, wherein each of the heart segments correspond to an anatomical structure of the heart. The first graphical visualization (e.g., being presented in a first displayable panel or in a same panel with the second graphical visualization) includes a first graphical element corresponding to a first three-dimensional visualization of myocardial tissue (e.g., a standardized or customized rendered 3D model derived from one or more medical scans, e.g., CT scans, or an animated 3D model of the heart), wherein the first three-dimensional visualization of myocardial tissue comprises a plurality of surface areas each associated with a heart segment of the plurality of heart segments (e.g., 17 pre-defined surface areas corresponding to 17 heart segments), and one or more second graphical elements (e.g., a coloration, surface texture, or animation) that are overlaid over, or that replaces, a surface area of the plurality of surfaces areas of the first graphical element, the surface area corresponding a given heart segment having a parameter that identifies myocardium at risk (or include one or more coronary arteries that are blocked). The second graphical visualization, when presented, includes a third graphical element corresponding to a first two-dimensional visualization (e.g., a 17-segment circular image or model or a 17-segment coronary tree image or model) of the plurality of heart segments, the first two-dimensional visualization comprising a plurality of surfaces each corresponding to a segment of the plurality of heart segments, and one or more fourth graphical elements (e.g., a coloration, surface texture, or animation) that are overlaid over, or that replaces, a surface of the plurality of surfaces of the third graphical element, the surface corresponding to the given heart segment having the parameter that identifies the myocardium at risk. The method further includes causing, by the processor, the plurality of graphical visualizations to be presented (e.g., in the graphical user interface or as the report) on a display of a computing device or to be stored as a report file (e.g., an electronic file or a tangible file).

In some embodiments, the method includes generating, by the processor, for the graphical user interface or for the report, a third graphical visualization and a fourth graphical visualization of the plurality of graphical visualizations, from a second data set that identifies myocardium at risk and coronary arteries that are blocked (e.g., the second data set being associated with measurements collected from the patient at a second time instance, the second time instance being different from a time instance associated with measurements associated with the data set), the second data set comprising a second plurality of parameters (e.g., coronary risk values or artery blockage percent values, etc.) associated with the plurality of heart segments. The third graphical visualization includes a fifth graphical element corresponding to a second three-dimensional visualization of myocardial tissue, wherein the second three-dimensional visualization of myocardial tissue comprises a second plurality of surface areas associated with the plurality of heart segments (e.g., wherein the three-dimensional visualization and the second three-dimensional visualization are the same), and one or more sixth graphical elements (e.g., a coloration, surface texture, or animation) that are overlaid over, or that replaces, a second surface area of the second plurality of surfaces areas of the fifth graphical element, the second surface area corresponding a given heart segment having a parameter of the second data set that identifies myocardium at risk (or include one or more coronary arteries that are blocked). The fourth graphical visualization includes a seventh graphical element corresponding to a second two-dimensional visualization of the plurality of heart segments, the second two-dimensional visualization comprising a second plurality of surfaces corresponding to the plurality of heart segments, and one or more eight graphical elements (e.g., a coloration, surface texture, or animation) that are overlaid over, or that replaces, a second surface of the second plurality of surfaces, the second surface corresponding to the given heart segment having the parameter of the second data that identifies the myocardium at risk. The method further includes causing, by the processor, the third graphical visualization and the fourth graphical visualization to be presented (e.g., in the graphical user interface or as the report) on the display of the computing device or to be stored as a part of the report file.

In some embodiments, the method further includes generating, by the processor, for the graphical user interface or for the report, a ninth graphical element and a tenth graphical element, wherein the ninth graphical element corresponds to a time stamp associated with measurements collected from the patient at a second time instance, the second time instance being different from a first time instance associated measurements associated with the data set, and wherein the tenth graphical element corresponds to a second time stamp associated with the first time instance; and causing, by the processor, the ninth graphical element and the tenth graphical element visualizations to be presented on the display of the computing device or to be stored as a part of the report file.

In some embodiments, the first graphical visualization further includes a third three-dimensional visualization (e.g., a side view) of myocardial tissue, wherein the third three-dimensional visualization of myocardial tissue is the same as the first three-dimensional visualization (e.g., a front view), wherein the first three-dimensional visualization is rendered in accordance with a first viewing perspective (e.g., a front viewing perspective), and wherein the third three-dimensional visualization is rendered in accordance with a second viewing perspective (e.g., a side viewing perspective), wherein the first viewing perspective is different from the second viewing perspective.

In some embodiments, the second viewing perspective is rotated between about 80 degrees and about 110 degrees (e.g., orthogonal or almost orthogonal) from the first viewing perspective.

In some embodiments, the one or more second graphical elements are selected from the group consisting of a coloration, a surface texture, and an animation (e.g., that distinguishes the one or more second graphical elements from surrounding graphical elements).

In some embodiments, the one or more fourth graphical elements are selected from the group consisting of a coloration, a surface texture, and an animation (e.g., that distinguishes the one or more fourth graphical elements from surrounding graphical elements).

In some embodiments, the one or more second graphical elements comprise a first coloration set and the one or more fourth graphical elements comprise a second coloration set, the first coloration set being the same as the second coloration set.

In some embodiments, the first two-dimensional visualization comprises a plurality of elongated graphical elements collectively forming a coronary tree, wherein each of the plurality of elongated graphical elements corresponds to a heart segment of the plurality of heart segments.

In some embodiments, the first two-dimensional visualization includes a center graphical element (e.g., Segment 17); a first set of graphical elements (e.g., Segments 13, 14, 15, and 16) each having a radial area that extends between a first radius value and a second radius value and that collectively surrounds the center graphical element; a second set of graphical elements (e.g., Segments 7, 8, 9, 10, 11, 12) each having a radial area that extends between the second radius value and a third radius value and that collectively surrounds the first set of graphical elements; and a third set of graphical elements (e.g., Segments 1, 2, 3, 4, 5, and 6) each having a radial area that extends between the third radius value and a fourth radius value and that collectively surrounds the second set of graphical elements.

In some embodiments, the first two-dimensional visualization of the second graphical visualization includes a plurality of elongated graphical elements collectively forming a coronary tree, wherein each of the plurality of elongated graphical elements corresponds to a heart segment of the plurality of heart segments; and the second graphical visualization further includes a second two-dimensional visualization of the myocardial tissue, the second two-dimensional visualization including a plurality of surfaces each corresponding to a segment of the plurality of heart segments. The second two-dimensional visualization includes a center graphical element (e.g., Segment 17); a first set of graphical elements (e.g., Segments 13, 14, 15, and 16) each having a radial area that extends between a first radius value and a second radius value and that collectively surrounds the center graphical element; a second set of graphical elements (e.g., Segments 7, 8, 9, 10, 11, 12) each having a radial area that extends between the second radius value and a third radius value and that collectively surrounds the first set of graphical elements; and a third set of graphical elements (e.g., Segments 1, 2, 3, 4, 5, and 6) each having a radial area that extends between the third radius value and a fourth radius value and that collectively surrounds the second set of graphical elements.

In some embodiments, the graphical user interface and the report is caused to be displayed (e.g., via a web portal) on a stationary or a mobile computing device associated with a client (e.g., a physician, a clinician, a technician, a patient, an administrator, etc.).

In some embodiments, the report is caused to be stored (e.g., saved or printed) as a non-transitory file.

In some embodiments, the plurality of parameters comprise coronary risk values (e.g., corresponding to a coronary disease).

In some embodiments, the plurality of parameters comprise artery blockage percent values (e.g., fractional flow reserve value).

In some embodiments, the data set is collected and analyzed via phase space tomography analysis (or other non-invasive diagnostic procedures).

In some embodiments, the data set is collected from an angiographic study (or other invasive diagnostic procedures).

In some embodiments, the first three-dimensional visualization of myocardial tissue comprises a standardized rendered 3D model derived from one or more medical scans (e.g., CT scans).

In some embodiments, the first three-dimensional visualization of myocardial tissue comprises a customized rendered 3D model derived from one or more medical scans (e.g., CT scans) associated with the patient.

In some embodiments, the first three-dimensional visualization of myocardial tissue comprises an animated rendered 3D model of the heart.

In some embodiments, the plurality of heart segments comprises 17 heart segments each corresponding to an anatomical structure of the heart.

In another aspect, a system is disclosed that performs one or more of the above methods.

In another aspect, a computer readable medium is disclosed, the computer readable medium comprising instructions, wherein executed of the instructions, cause the processor, to perform one or more of the above methods.

In another aspect, a method is disclosed of formatting a display (e.g., a graphical user interface or a report) to present summary information and visualizations of myocardial tissue overlaid with visualizations of data that identifies point of interest in the heart tissue. The method includes generating, by a processor, for a graphical user interface or for a report, a first graphical visualization and a second graphical visualization, from a data set, wherein the first graphical visualization comprises a three-dimensional visualization of myocardial tissue, wherein the second graphical visualization comprises a first two-dimensional visualization of the plurality of heart segments, wherein each of the three-dimensional visualization and the second graphical visualization graphically presents (e.g., coloration or identifier) a point of interest in the heart tissue (e.g., myocardial tissue or coronary arteries) based on the data set; and causing, by the processor, the first graphical visualization and the second graphical visualization to be presented (e.g., in the graphical user interface or as the report) on a display of a computing device or to be stored as a report file (e.g., an electronic file or a tangible file).

In another aspect, a system is disclosed that performs the above method.

In another aspect, a computer readable medium is disclosed, the computer readable medium comprising instructions, wherein executed of the instructions, cause the processor, to perform the above method.

In another aspect, a report (e.g., a non-transitory report) is disclosed, the report being generated according to the above method.

In another aspect, a method is disclosed of generating a report to present summary information and visualizations of myocardial tissue overlaid with visualizations of data that identifies myocardium at risk and/or coronary arteries that are blocked (e.g., to be used, at least in part, to direct treatment of a patient associated with the data). The method includes generating, by a processor, a first report for a graphical user interface, the first report comprising a plurality of graphical visualizations; and generating, by the processor, contemporaneous with generation of the first report, a second report for storage as a file, the second report comprising the plurality of graphical visualizations.

In some embodiments, the plurality of graphical visualizations comprises a first graphical visualization and a second graphical visualization, wherein the first graphical visualization (e.g., being presented in a first displayable panel or in a same panel with the second graphical visualization) comprises: a first graphical element corresponding to a first three-dimensional visualization of myocardial tissue (e.g., a standardized or customized rendered 3D model derived from one or more medical scans, e.g., CT scans, or an animated 3D model of the heart), wherein the first three-dimensional visualization of myocardial tissue comprises a plurality of surface areas each associated with a heart segment of the plurality of heart segments (e.g., 17 pre-defined surface areas corresponding to 17 heart segments), and one or more second graphical elements (e.g., a coloration, surface texture, or animation) that are overlaid over, or that replaces, a surface area of the plurality of surfaces areas of the first graphical element, the surface area corresponding a given heart segment having a parameter that identifies myocardium at risk (or include one or more coronary arteries that are blocked). The second graphical visualization comprises: a third graphical element corresponding to a first two-dimensional visualization (e.g., a 17-segment circular image or model or a 17-segment coronary tree image or model) of the plurality of heart segments, the first two-dimensional visualization comprising a plurality of surfaces each corresponding to a segment of the plurality of heart segments, and one or more fourth graphical elements (e.g., a coloration, surface texture, or animation) that are overlaid over, or that replaces, a surface of the plurality of surfaces of the third graphical element, the surface corresponding to the given heart segment having the parameter that identifies the myocardium at risk.

In some embodiments, the method includes generating, by the processor, for the graphical user interface or for the report, a third graphical visualization and a fourth graphical visualization of the plurality of graphical visualizations, from a second data set that identifies myocardium at risk and coronary arteries that are blocked (e.g., the second data set being associated with measurements collected from the patient at a second time instance, the second time instance being different from a time instance associated with measurements associated with the data set), the second data set comprising a second plurality of parameters (e.g., coronary risk values or artery blockage percent values, etc.) associated with the plurality of heart segments, wherein the third graphical visualization comprises: a fifth graphical element corresponding to a second three-dimensional visualization of myocardial tissue, wherein the second three-dimensional visualization of myocardial tissue comprises a second plurality of surface areas associated with the plurality of heart segments (e.g., wherein the three-dimensional visualization and the second three-dimensional visualization are the same), and one or more sixth graphical elements (e.g., a coloration, surface texture, or animation) that are overlaid over, or that replaces, a second surface area of the second plurality of surfaces areas of the fifth graphical element, the second surface area corresponding a given heart segment having a parameter of the second data set that identifies myocardium at risk (or include one or more coronary arteries that are blocked). The fourth graphical visualization comprises: a seventh graphical element corresponding to a second two-dimensional visualization of the plurality of heart segments, the second two-dimensional visualization comprising a second plurality of surfaces corresponding to the plurality of heart segments, and one or more eight graphical elements (e.g., a coloration, surface texture, or animation) that are overlaid over, or that replaces, a second surface of the second plurality of surfaces, the second surface corresponding to the given heart segment having the parameter of the second data that identifies the myocardium at risk. The method further includes causing, by the processor, the third graphical visualization and the fourth graphical visualization to be presented (e.g., in the graphical user interface or as the report) on the display of the computing device or to be stored as a part of the report file.

In some embodiments, the method includes generating, by the processor, for the graphical user interface or for the report, a ninth graphical element and a tenth graphical element, wherein the ninth graphical element corresponds to a time stamp associated with measurements collected from the patient at a second time instance, the second time instance being different from a first time instance associated measurements associated with the data set, wherein the tenth graphical element corresponds to a second time stamp associated with the first time instance; and causing, by the processor, the ninth graphical element and the tenth graphical element visualizations to be presented on the display of the computing device or to be stored as a part of the report file.

In some embodiments, the first graphical visualization further comprises: a third three-dimensional visualization (e.g., a side view) of myocardial tissue, wherein the third three-dimensional visualization of myocardial tissue is the same as the first three-dimensional visualization (e.g., a front view), wherein the first three-dimensional visualization is rendered in accordance with a first viewing perspective (e.g., a front viewing perspective), wherein the third three-dimensional visualization is rendered in accordance with a second viewing perspective (e.g., a side viewing perspective), wherein the first viewing perspective is different from the second viewing perspective.

In some embodiments, the second viewing perspective is rotated between about 80 degrees and about 110 degrees (e.g., orthogonal or almost orthogonal) from the first viewing perspective.

In some embodiments, the one or more second graphical elements are selected from the group consisting of a coloration, a surface texture, and an animation (e.g., that distinguishes the one or more second graphical elements from surrounding graphical elements).

In some embodiments, the one or more fourth graphical elements are selected from the group consisting of a coloration, a surface texture, and an animation (e.g., that distinguishes the one or more fourth graphical elements from surrounding graphical elements).

In some embodiments, the one or more second graphical elements comprise a first coloration set and the one or more fourth graphical elements comprise a second coloration set, the first coloration set being the same as the second coloration set.

In some embodiments, the first two-dimensional visualization comprises a plurality of elongated graphical elements collectively forming a coronary tree, wherein each of the plurality of elongated graphical elements corresponds to a heart segment of the plurality of heart segments.

In some embodiments, the first two-dimensional visualization comprises: a center graphical element (e.g., Segment 17); a first set of graphical elements (e.g., Segments 13, 14, 15, and 16) each having a radial area that extends between a first radius value and a second radius value and that collectively surrounds the center graphical element; a second set of graphical elements (e.g., Segments 7, 8, 9, 10, 11, 12) each having a radial area that extends between the second radius value and a third radius value and that collectively surrounds the first set of graphical elements; and a third set of graphical elements (e.g., Segments 1, 2, 3, 4, 5, and 6) each having a radial area that extends between the third radius value and a fourth radius value and that collectively surrounds the second set of graphical elements.

In some embodiments, the first two-dimensional visualization of the second graphical visualization comprises a plurality of elongated graphical elements collectively forming a coronary tree, wherein each of the plurality of elongated graphical elements corresponds to a heart segment of the plurality of heart segments; and wherein the second graphical visualization further comprises a second two-dimensional visualization of the myocardial tissue, the second two-dimensional visualization comprising a plurality of surfaces each corresponding to a segment of the plurality of heart segments. The second two-dimensional visualization further comprises: a center graphical element (e.g., Segment 17); a first set of graphical elements (e.g., Segments 13, 14, 15, and 16) each having a radial area that extends between a first radius value and a second radius value and that collectively surrounds the center graphical element; a second set of graphical elements (e.g., Segments 7, 8, 9, 10, 11, 12) each having a radial area that extends between the second radius value and a third radius value and that collectively surrounds the first set of graphical elements; and a third set of graphical elements (e.g., Segments 1, 2, 3, 4, 5, and 6) each having a radial area that extends between the third radius value and a fourth radius value and that collectively surrounds the second set of graphical elements.

BRIEF DESCRIPTION OF THE DRAWINGS

The components in the drawings are not necessarily to scale relative to each other and like reference numerals designate corresponding parts throughout the several views:

FIG. 4A illustrates an exemplary embodiment of a report that presents visualizations of FIG. 1 that identifies myocardium at risk and/or coronary arteries that are blocked in accordance with an illustrative embodiment.

FIG. 4B illustrates an exemplary embodiment of a report that presents visualizations of FIG. 2 in accordance with an illustrative embodiment.

FIG. 4C illustrates an exemplary embodiment of a report that presents visualizations of FIG. 3 in accordance with an illustrative embodiment.

FIG. 5B shows a front exploded view of the depiction of the three-dimensional tomographic model. FIG. 5C shows a left exploded view of the depiction of the three-dimensional tomographic model. FIG. 5D shows a back exploded view of the depiction of the three-dimensional tomographic model. FIG. 5E shows a right exploded view of the three-dimensional tomographic model.

FIGS. 18A and 18B illustrate an exemplary embodiment of pulsing animated sequence in accordance with an illustrative embodiment.

DETAILED SPECIFICATION

Figure 1:
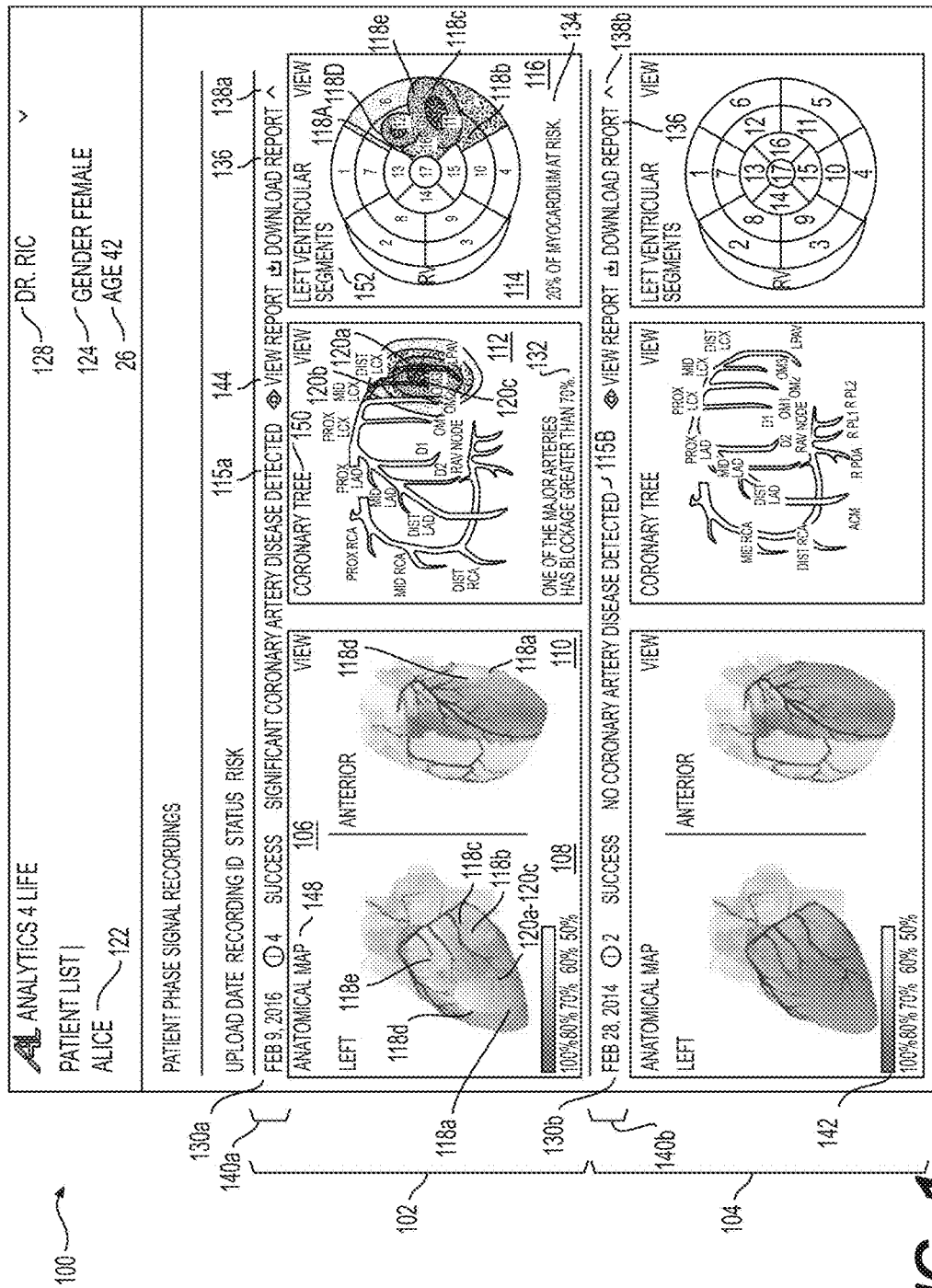
FIG. 1 illustrates an exemplary embodiment of a graphical user interface of a healthcare provider portal configured to present summary information and visualizations of myocardial tissue that identifies myocardium at risk and/or coronary arteries that are blocked in accordance with an illustrative embodiment.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes. Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the Examples included therein and to the Figures and their previous and following description.

It is understood that throughout this specification the identifiers "first", "second", "third", "fourth", "fifth", "sixth", and such, are used solely to aid in distinguishing the various components and steps of the disclosed subject matter. The identifiers "first", "second", "third", "fourth", "fifth", "sixth", and such, are not intended to imply any particular order, sequence, amount, preference, or importance to the components or steps modified by these terms.

Exemplary Graphical User Interface of Coronary Artery Disease Study

The inventors have observed that in assessing the functional characteristics of the heart's ability to effectively generate and conduct electrical current, localize areas of abnormality can be determined by linking areas of ischemia with the arterial blockages that lead to that ischemia. Indeed, the presence/absence of coronary disease and the approximate location of occlusion can be predicted. By using a learning set, e.g., in machine learning, consisting of both physiological signals and the presence/absence of CAD and approximate location of any occlusion, training can be, and have been, performed either a multi-categorical basis, in which all possible locations are considered as a classification exercise, or on a location-by-location basis in which one formula may be created to identify the presence of an occlusion in specific arteries of the heart. Varying degrees of locational sensitivity may also be presented, such as distinguishing between occlusions that occur on the proximal, mid, or distal locations on each artery and their distributions or focusing only on identifying the major artery.

It is noted that areas of ischemia linked to the identified instances of coronary artery disease can be represented on a 17-segment diagram. The exemplified system and method provides a three-dimensional model of the heart, which serves as a scaffold for presentation of data. When a prediction of the presence of significant coronary artery disease (e.g., a region identified having myocardium at risk and/or coronary arteries that are blocked) is made with a classification of location, the volume of potentially ischemic tissue can be highlighted on this scaffold as a machine-learned tomographic representation of this status.

FIG. 1 illustrates an exemplary graphical user interface 100 of a healthcare provider portal configured to present summary information visualizations of myocardial tissue that identifies myocardium at risk and/or coronary arteries that are blocked in accordance with an illustrative embodiment. The graphical user interface 100 can be used, for example, to direct diagnostics and treatment of a patient with coronary disease at least in part along with other studies and assessments. The visualizations, for a given report of a study, include multiple depictions of a rotatable three-dimensional anatomical map 106 of cardiac regions of affected myocardium, an equivalent, corresponding two-dimensional view of the major coronary artery 114, and an equivalent, corresponding two-dimensional 17-segment view 116. The graphical user interface 100 is used, in some embodiments, with a non-invasive cardiac assessment system that evaluates acquired cardiac phase gradient measurements and transforms such measurements to location and image architectural features of the myocardium for characterizing abnormalities in the heart and in cardiovascular functions.

In FIG. 1, measurements from two such cardiac assessment studies of a given patient (shown as "Alice . . . 122") are presented (shown in 102 and 104, corresponding to studies performed on "Feb. 28, 2014" and on "Feb. 9, 2016" (see identifiers 130*a* and 130*b*)). In addition to, or as an alternative to, the patient name, other patient identifier(s) may be used, for example, patient hospital's identification number, patient's date of birth. The graphical user interface 100 is scrollable to present multiple cardiac assessment studies. In some embodiments, all available cardiac assessment studies for a given patient is presented with the graphical user interface 100.

As shown in the embodiment of FIG. 1, each of the available cardiac assessment studies are presented with a header region (shown as 140*a*, 140*b*) that identifies the presence, or no presence, of significant coronary artery disease being detected (shown as 115*a* and 115*b*). The identifier (associated with 115*a* and 115*b*) may be a clinical determination of presence or absence of significant coronary artery disease "CAD" in which the definition of significant CAD is pre-defined (e.g., >70% blockage and/or FFR<0.8). In some embodiments, the predictor are developed through machine learning and uses the same definition of significant CAD in the training and verification processes.

As shown, each of the header regions 140*a*, 140*b* includes a corresponding graphical widget (shown as 138*a* and 138*b*) that expands or collapses the report for that study. Indeed, the exemplified presentation facilitates a comprehensive and intuitive evaluation of historical and/or current cardiac assessment studies that facilitates the analysis and diagnosis of pathologies and disease over time. If desired, only one dataset may also be presented in some embodiments.

In some embodiments, results from other tests, for example, invasive nuclear stress test and other coronary assessment studies, may be imported into the portal for concurrent presentation. The results may also be imported from angiographic reports (e.g., those that have been acquired via invasive procedures) and other heterogeneous sources for comparative study and analysis. Because the inputs of the visualization engine used herein can import data generated by conventional invasive procedures, data from past procedures that were collected via different methods may be concurrently presented together with data collected via non-invasive methods (e.g., via phase space tomography analysis).

In each of the study, as noted above, the graphical user interface 100 presents visualizations for multiple rotatable three-dimensional tomographic representation of an anatomical map 106 of cardiac regions of affected myocardium, an equivalent, corresponding two-dimensional view of the major coronary artery 114, and an equivalent, corresponding two-dimensional 17-segment view 116. The three-dimensional anatomical map 106 is depicted in a first pane (e.g., 108) corresponding to a left tomographic view of the heart and a second pane (e.g., 110) corresponding to a perspective view of the heart. The left tomographic view (e.g., 108) and the perspective view (e.g., 110) of the heart may be rendered as a same tomographic representation of the heart, but with different views. The left tomographic view is presented, in the default view, to normalize the graphical user interface 100 to the left ventricle and left atrium which has a greater risk of coronary disease (e.g., as compared to the right ventricle). Similarly, to emphasize or normalize the view to the left side of the heart, the perspective view (e.g., 110) of the heart is presented in the default view to prospectively show each of, or a majority of, the segments associated with the left ventricle and the left atrium. Further, as shown in the embodiment of FIG. 1, only segments associated with the left ventricle and the left atrium are rendered, while segments with the right ventricle and the right atrium are not rendered. Rather, a partially transparent tomographic representation of a complete heart is shown to provide context of the left side of the heart with respect to the complete heart.

As shown, each study is presented with four panes (e.g., for studies referenced by 102 and 104, panes 108, 110, 114, and 116 are shown). Other numbers of panes may be presented in the graphical user interface 100 for a given study. The number of panes and the type of panes may be customizable by the user.

Two data sets are presented in the exemplary visualizations of the embodiment of the graphical user interface 100—regions of myocardium at risk and blockages of major arteries in the heart. The two-dimensional view of the major coronary artery 114 presents location information associated with the blockage within the major arteries and the severity of the blockage(s). The two-dimensional 17-segment view 116 highlights segments having myocardium at risk and the severity of the risk. In some embodiments, one of the two data set (e.g., artery blockage percent values) can be derived from other data set (risk of significant coronary disease being present, or not present, for a given region (e.g., segment of a 17-segment heart model) of the heart).

Each three-dimensional anatomical map 106, when depicted, presents the combined information associated with the regions of myocardium at risk and the blockages of major arteries in the heart. Each three-dimensional anatomical map 106 is an anatomical map that comprises 17 distinct three-dimensional regions that corresponds to each of the 17 segments shown in the two-dimensional 17-segment view 116. The 17 distinct three-dimensional regions are positioned with no spatial gap therebetween to visually create a contiguous structure. Each three-dimensional anatomical map 106 also comprise a plurality of distinct rendering elements that correspond to each of the major arteries in the two-dimensional view of the major coronary artery 114.

In other embodiments, each three-dimensional anatomical map 106 comprises a single distinct rendering elements that includes segmentation boundaries that defines the 17 segments corresponding to those shown in the two-dimensional 17-segment view 116.

To provide contrast between the information associated with regions of myocardium at risk and blockages of major arteries in the heart, the regions of myocardium at risk are rendered with a static coloration while the blockages of major arteries in the heart rendered with an animated sequence of a volume that depicts an expansion and a contraction of a graphical element of the sequence with time. The periodicity of the contraction and expansion depiction, in some embodiments, is set at about 1 Hz (corresponding to a normal heart rate of an adult at rest). The pulsing depiction, in some embodiments, can have a period corresponding to a heartbeat (e.g., a period between 50 and 80 pulses or variations per minute). Indeed, the presentation facilitates a unified and intuitive visualization that includes three-dimensional visualizations and two-dimensional visualizations that are concurrently presented within a single interactive interface and/or report.

To this end, in FIG. 1, a first graphical visualization (e.g., associated with 106) and a second graphical visualization (e.g., associated with 114 or 116) is presented from a data set that identifies myocardium at risk and coronary arteries that are blocked. The data set, in some embodiments, includes a plurality of parameters (e.g., coronary risk values or artery blockage percent values, etc.) derived from, for example, but not limited to, a phase space tomography analysis. Other anatomical views of the heart and myocardial tissue can be presented and used in conjunction with the disclosed embodiments.

Exemplary 17-Segment View

As noted above, coronary risk values (e.g., of myocardium at risk of significant coronary disease, e.g., area of estimated ischemia) associated with each heart segment that corresponds to an anatomical structure of the heart is presented in the 17-segment view. This 17-segment mapping is commonly used to represent areas of ischemia identified by the nuclear stress test and hence is an appropriate scaffold for the representation of ischemia here.

In some embodiments, the risk value for each of the 17 segments is determined based, in part, on estimated stenosis parameter that is provided to the graphical user interface 100. The stenosis may be normalized according to a pre-defined set of risk tiers that classify the segment as having no risk, some risk, and high risk of ischemia. In other embodiments, the risk values from a determined predictor can connote presence of or no presence of significant CAD. Other methods of segmentation and predictors of the heart may be used.

Exemplary Coronary Artery Mapping

As noted above, blockages of major arteries in the heart is presented in the two-dimensional view of the major coronary artery 114. In some embodiments, the blockages are presented as an artery blockage percent values (e.g., based on an estimated fractional flow reserve value or based on the predictor of significant CAD). The two-dimensional view of the major coronary artery 114, in some embodiments, includes the Prox. RCA, Mid RCA, Dist. RCA, Prox. LAD, Mid. LAD, Dist. LAD, Mid. LCX, Dist. LCX, LPAV, etc.). Other arteries of the heart may be presented. In addition, other parameters and associated data can be graphically and/or textually presented according to the embodiments described herein. As a non-limiting example, parameters associated with presence of plaque (e.g., via cholesterol, cellular waste products, other fats, calcium, proteins) or blood clots (e.g., thrombus) may be presented.

Exemplary Data Set and Risk Score Determination

Table 1 is an exemplary embodiment of a dataset that is generated from a phase-space tomographic analysis that is performed for given study of a patient that is used to generate the visuals for the three-dimensional anatomical maps 106 of cardiac regions of affected myocardium, the two-dimensional view of the major coronary artery 114, and the two-dimensional 17-segment view 116. The output of the phase-space tomographic analysis is a general predictor of a pre-defined risk of coronary disease. For example, the output can be predictor for the clinical determination of presence or absence of significant CAD in which the definition of significant CAD is: >70% blockage and/or FFR<0.8. As an alternative, or in addition to, the output includes specific predictors for risk of coronary disease localized for a given region of the heart (e.g., corresponding to pre-defined segment of the 17 segments model) to be presented in the two-dimensional 17-segment view 116. The output of the phase-space tomographic analysis (predictors of risk of coronary disease localized for a given region of the heart) is also used, in whole, or in part, to determine a percentage blockage for the two-dimensional view of the major coronary artery 114 in some embodiments.

As shown, Table 1 includes a fractional flow reserve (FFR) parameter, an estimated stenosis parameter, and an estimated ischemia parameter for a plurality of segments corresponding to major vessels in the heart, including the Left Main Artery (LMA), the Proximal Left Circumflex Artery (Prox LCX), the Mid-Left Circumflex Artery (Mid LCX), the Distal Left Circumflex Artery (Dist LCX), the Left Posterior Atrioventricular (LPAV), the First Obtuse Marginal Branch (OM1), the Second Obtuse Marginal Branch (OM2), the Third Obtuse Marginal Branch (OM3), the Proximal Left Anterior Descending Artery (Prox LAD), the Mid Left Anterior Descending Artery (Mid LAD), the Distal Left Anterior Descending Artery (Dist LAD), the Left Anterior Descending First Diagonal Branch (LAD D1), the Left Anterior Descending Second Diagonal Branch (LAD D2), the Proximal Right Coronary Artery (Prox RCA), the Mid Right Coronary Artery (Mid RCA), the Distal Right Coronary Artery (Dist RCA), and the Acute Marginal Branch Right of the Posterior Descending Artery (AcM R PDA). In Table 1, the parameters for myocardial ischemia estimation, stenosis identification, and/or fractional flow reserve estimation are shown in a range of 0 to 1. Other scaling or ranges may be used.

In some embodiments, calculation for risk scores to be presented in the two-dimensional 17-segment view 116 and the three-dimensional anatomical maps 106 may be determined by conventional means incorporating risk factors associated with coronary disease once and takes into account the non-invasive measurements for fractional flow reserve, stenosis, and ischemia. Such risk factors can include age of the patient, sex of the patient, family history, smoking history, history of high blood pressure, weight, among others. In some embodiments, the risk scores may be editable by the clinician or by the healthcare service provider administrator via a customization input to the graphical user interface 100. In the examples herein, a given segment of the 17-segments are presented as having a myocardium at risk when 20% of the myocardium are at risk (for example, as shown via 134).

Calculation for blockage(s) to be presented in the two-dimensional view of the major coronary artery 114 and the

TABLE 1

| Segment | Vessel | FFR | Stenosis | Ischemia |
|---|---|---|---|---|
| 1 | Left Main Artery (LMA) | 0.90 | 0.50 | 0.20 |
| 2 | Proximal Left Circumflex Artery (Prox LCX) | 0.85 | 0.60 | 0.30 |
| 3 | Mid-Left Circumflex Artery (Mid LCX) | 0.93 | 0.35 | 0.15 |
| 4 | Distal Left Circumflex Artery (Dist LCX) | 1.00 | 0.00 | 0.00 |
| 5 | Left Posterior Atrioventricular (LPAV) | 1.00 | 0.00 | 0.00 |
| 6 | First Obtuse Marginal (OM1) | 0.60 | 0.95 | 0.72 |
| 7 | Second Obtuse Marginal (OM2) | 1.00 | 0.00 | 0.00 |
| 8 | Third Obtuse Marginal (OM3) | 1.00 | 0.00 | 0.00 |
| 9 | Proximal Left Anterior Descending Artery (Prox LAD) | 1.00 | 0.00 | 0.00 |
| 10 | Mid Left Anterior Descending Artery (Mid LAD) | 1.00 | 0.00 | 0.00 |
| 11 | Distal Left Anterior Descending Artery (Dist LAD) | 0.70 | 0.80 | 0.63 |
| 12 | LAD D1 | 0.00 | 0.00 | 0.75 |
| 13 | LAD D2 | 0.00 | 0.00 | 0.00 |
| 14 | Proximal Right Coronary Artery (Prox RCA) | 0.00 | 0.00 | 0.00 |
| 15 | Mid Right Coronary Artery (Mid RCA) | 0.00 | 0.00 | 0.00 |
| 16 | Distal Right Coronary Artery (Dist RCA) | 0.00 | 0.00 | 0.18 |
| 17 | Acute Marginal Branch Right of the Posterior Descending Artery (AcM R PDA) | 0.00 | 0.00 | 0.00 | three-dimensional anatomical maps 106 may be determined by conventional means accounting for the non-invasive measurements for fractional flow reserve and ischemia. In some embodiments, the calculation for blockages may be editable by the clinician or by the healthcare service provider administrator via a customization input to the graphical user interface 100. In the examples herein, the major arteries are presented as having a blockage when the blockage is greater than 70% (for example, as shown via caption 132).

Three-Dimensional Anatomical Map of Cardiac Regions of Affected Myocardium and Arteries As shown in the embodiment of FIG. 1, the three-dimensional anatomical maps 106 are shown as a left view and a perspective view of a rendered three-dimensional model. The rendered three-dimensional model here is derived from a computed tomography (CT) scan of a standard subject. Indeed, the same rendered 3D model of a standardized subject is used as a scaffold for the presentation of specific patient study data.

It is contemplated that a customized rendered 3D model derived from one or more medical scans, e.g., CT scans, of a given patient may be used in conjunction with the embodiments disclosed herein. It is further contemplated that an animated 3D model of the heart can be used in conjunction with the embodiments disclosed herein.

Aggregated Visualization of the Three-Dimensional Anatomical Map, the 17-Segment Map, and the Coronary Map As noted above, the depiction of the two-dimensional view of the major coronary artery 114 presents location information associated with the blockage within the major arteries and the severity of the blockage(s); the two-dimensional 17-segment view 116 highlights segments having myocardium at risk and the severity of the risk; and, the three-dimensional anatomical maps 106 present the combined information associated with the regions of myocardium at risk and the blockages of major arteries in the heart.

Figure 2:
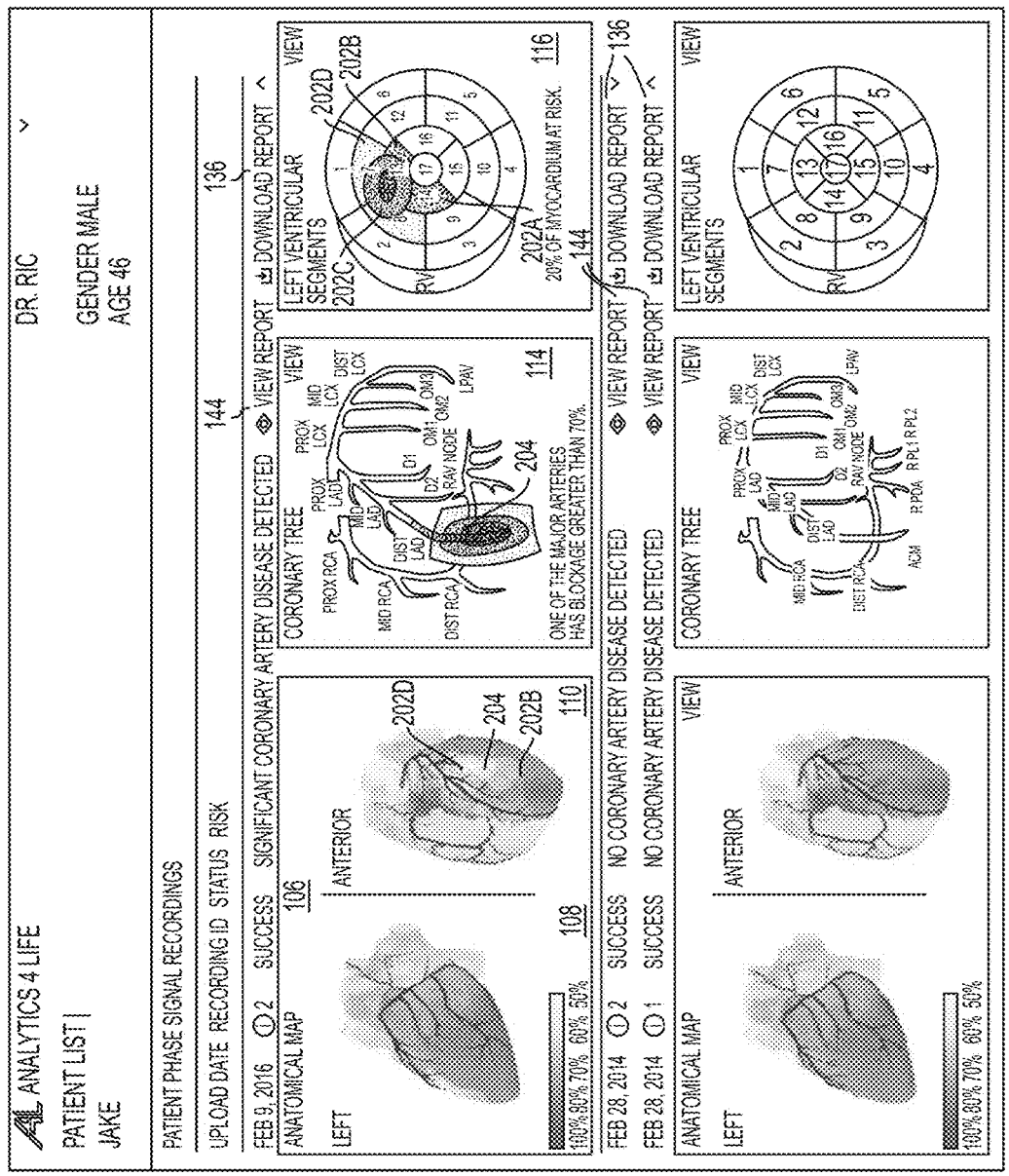
FIG. 2 illustrates the exemplary embodiment of the graphical user interface of FIG. 1 that is presenting exemplary embodiment of data for another patient.
Figure 3:
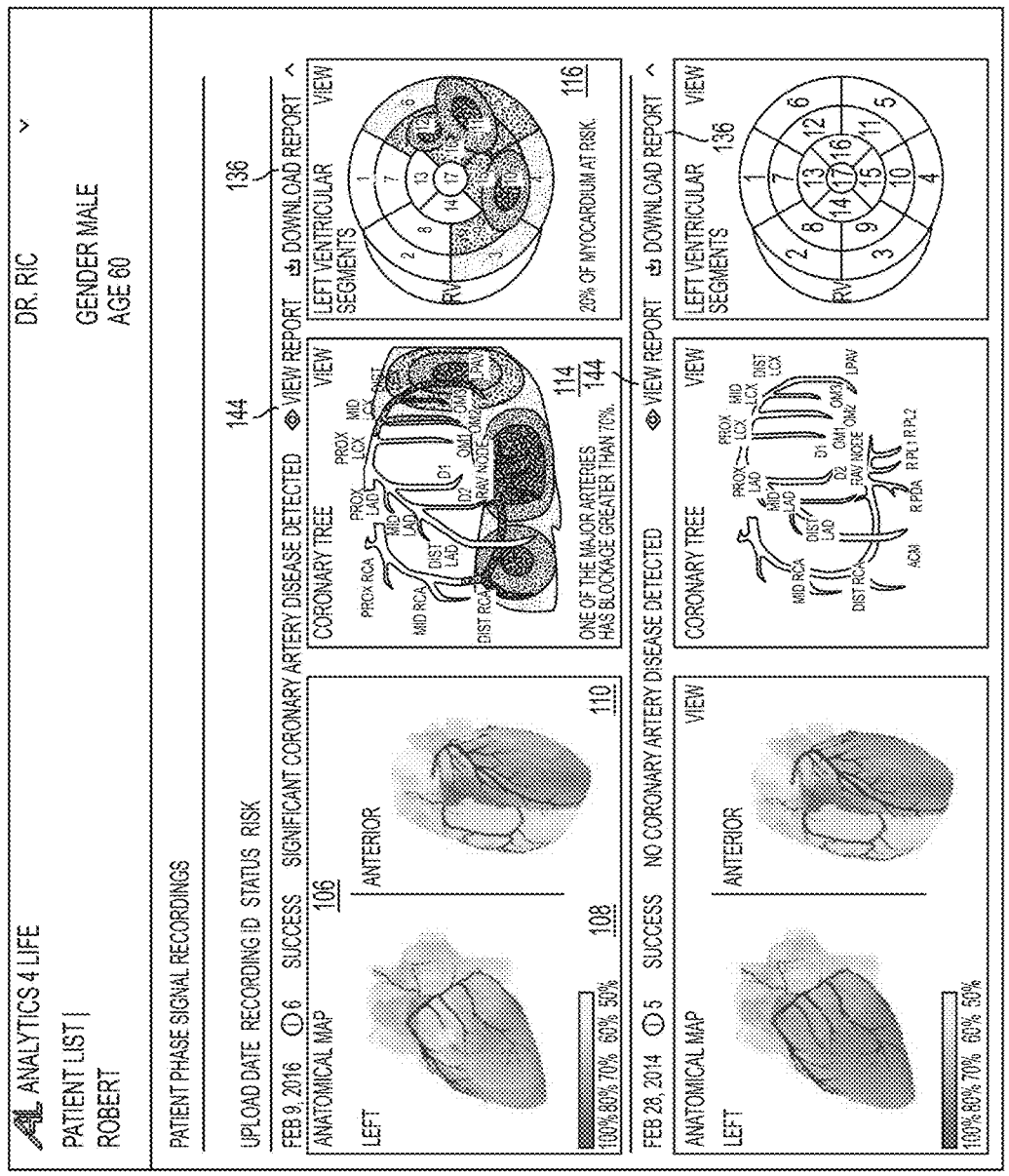
FIG. 3 illustrates the exemplary embodiment of the graphical user interface of FIG. 1 that is presenting exemplary embodiment of data for yet another patient.

As a non-limiting example, six studies of three hypothetical patients are shown in FIGS. 1, 2, 3 that includes two studies for patient "Alice B" in FIG. 1, two studies for patient "Jake S" in FIG. 2, and two studies for patient "Robert K" in FIG. 3.

In FIG. 1, each depiction of the three-dimensional anatomical maps 108 and 110 and the two-dimensional 17-segment view 116 shows risk associated with five left segments of the heart, namely segment "16" (corresponding to the apical lateral region, shown with arrow 118*a*), segment "11" (corresponding to the mid inferolateral region, shown with arrow 118*b*), segment "5" (corresponding to the basal inferolateral region, shown with arrow 118*c*), segment "12" (corresponding to the mid anterolateral region, shown with arrow 118*d*), and segment "6" (corresponding to the basal anterolateral region, shown with arrow 118*e*). The three-dimensional anatomical maps 108 and 110 and the two-dimensional 17-segment view 116 are rendered with varying levels of colorations that corresponds to risk scores. As shown, the risk scores are presented over a range between 50% and 100% risk. In the embodiment of the graphical user interface 100, the mapping of the coloration for the risk score is presented as a bar scale 142.

In addition, in FIG. 1, each depiction of the three-dimensional anatomical maps 108 and 110 and the two-dimensional view of the major coronary artery 114 shows blockages in three regions of the major arteries of the heart, namely the left posterior atrioventricular artery "LPAV" 120*a*, the distal left circumflex artery "Dist LCX" 120*b*, and the third obtuse marginal artery "OM3" 120*c*. The blockages are shown as a pulsing animated sequence in which the graphical element(s) of the sequence vary in size and coloration that may correspond to, e.g., various pathologies of that portion of the heart (e.g. blockage and/or ischemic tissue) and to varying degrees of severity, for example, compared to the greyscale coloration of tissue for which an abnormality or pathology is not presented. Other variations, in any combination, in size and coloration (as well as translucency, as discussed below) are contemplated in which both normal and abnormal tissue may be displayed to optimize diagnosis, visualization, and ease of use for both healthcare professionals as well as patients. Indeed, the aggregated visualization facilitates diagnosis of heart pathologies and disease.

In FIG. 2, each of the depictions of the three-dimensional anatomical maps 108 and 110 and the two-dimensional 17-segment view 116 shows risk associated with four left segments of the heart, namely segment "13" (corresponding to the apical anterior region, shown with arrow 202*a*), segment "14" (corresponding to the apical septal region, shown with arrow 202*b*), segment "8" (corresponding to the mid anteroseptal region, shown with arrow 202*c*), and segment "7" (corresponding to the mid anterior region, shown with arrow 202*d*). And, each of the three-dimensional anatomical maps 108 and 110 and the two-dimensional view of the major coronary artery 114 shows artery blockage in the distal left anterior descending artery "Dist LAD" (204).

In FIG. 3, each of depictions of the three-dimensional anatomical maps 108 and 110 and the two-dimensional 17-segment view 116 shows risk associated with ten segments of the heart, namely, segment "15" (corresponding to the apical inferior region), segment "16" (corresponding to the apical lateral region), segment "9" (corresponding to the mid inferoseptal region), segment "10" (corresponding to the mid inferior region), segment "11" (corresponding to the mid inferolateral region), segment "12" (corresponding to the mid anterolateral region), segment "3" (corresponding to the basal inferoseptal region), segment "4" (corresponding to the basal inferior region), segment "5" (corresponding to the basal inferolateral region), and segment "6" (corresponding to the basal anterolateral region). And, each of the depictions of the three-dimensional anatomical maps 108 and 110 and the two-dimensional view of the major coronary artery 114 shows blockage in the distal right coronary artery "Dist RCA", the acute marginal branch "AcM", the acute marginal branch right of the posterior descending artery "R PDA", "R PL1", "R PL2", the distal left circumflex artery "Dist LCX", the second obtuse marginal artery "OM2", the third obtuse marginal artery "OM3", and the left posterior atrioventricular artery "LPAV").

For all of the embodiments discussed herein (including those depicted in the Figures and those not so depicted), other textual summaries, data (e.g., tabular form) and non-graphical information may be presented on any page of graphical user interface 100, in any format, alone or in combination with graphically presented information (e.g., two-dimensional visualizations, three-dimensional visualizations, animations, etc.).

Example Report of Coronary Artery Disease Study

FIG. 4A illustrates an exemplary report that presents visualizations of FIG. 1 that identifies myocardium at risk and/or coronary arteries that are blocked in accordance with an illustrative embodiment. FIG. 4B illustrates an exemplary report that presents visualizations of FIG. 2 in accordance with an illustrative embodiment. FIG. 4C illustrates an exemplary report that presents visualizations of FIG. 3 in accordance with an illustrative embodiment.

As shown in each of the embodiments of FIGS. 4A, 4B, and 4C, each report includes a depictions of the three-dimensional anatomical maps 402, 404 (corresponding to those shown in panes 108 and 110, though shown on a different heart scaffold model), a depiction of the two-dimensional view 406 of the coronary tree (corresponding to that shown in pane 114), and a depiction of the two-dimensional 17-segment view 408 (corresponding to that shown in pane 116).

Referring still to FIGS. 4A, 4B, and 4C, a report 400, as a non-limiting example, includes the patient data and medical record data. The patient data may include patient name, gender, and age. The medical record data may include a record identifier 410 and attending doctor identifier 412. Report 400 as shown in FIG. 4 also includes summary information (as previously discussed), such as caption 415 and the "Findings" section 417 of summary information (which may or may not include a key 419 for the reader mapping segment identifiers to the name of a given artery as well as any footnotes or other information or indicia).

As shown in the embodiments of FIGS. 1-3, the report 400 may be viewed electronically, e.g., in a portable document format (PDF), as an image file, or as any number of other document types, when the button 144 ("View Report" 144) is selected by the user. The report 400 may be downloaded, e.g., a portable document format (PDF), an image file, or other document types, when the button 136 ("Download Report" 136) is selected by the user.

17-Segment Map with Arterial Mapping

Figure 5A:
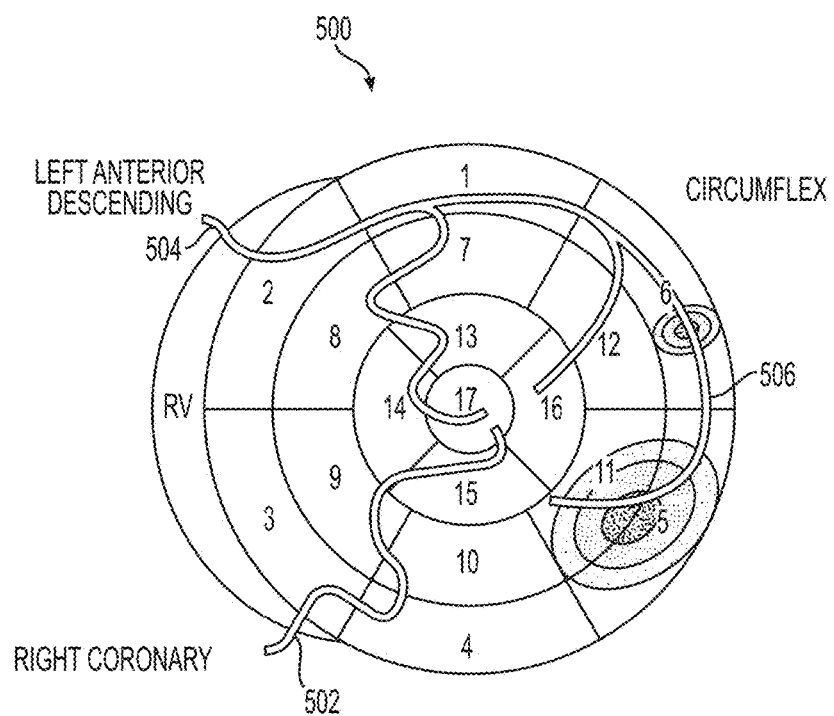
FIG. 5A shows another exemplary depiction of an embodiment of a 17-segment map of the heart having depictions of the arterial mapping of the right coronary artery, the left anterior descending artery, and the circumflex artery in accordance with an illustrative embodiment.

FIG. 5A shows a depictions of an exemplary 17-segment map 500 of the heart having arterial mapping of the right coronary artery 502, the left anterior descending artery 504, and the circumflex artery 506 in accordance with an illustrative embodiment. As shown, the arterial mapping of the right coronary artery 502 is depicted as a graphical overlay showing the spatial location of the right coronary artery superimposed over the 17-segment model of the heart. Specifically, the arterial mapping of the right coronary artery 502 is shown to span over segment 17 (associated with the apex region), segment 15 (associated with the apical inferior region), segment 14 (associated with the apical septal region), segment 9 (associated with the mid inferoseptal region), segment 10 (associated with the mid interior region), segment 4 (associated with the basal inferior region), and segment 3 (associated with the basal inferoseptal region).

Similarly, the arterial mapping of the left anterior descending artery 504 is shown superimposed over segment 17 (associated with the apex region), segment 14 (associated with the apical septal region), segment 13 (associated with the apical anterior region), segment 8 (associated with the mid anteroseptal region), segment 7 (associated with the mid anterior region), segment 1 (associated with the basal anterior region), and segment 2 (associated with the basal anteroseptal region). Also shown is the arterial mapping of the circumflex artery 606, which branches from the left anterior descending artery along a first branch along segment 6 (associated with the basal anterolateral region) to segment 12 (associated with the mid anterolateral region), and segment 16 (associated with the apical lateral region) and along a second branch along segment 6 to segment 5 (associated with the basal inferolateral region), and segment 11 (associated with the mid inferolateral region).

The arterial mapping, and depictions thereof, of the right coronary artery 502, the left anterior descending artery 504, and the circumflex artery 506, in some embodiments, are generated by spatially mapping locations of the respective arterial vessel, for a standard anatomy, onto a 2-dimensional projection of the 17 segments. To this end, significant CAD identified for a given segment of the 17 segment, e.g., due to ischemia can be visualized with respect to the segment and with respect to the right coronary artery, the left anterior descending artery, and the circumflex artery per the arterial mapping (502, 504, and 506).

In some embodiments, in addition to identification of the occlusions at a major artery, varying degrees of locational sensitivity may also be presented to distinguish between occlusions that occur, for example, at the proximal, mid, or distal locations on each artery and their distributions. For example, as shown in the embodiment of FIG. 5A, an occlusion of the mid portion of the circumflex artery is indicated which would impact segments 6, 5 and 11.

Other arterial mapping of arteries of the heart can be displayed in a similar manner, for example, the left marginal artery, the diagonal branch, the right marginal artery, the posterior descending artery, among others.

Exemplary Tomographic Model of the Anatomical Map

Figure 5B:
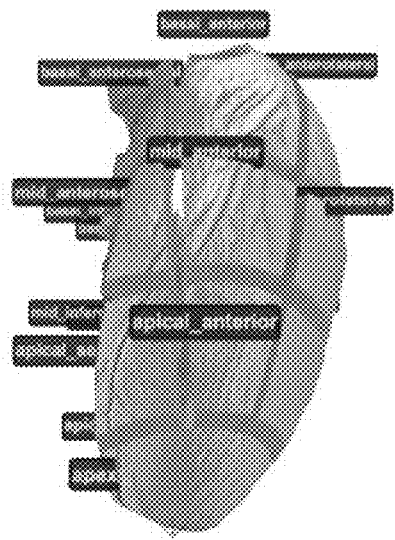
FIGS. 5B, 5C, 5D, and 5E each shows different views of depictions of a three-dimensional tomographic model of the complete heart used to generate the depiction of the three-dimensional anatomical map (e.g., 108 and 110).
Figure 5C:
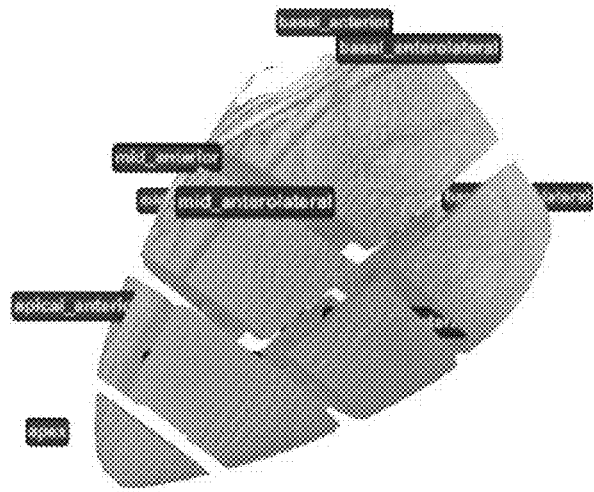
Figure 5D:
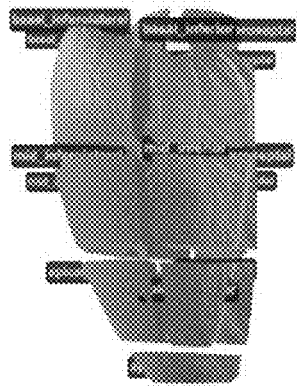
Figure 5E:
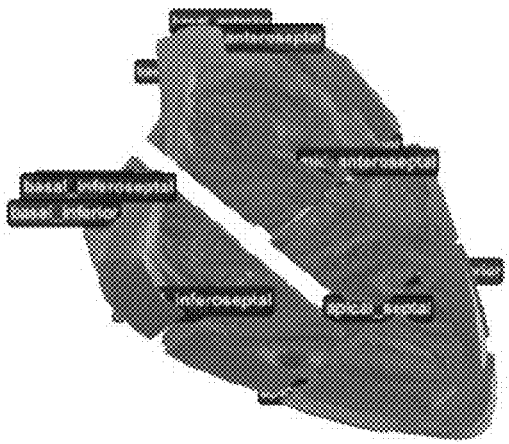

FIGS. 5B, 5C, 5D, and 5E show different views of depictions of a three-dimensional tomographic model of the complete heart used to generate the three-dimensional anatomical map (e.g., 108 and 110). As shown, the three-dimensional tomographic model is segmented into 17 distinct three-dimensional regions and are shown partially exploded. FIG. 5B shows a front exploded view of a depiction of the three-dimensional tomographic model. FIG. 5C shows a left exploded view of a depiction of the three-dimensional tomographic model. FIG. 5D shows a back exploded view of a depiction of the three-dimensional tomographic model. FIG. 5E shows a right exploded view of a depiction of the three-dimensional tomographic model.

Figure 5F:
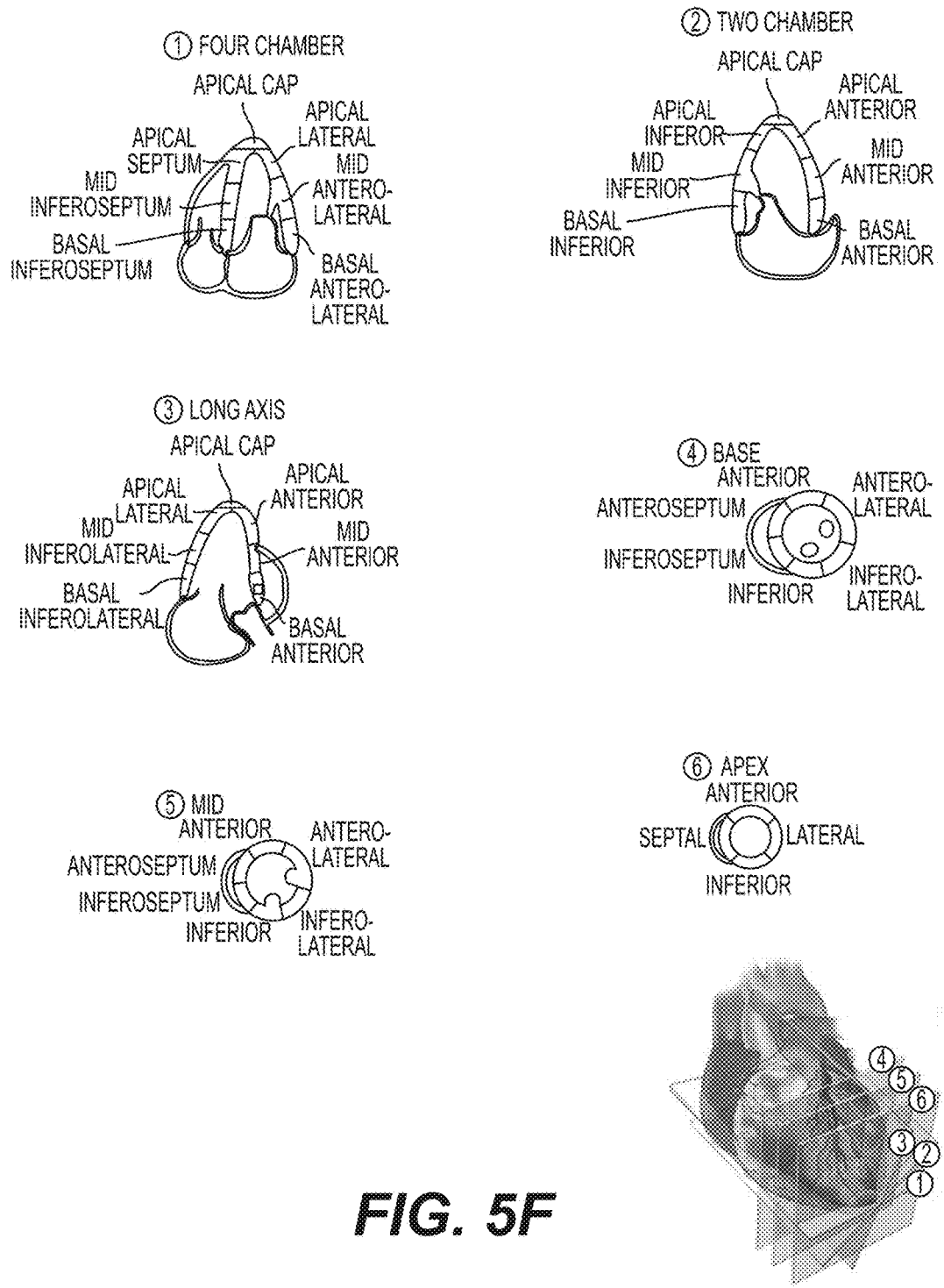
FIG. 5F shows the segmentation planes of the left ventricular region of the heart that defines the depictions of 17 segments.
Figure 5G:
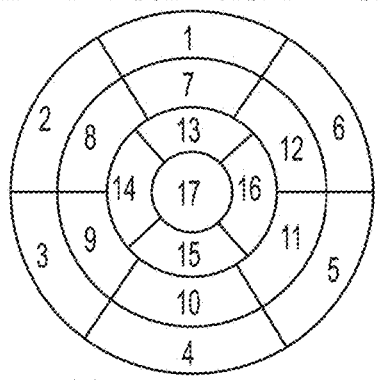
FIG. 5G provides a table of exemplary nomenclatures for the 17 segments.

FIG. 5F shows the segmentation planes of the left ventricular region of the heart that defines the 17 segments. FIG. 5G provides a table of the nomenclature for the 17 segments.

Figure 6A:
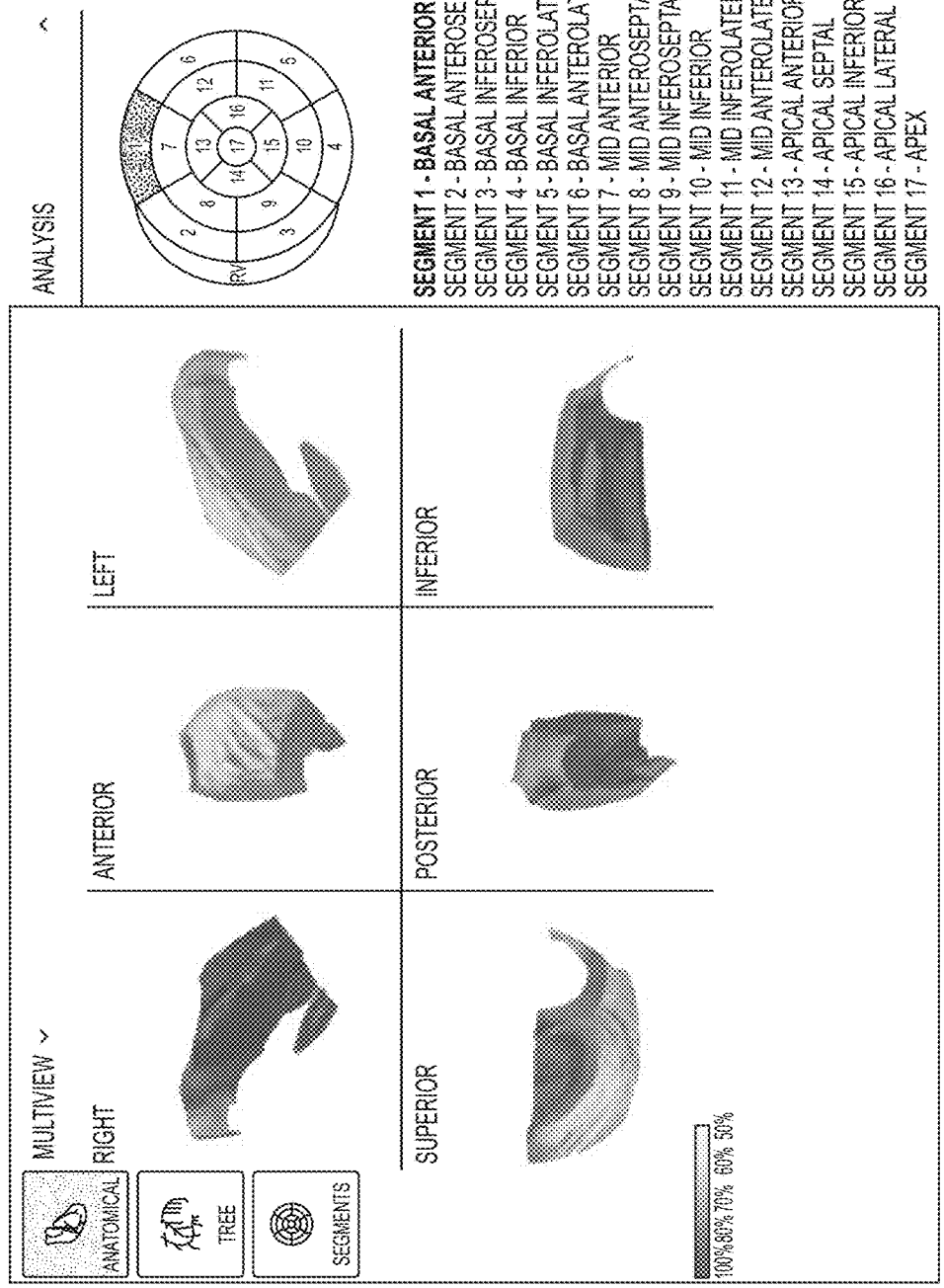
FIGS. 6A, 6B, 6C, 6D, 6E, 6F, 6G, 6H, 6I, 6J, 6K, 6L, 6M, 6N, 6O, 6P, and 6Q each shows different views of each depiction of the three-dimensional tomographic model of the 17 segments of FIGS. 5B, 5C, 5D, and 5E in accordance with an illustrative embodiment.
Figure 6B:
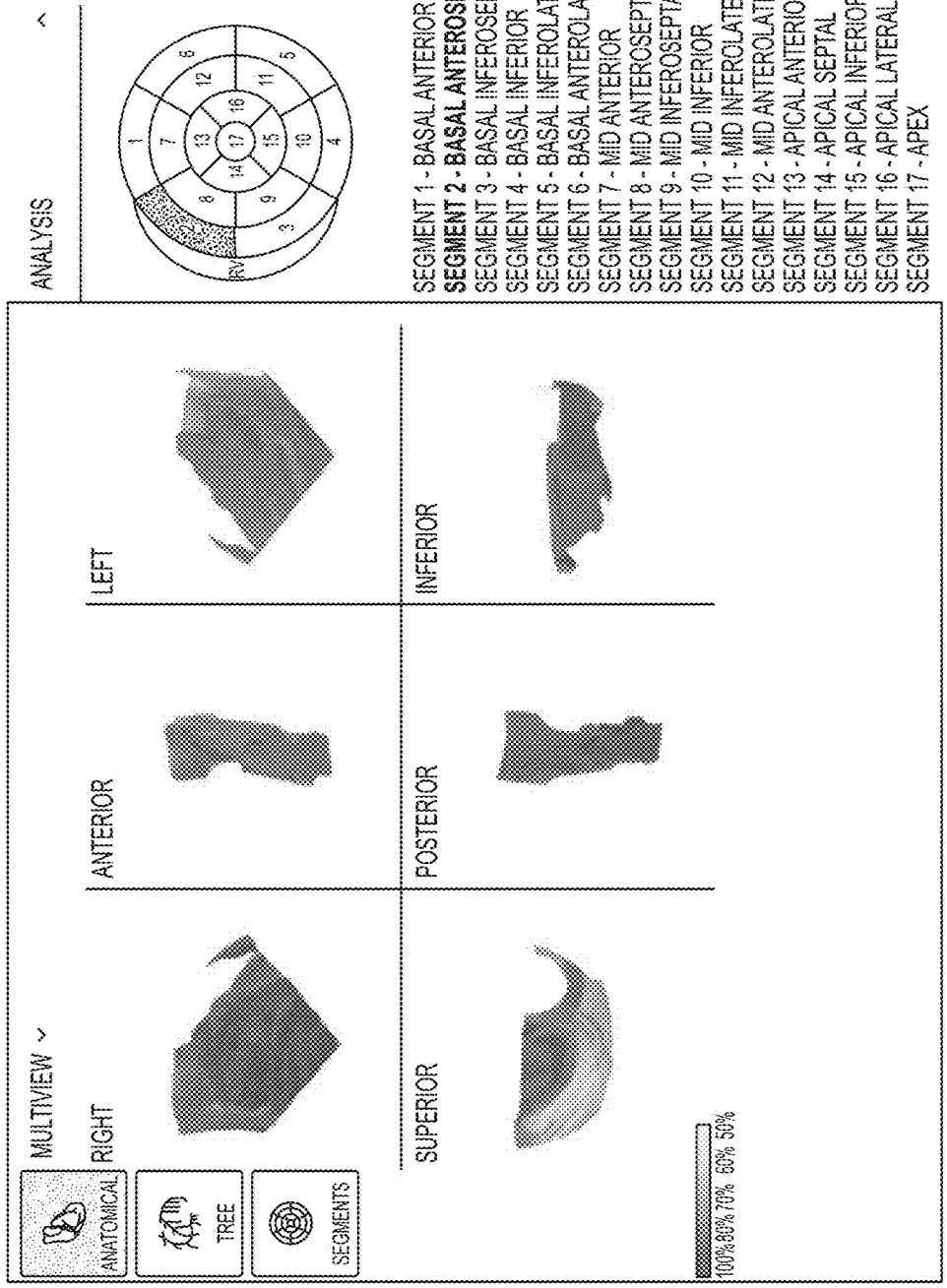
Figure 6C:
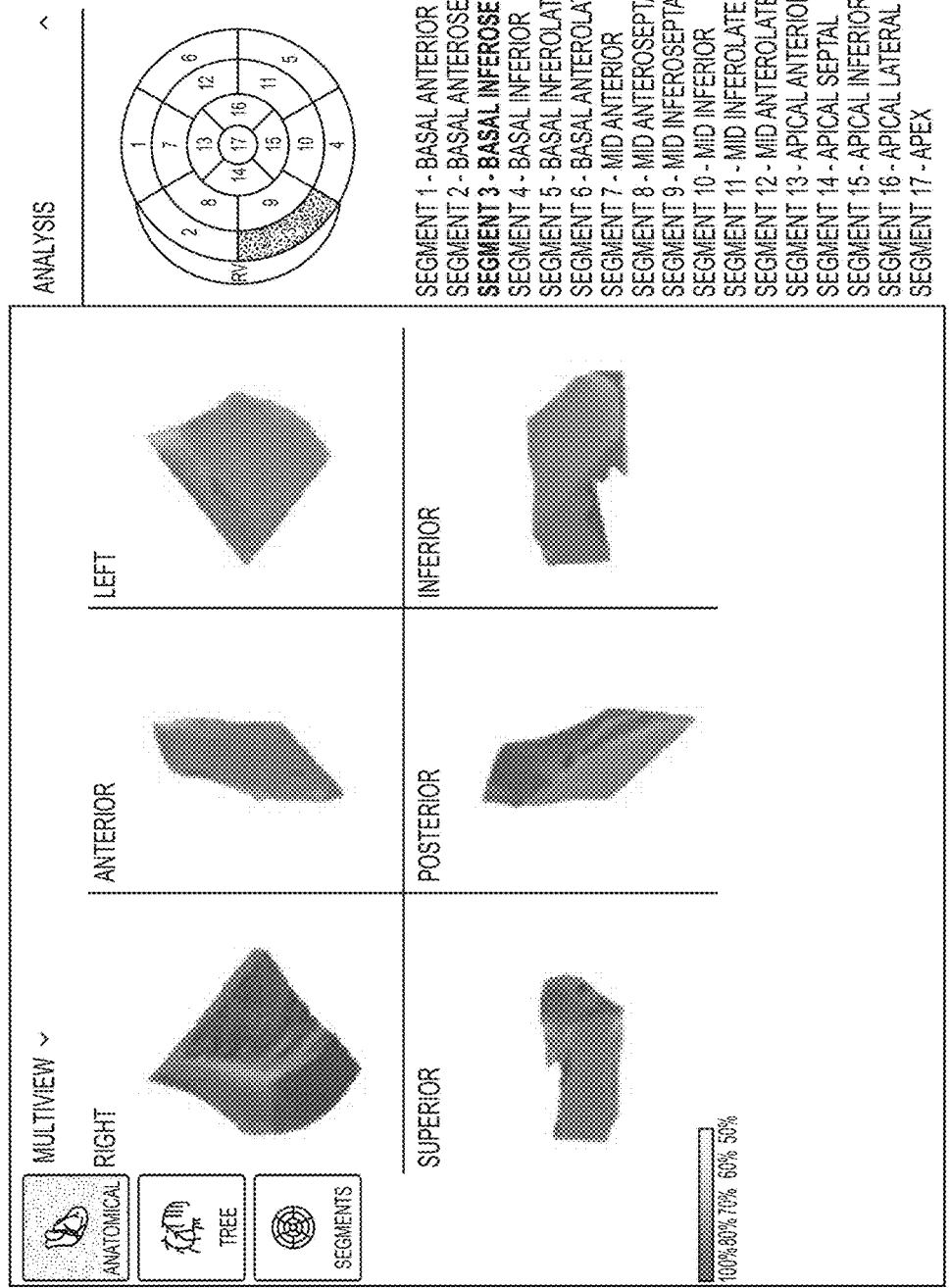
Figure 6D:
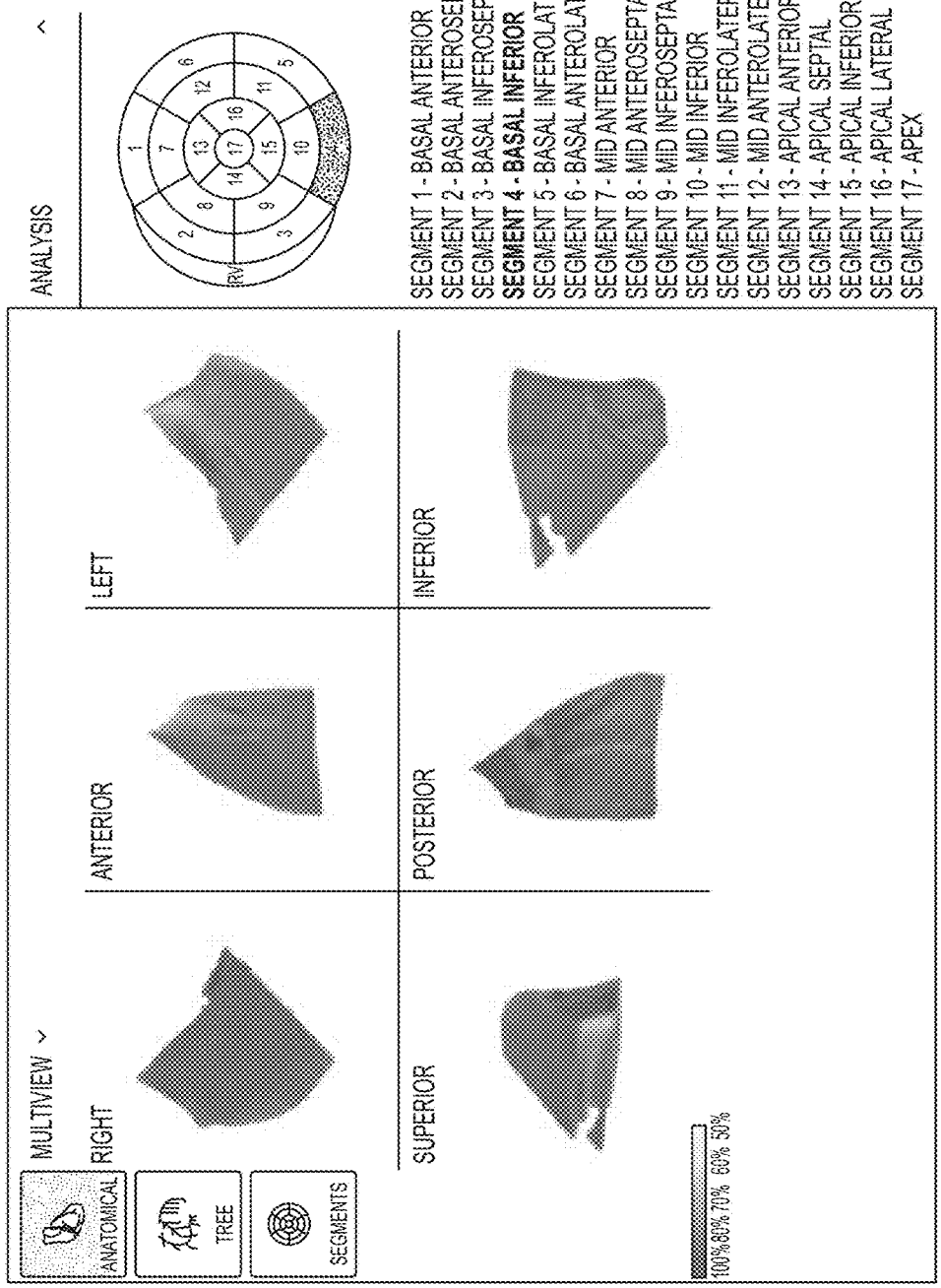
Figure 6E:
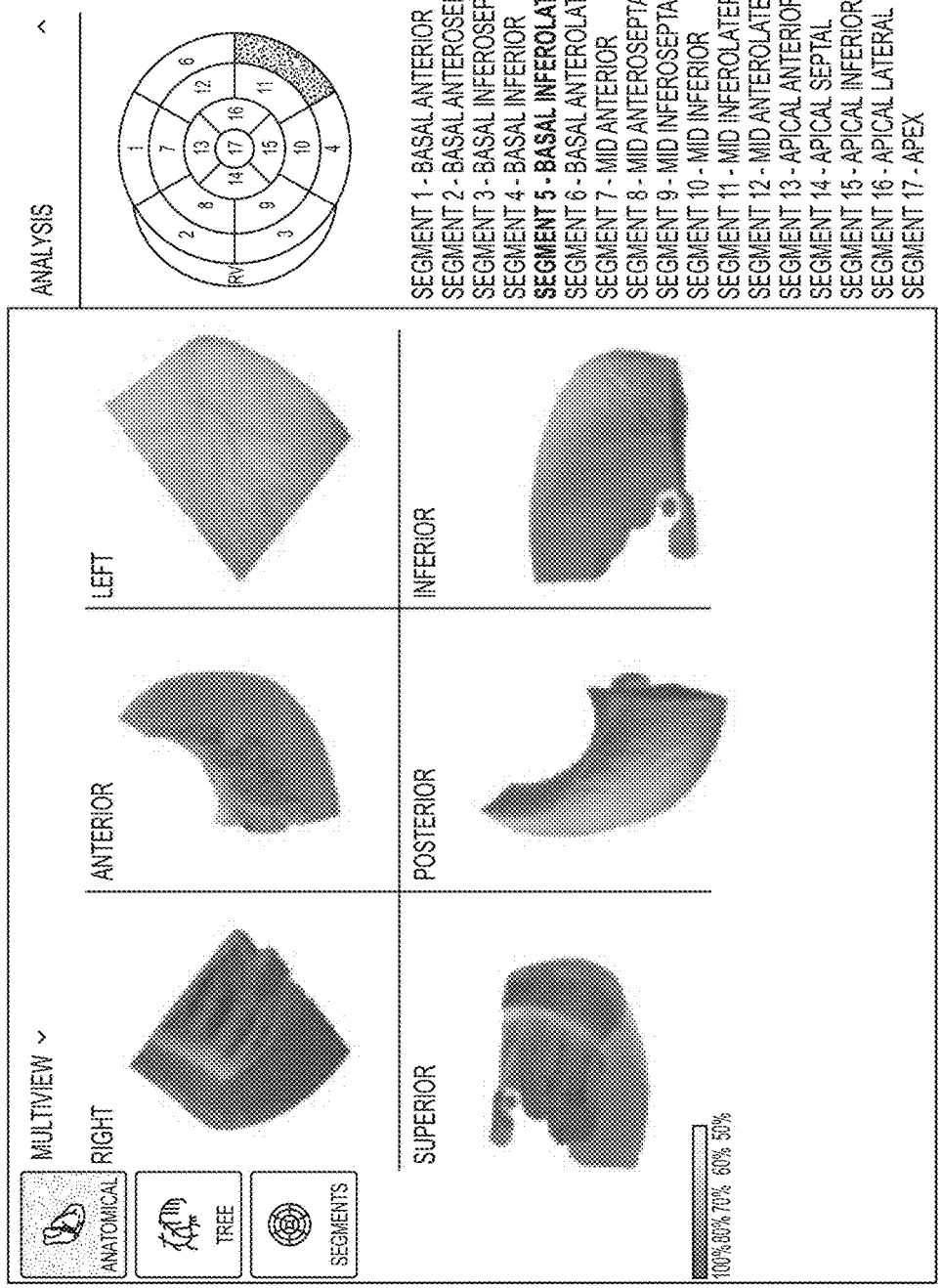
Figure 6F:
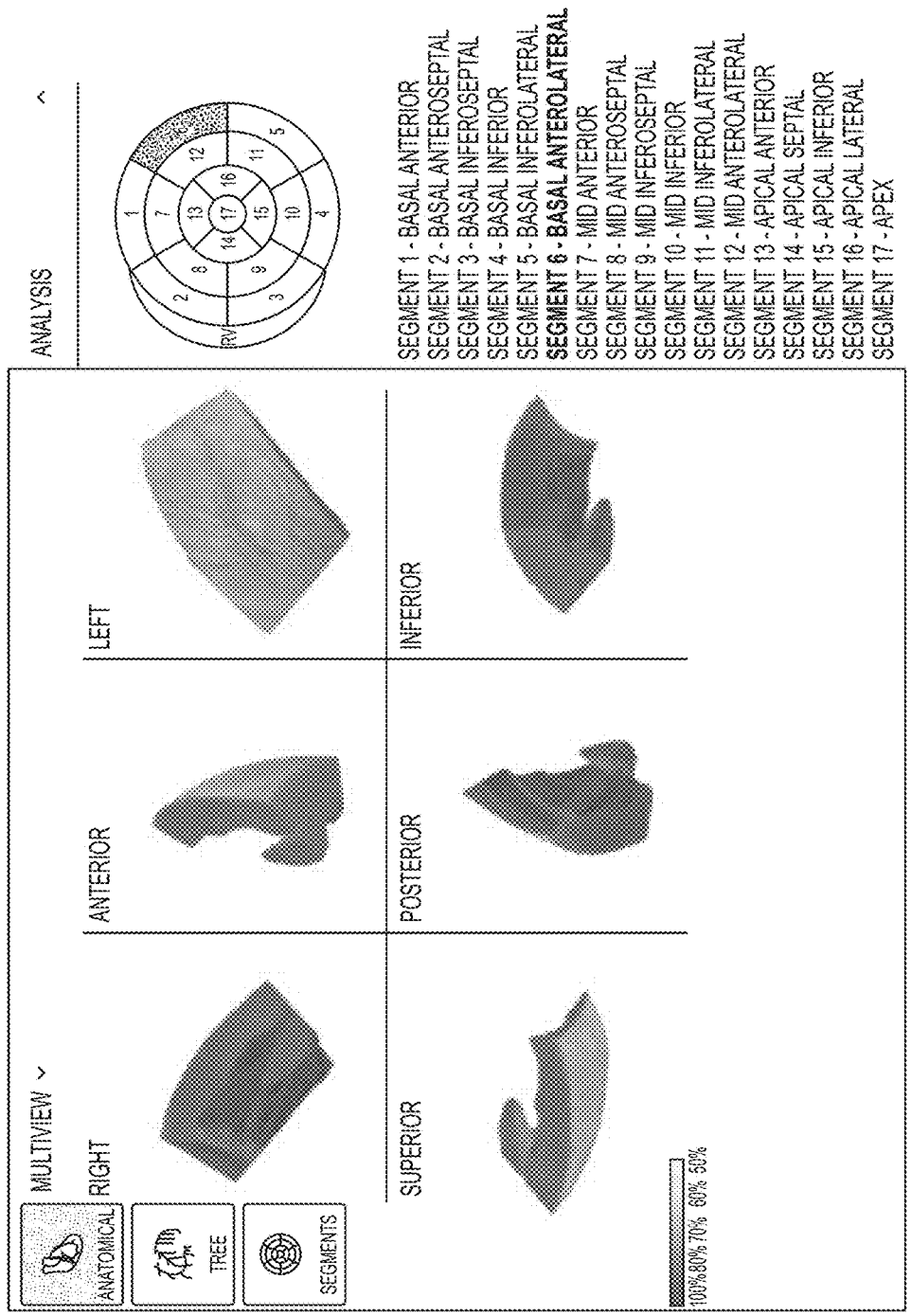
Figure 6G:
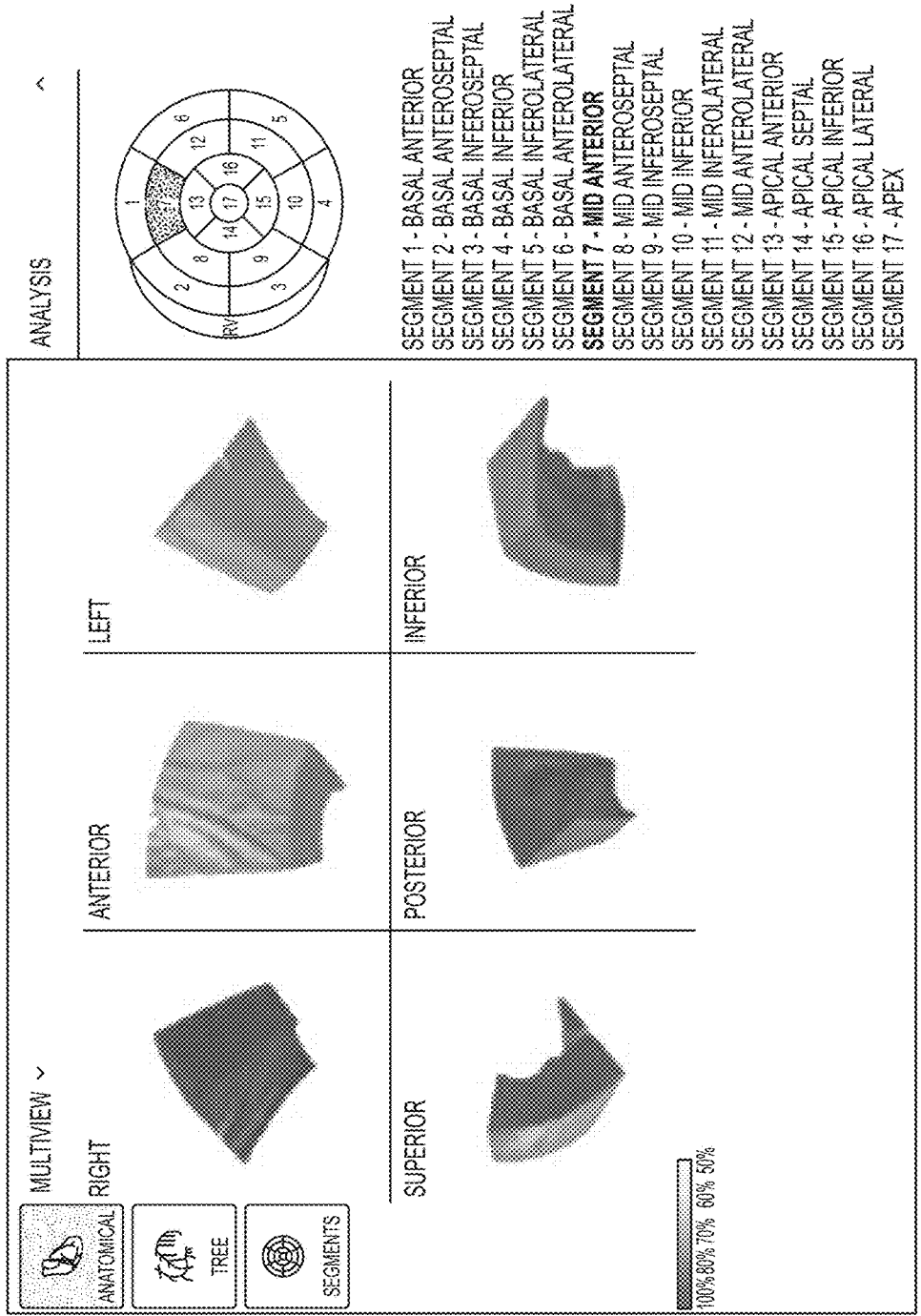
Figure 6H:
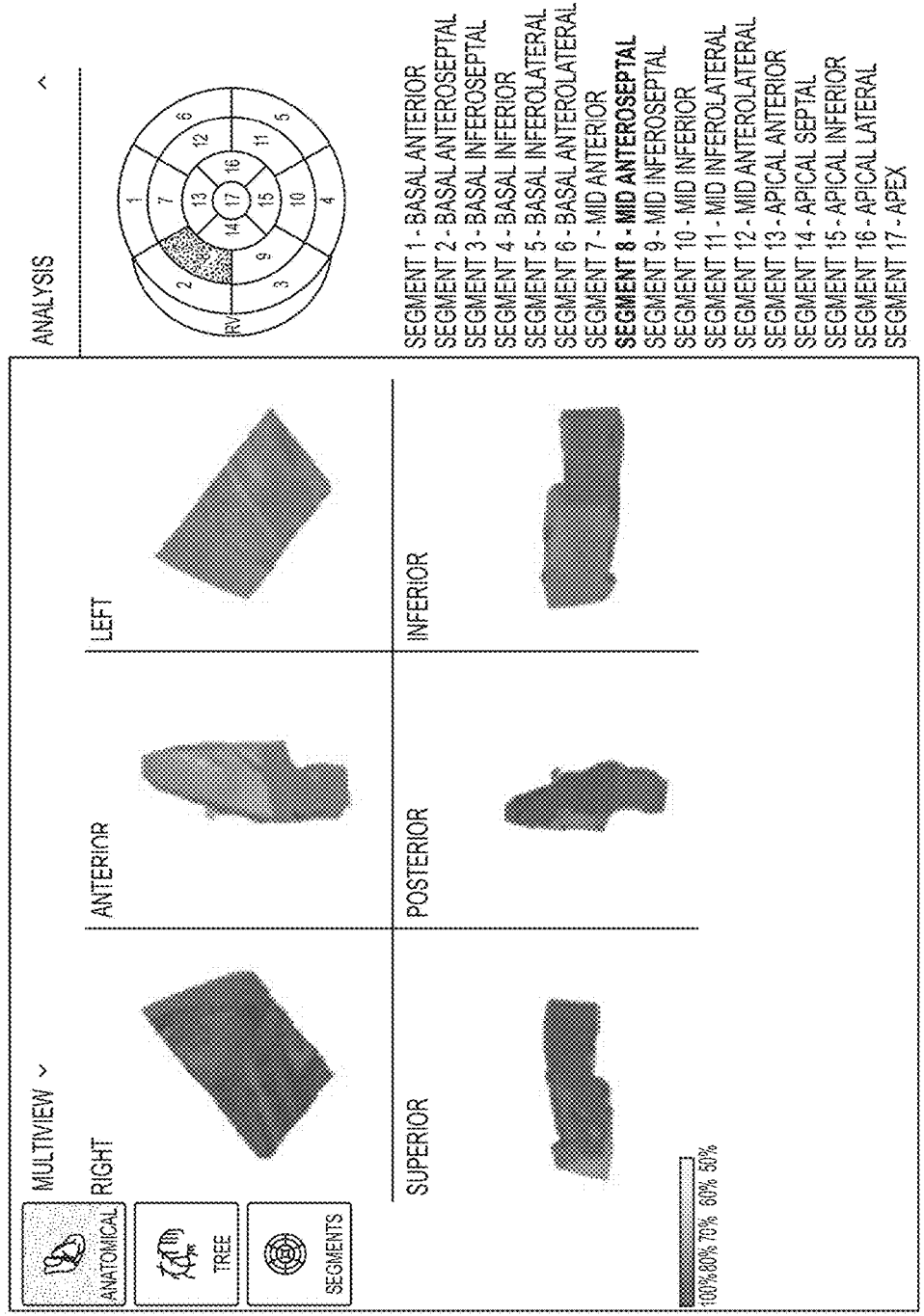
Figure 6I:
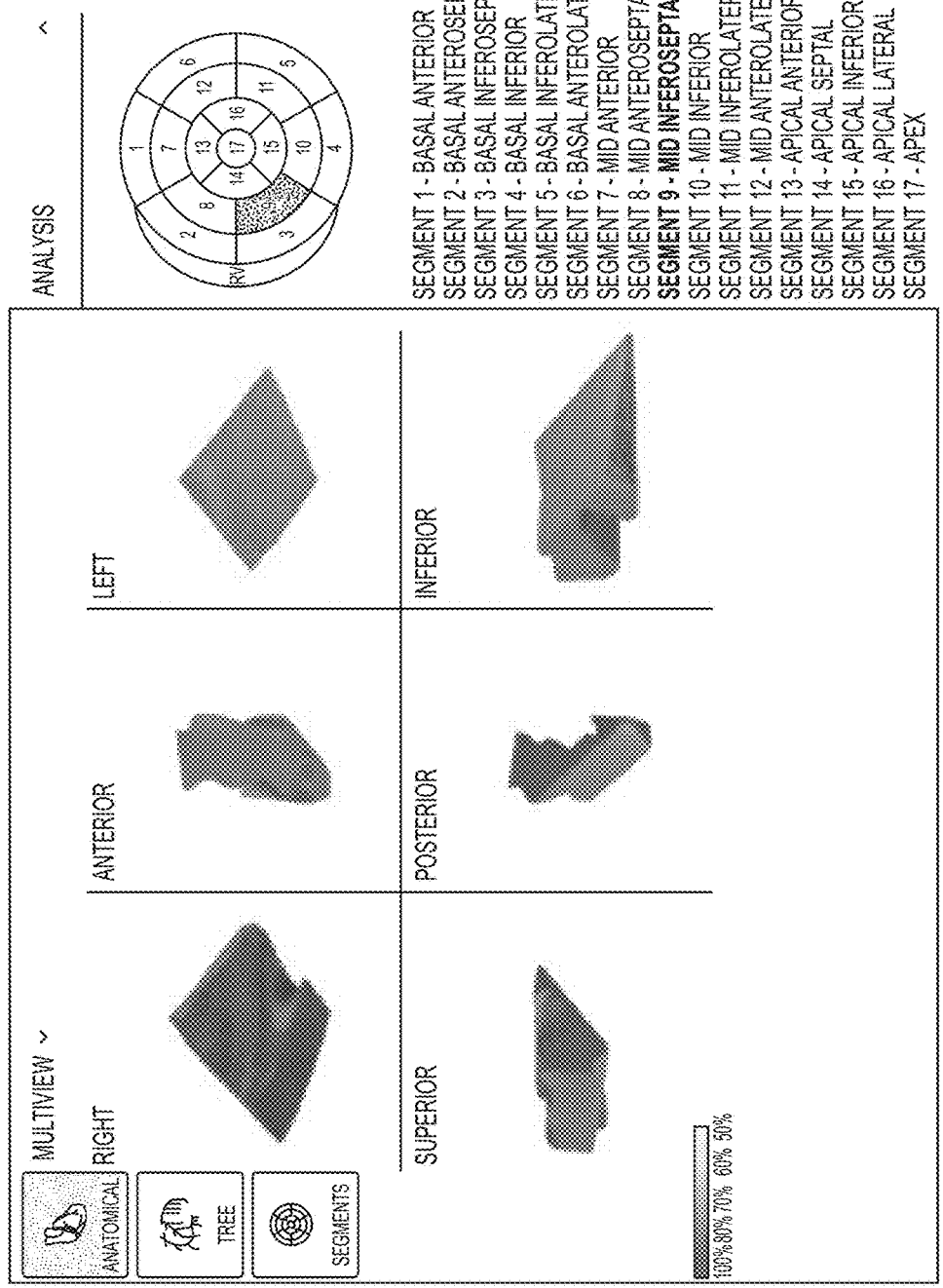
Figure 6J:
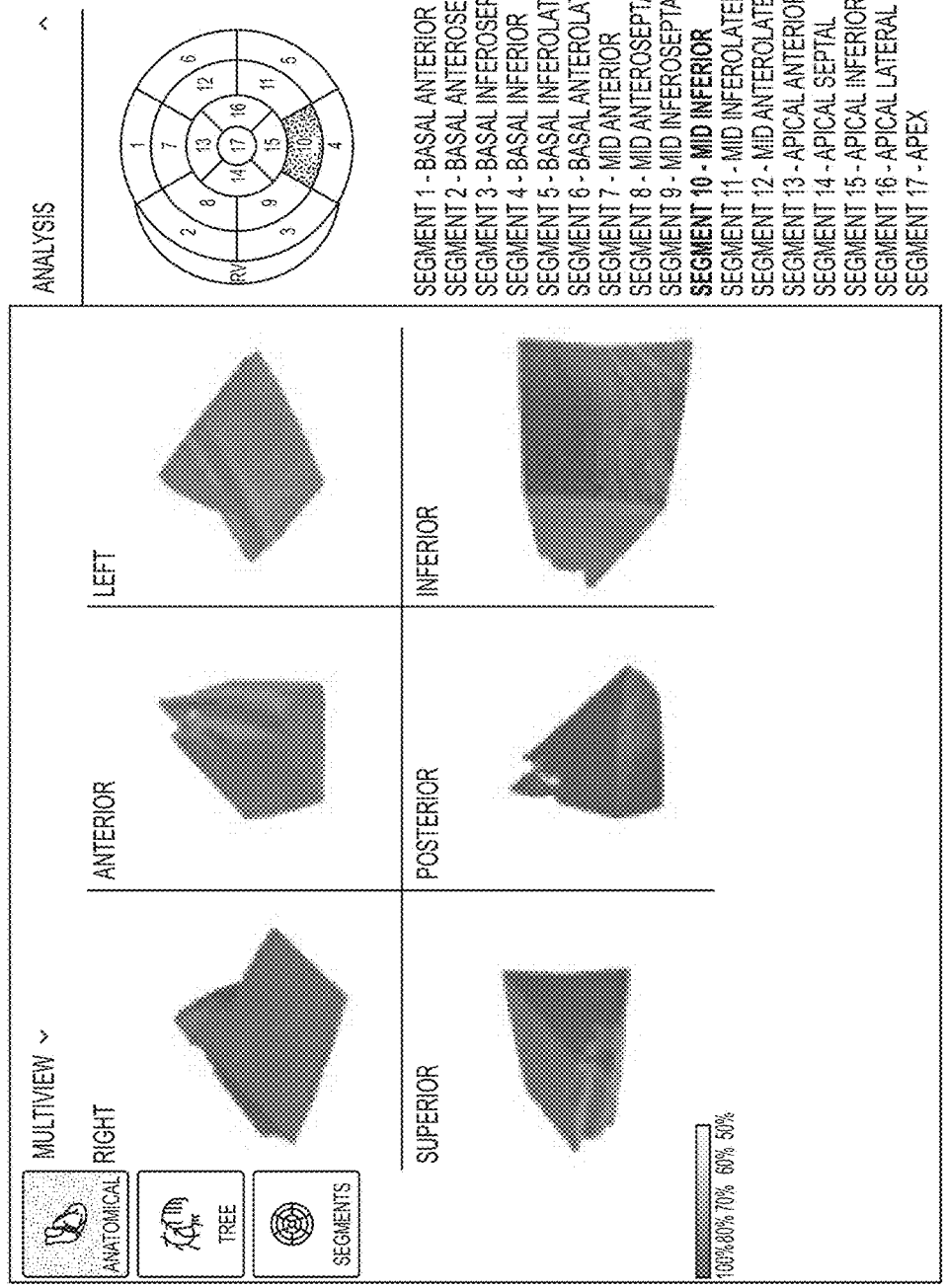
Figure 6K:
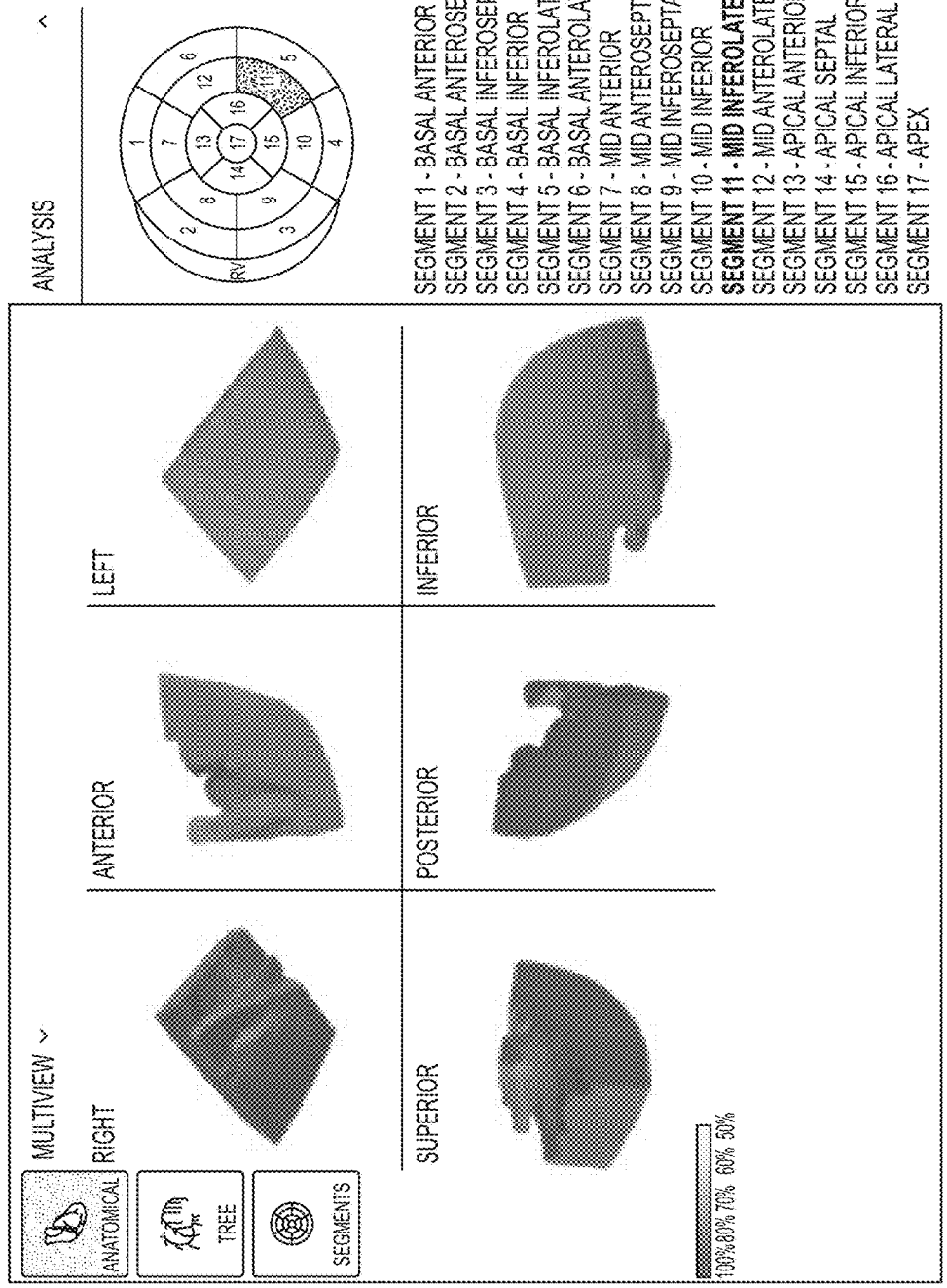
Figure 6L:
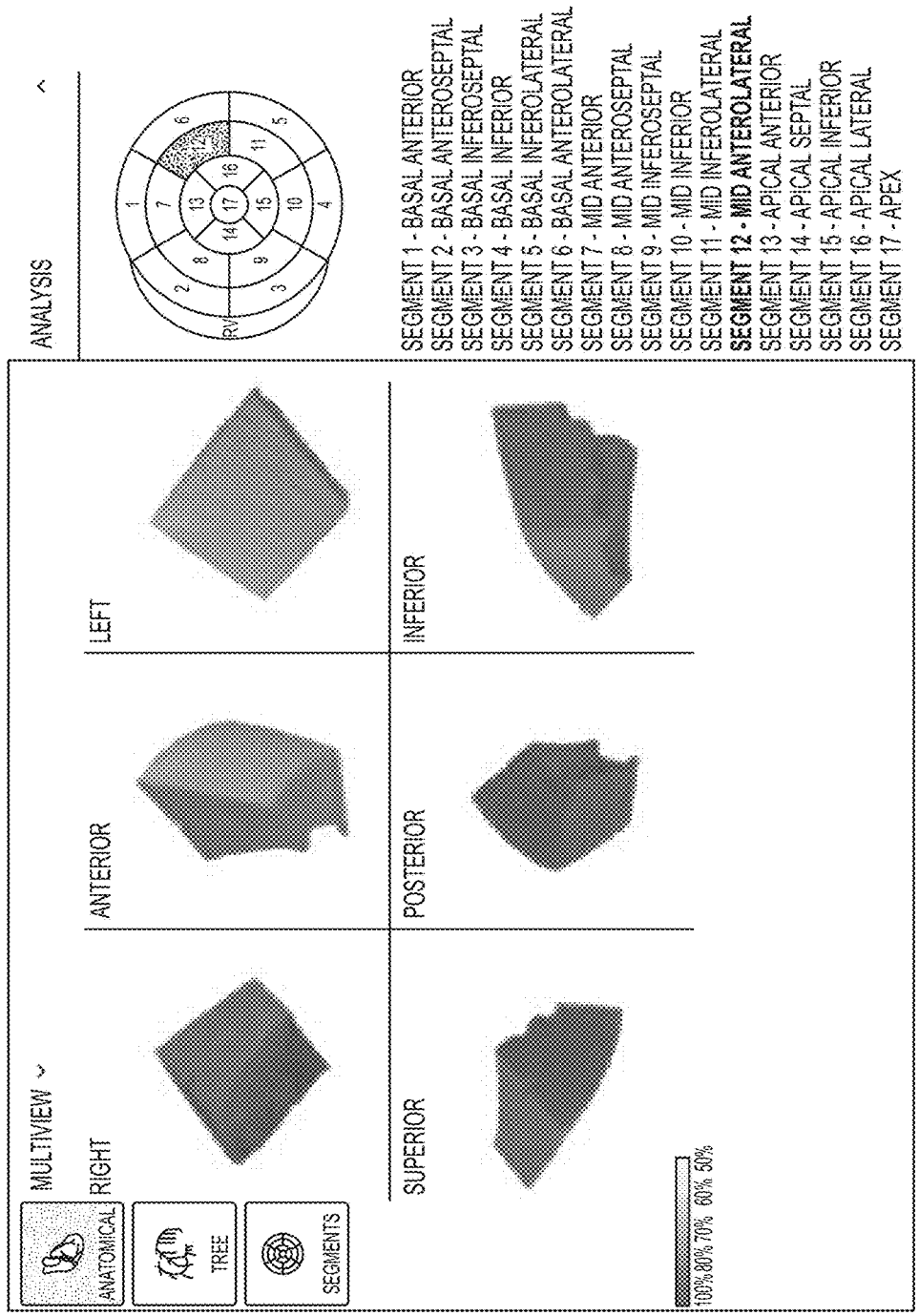
Figure 6M:
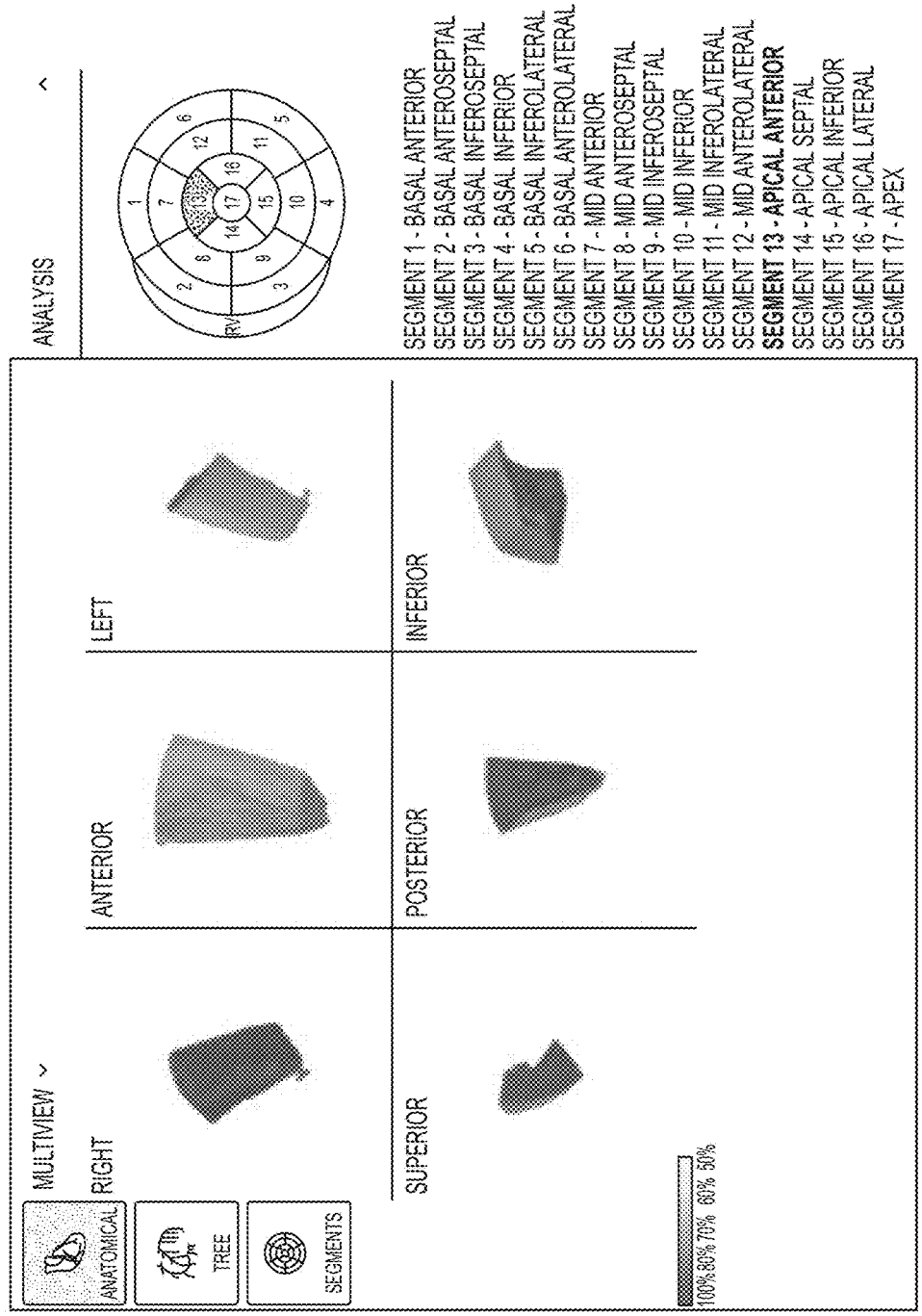
Figure 6N:
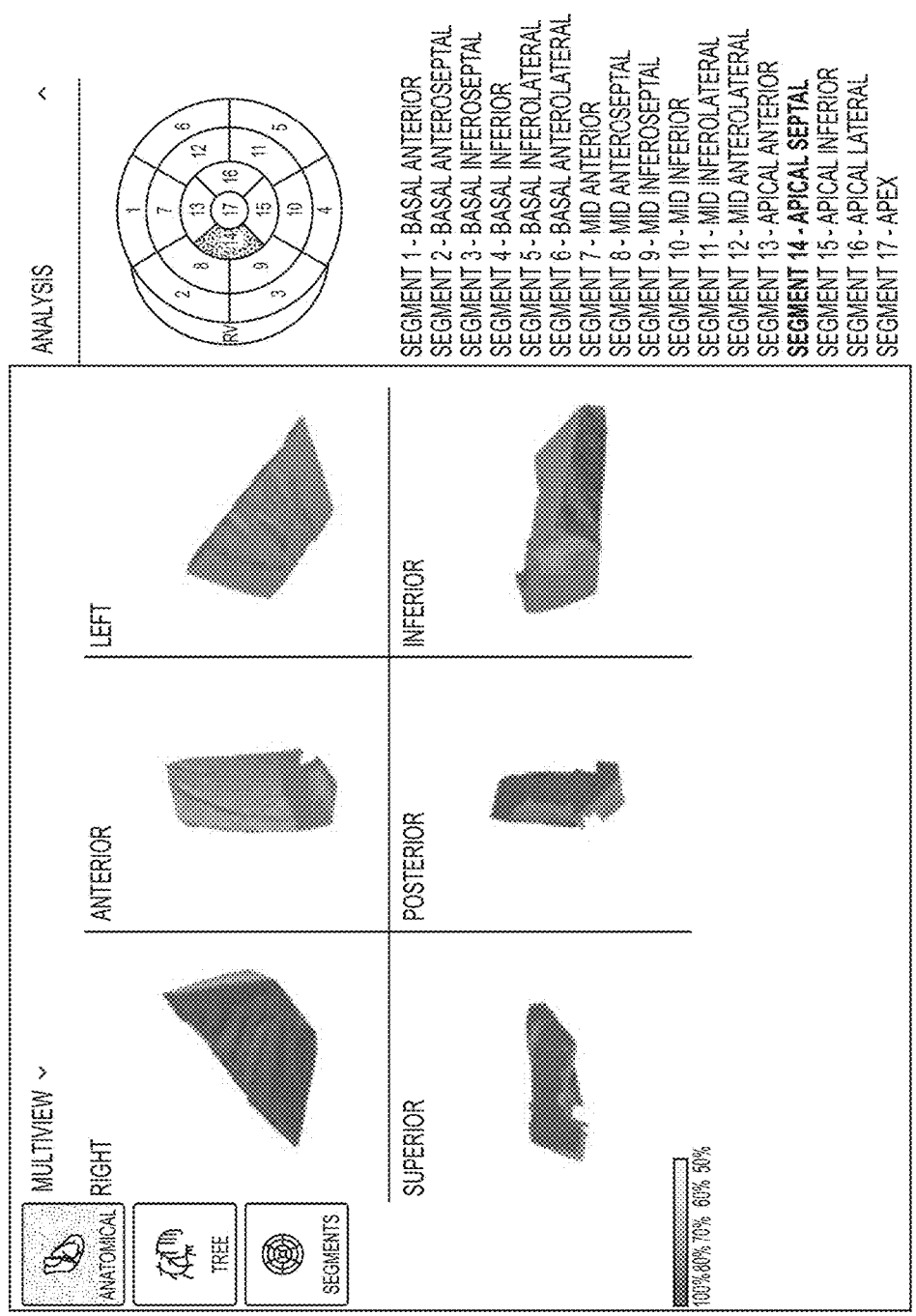
Figure 6O:
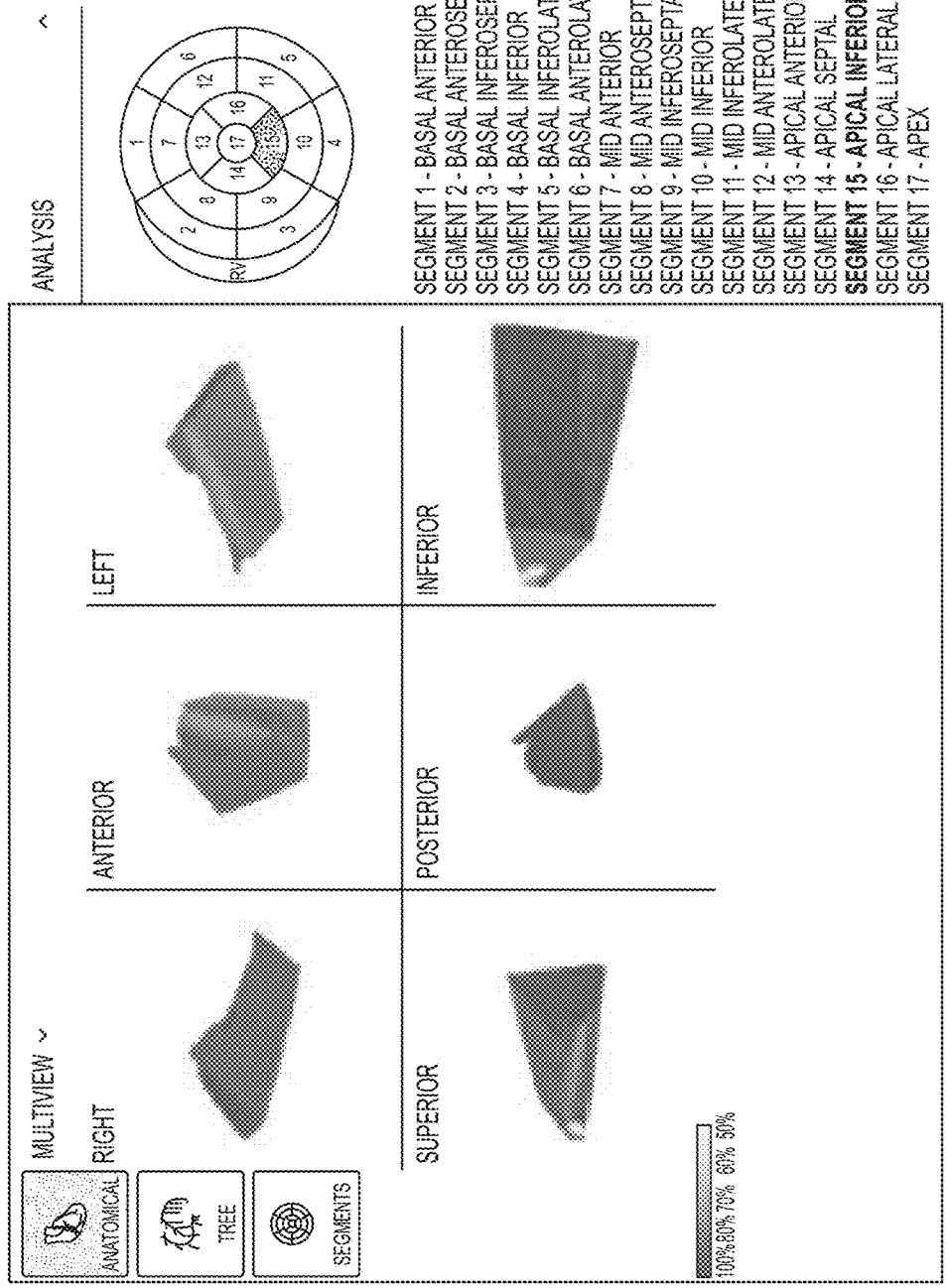
Figure 6P:
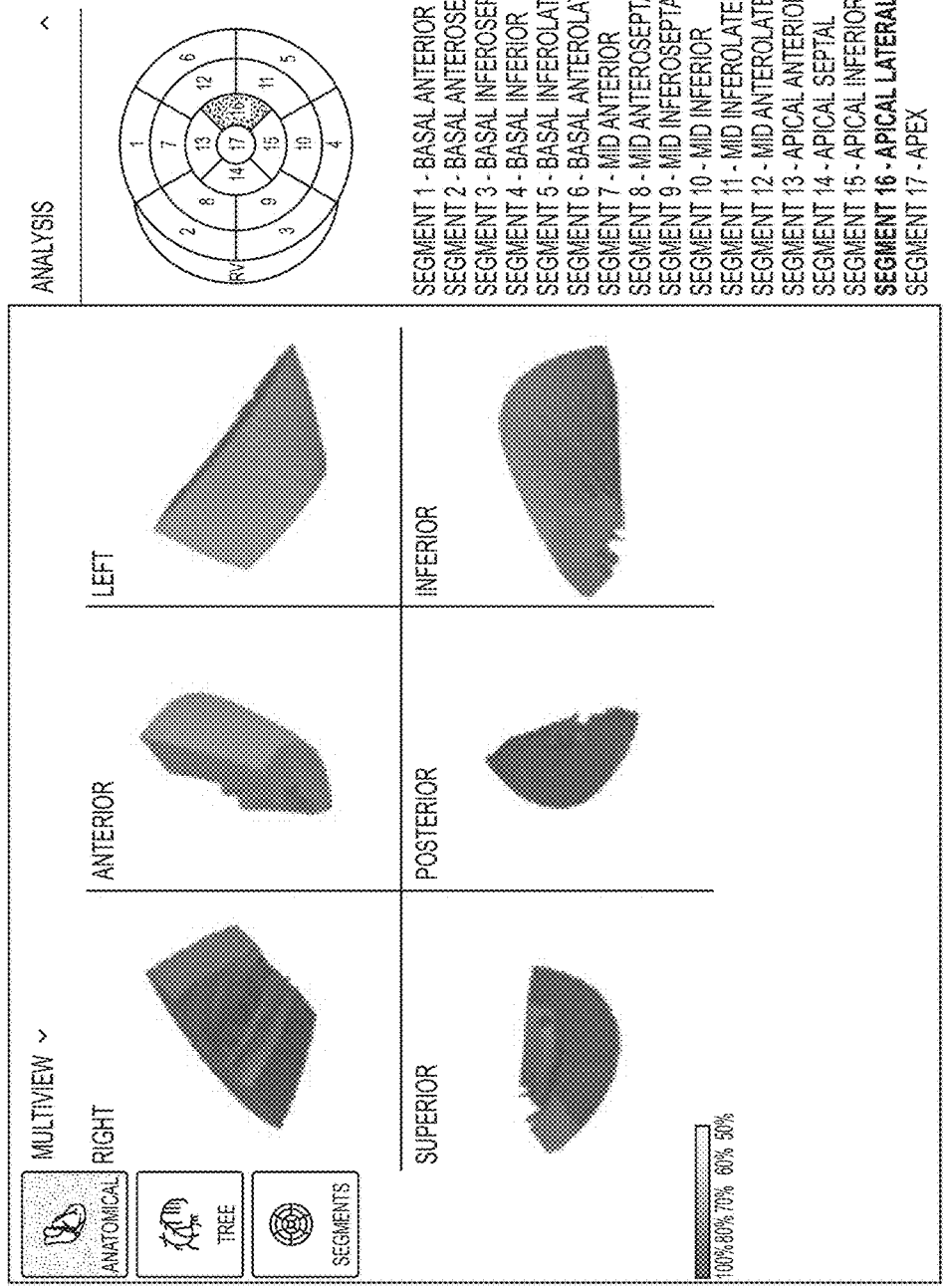
Figure 6Q:
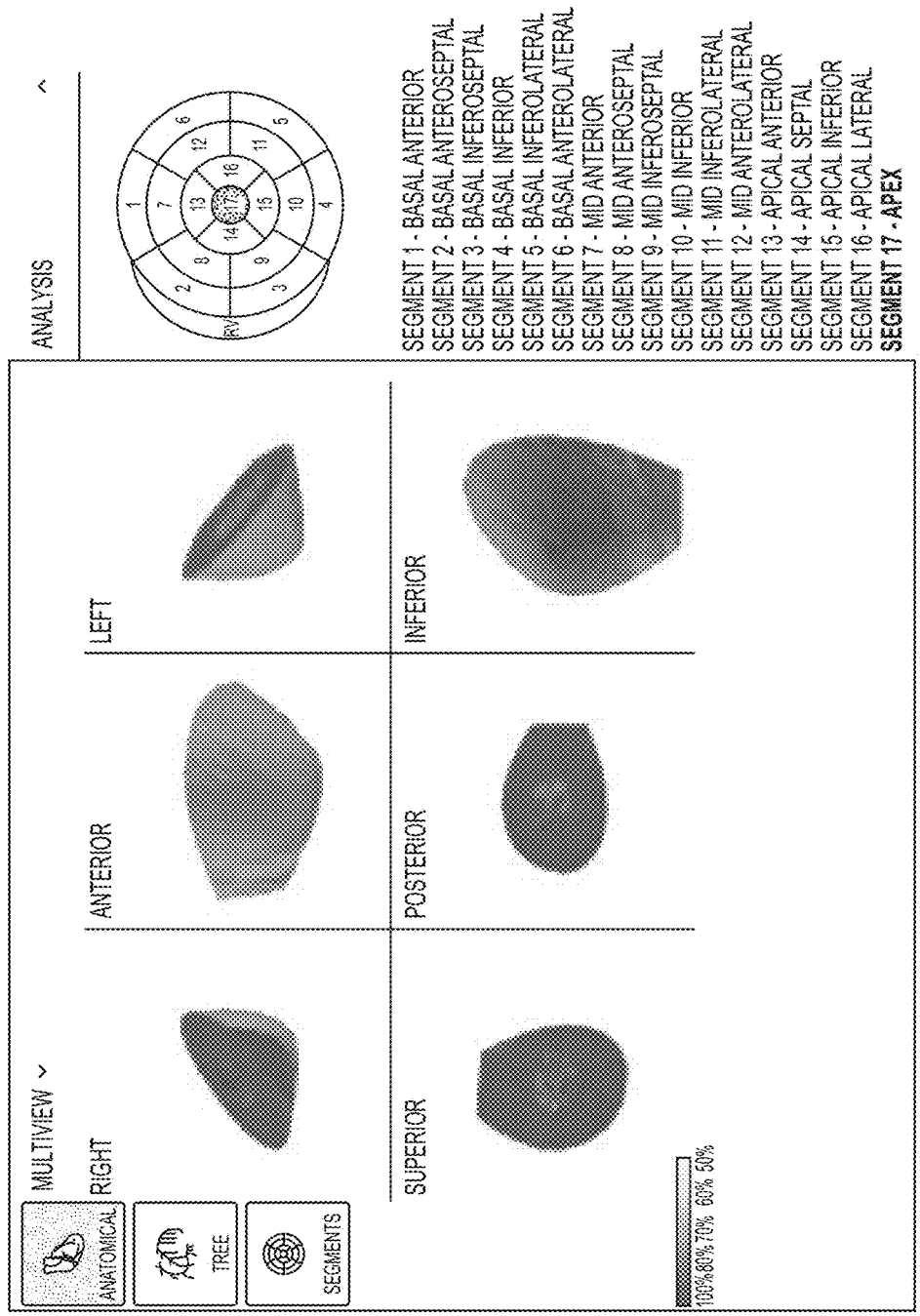

FIGS. 6A, 6B, 6C, 6D, 6E, 6F, 6G, 6H, 6I, 6J, 6K, 6L, 6M, 6N, 6O, 6P, and 6Q each shows different views of each three-dimensional tomographic model of the 17 segments of FIGS. 5B, 5C, 5D, and 5E in accordance with an illustrative embodiment. As shown, FIG. 6A shows a right view, an anterior view, a left view, a superior view, a posterior view, and an interior view of segment "1" corresponding to the basal anterior segment. FIG. 6B shows a right view, an anterior view, a left view, a superior view, a posterior view, and an interior view of segment "2" corresponding to the basal anteroseptal segment. FIG. 6C shows a right view, an anterior view, a left view, a superior view, a posterior view, and an interior view of segment "3" corresponding to the basal inferoseptal. FIG. 6D shows a right view, an anterior view, a left view, a superior view, a posterior view, and an interior view of segment "4" corresponding to the basal inferior segment. FIG. 6E shows a right view, an anterior view, a left view, a superior view, a posterior view, and an interior view of segment "5" corresponding to the basal inferolateral segment. FIG. 6F shows a right view, an anterior view, a left view, a superior view, a posterior view, and an interior view of segment "6" corresponding to the basal anterolateral segment. FIG. 6G shows a right view, an anterior view, a left view, a superior view, a posterior view, and an interior view of segment "7" corresponding to the mid anterior segment. FIG. 6H shows a right view, an anterior view, a left view, a superior view, a posterior view, and an interior view of segment "8" corresponding to the mid anteroseptal segment. FIG. 6I shows a right view, an anterior view, a left view, a superior view, a posterior view, and an interior view of segment "9" corresponding to the mid inferoseptal segment. FIG. 6J shows a right view, an anterior view, a left view, a superior view, a posterior view, and an interior view of segment "10" corresponding to the mid inferior segment. FIG. 6K shows a right view, an anterior view, a left view, a superior view, a posterior view, and an interior view of segment "11" corresponding to the mid inferolateral segment. FIG. 6L shows a right view, an anterior view, a left view, a superior view, a posterior view, and an interior view of segment "12" corresponding to the mid anterolateral segment. FIG. 6M shows a right view, an anterior view, a left view, a superior view, a posterior view, and an interior view of segment "13" corresponding to the apical anterior segment. FIG. 6N shows a right view, an anterior view, a left view, a superior view, a posterior view, and an interior view of segment "14" corresponding to the apical septal segment. FIG. 6O shows a right view, an anterior view, a left view, a superior view, a posterior view, and an interior view of segment "15" corresponding to the apical inferior segment. FIG. 6P shows a right view, an anterior view, a left view, a superior view, a posterior view, and an interior view of segment "16" corresponding to the apical lateral segment. FIG. 6Q shows a right view, an anterior view, a left view, a superior view, a posterior view, and an interior view of segment "17" corresponding to the apex segment.

Exemplary Healthcare Provider Portal

As noted in the discussion of FIG. 1, available cardiac assessment studies for a given patient can be presented in graphical user interface 100.

Figure 7:
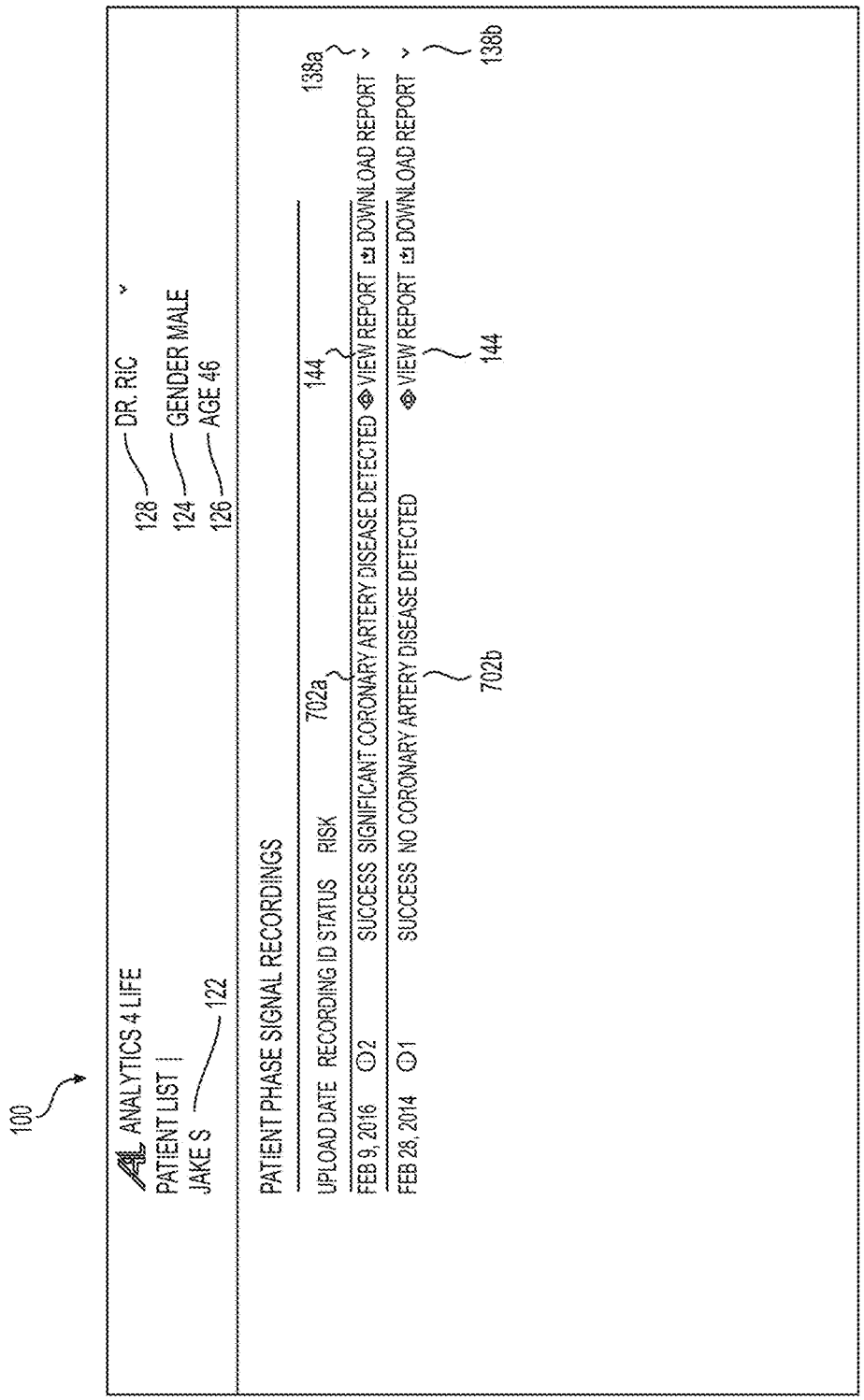
FIG. 7 illustrates the graphical user interface that includes a summary view of multiple data sets associated with a given patient in accordance with an illustrative embodiment.

FIG. 7 illustrates an embodiment of the graphical user interface 100 with a summary view of multiple studies available for viewing for a given patient (e.g., whose data set is associated with FIG. 2) in accordance with an illustrative embodiment. As shown in the embodiment of FIG. 7, the graphical user interface 100 is configured to present patient data such as the patient name 122, the patient gender 124, and the patient age 126. It is contemplated that other patient data may be presented, e.g., smoking history, family history, among others factors available in the patient file. In FIG. 7, the embodiment of the graphical user interface 100 further includes the medical record data such as a clinician identifier 128 (e.g., a doctor or clinician logged into a web portal that provides the graphical user interface 100). In FIG. 7, the embodiment of the graphical user interface 100 includes graphical widgets (shown as 136a and 136b) to facilitate downloading and/or saving of a corresponding report (e.g., report 400 shown and described in relation to FIGS. 4A, 4B, and 4C) and graphical widgets 144 to facilitate viewing of such reports 400.

Figure 8:
FIG. 8 illustrates a graphical user 800 of a web portal in accordance with another illustrative embodiment.

FIG. 8 illustrates another page of the graphical user interface 100 to display a list 802 of patients whose records are accessible by a given doctor or client logged into the healthcare provider portal. As shown in the embodiment of FIG. 8, the list 802 of patients include those (shown as 804) whose records are presented and discussed in relation to FIGS. 1-3. In some embodiments, the graphical user interface 800 includes a risk identifier 806 that connote patients with risk of significant coronary artery disease. As discussed above, other means of patient identification may be used, for example, the patient's hospital identification number.

Exemplary Detailed Visualization

Figure 9:
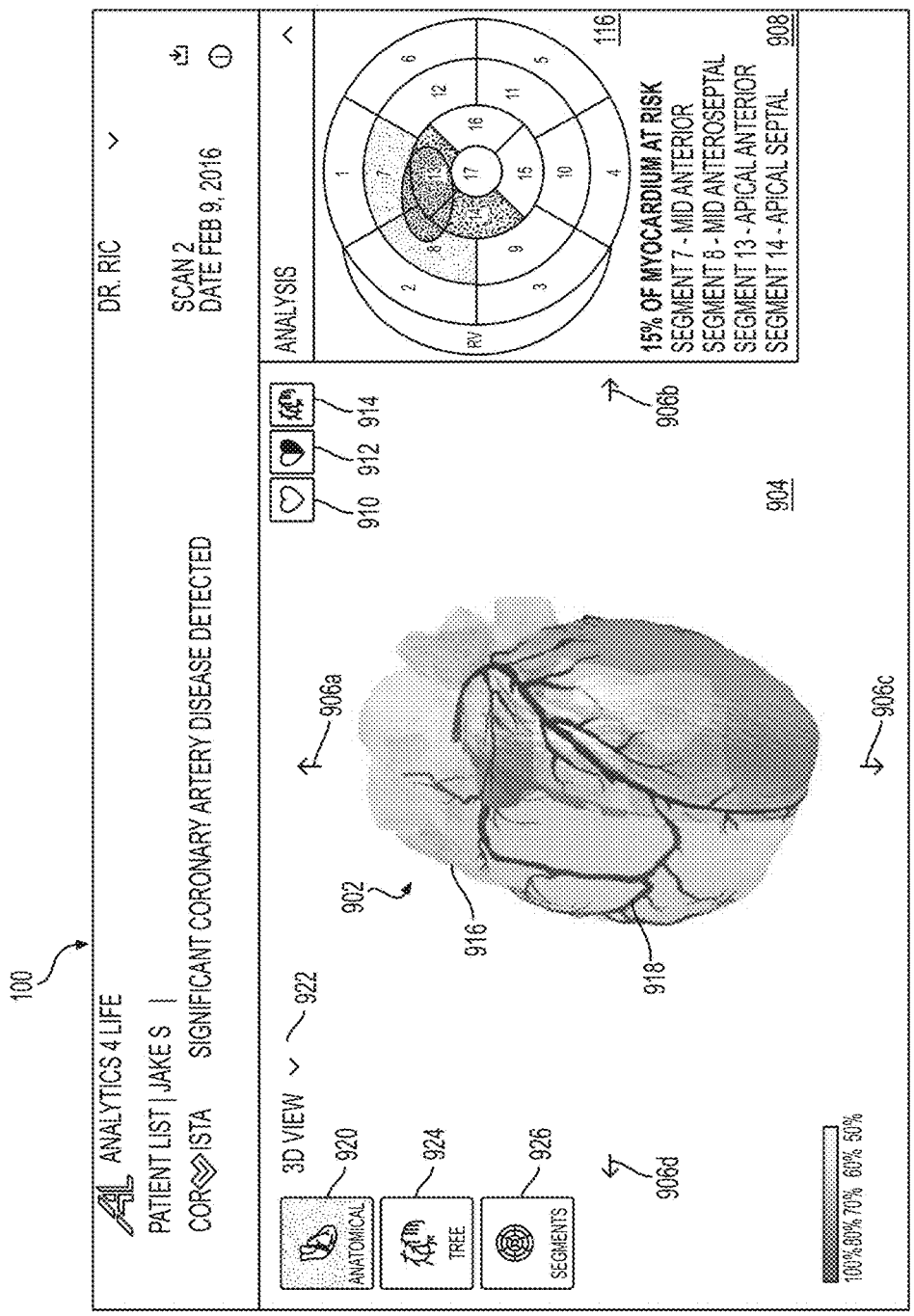
FIG. 9 shows the graphical user interface presenting a depiction of the rotatable three-dimensional anatomical model in a detailed-view workspace in accordance with an illustrative embodiment.

In another aspect of the graphical user interface, FIGS. 9-17 provide detailed visualization of various aspects of the report. Specifically, FIG. 9 shows an embodiment of the graphical user interface 100 presenting a depiction of a rotatable three-dimensional anatomical model 902 in a detailed-view workspace 904 in accordance with an illustrative embodiment. The detailed-view workspace 904 allows the rotatable three-dimensional anatomical model 902, or depictions thereof, to be rotated, via buttons 906a, 906b, 906c, 906d, to review detail structures of the segments and arteries of interest. In some embodiments, the rotatable three-dimensional anatomical model 902, or depictions thereof, is rotatable based on pre-defined short-cut keys of the keyboard keys and/or buttons of an input device (e.g., mouse). In some embodiments, the rotatable three-dimensional anatomical model 902 can be panned and/or zoomed based on pre-defined short-cut keyboard keys and input device inputs.

In this view, the corresponding two-dimensional 17-segment view 116 is concurrently presented in pane 908. In some embodiments, a selection of a segment in the two-dimensional 17-segment view 116 in pane 908 causes an embodiment of the graphical user interface 100 to rotate the three-dimensional anatomical model 902 to a pre-defined perspective view associated with the segment.

To provide alternative visualization of the myocardium segments and arteries of interest, embodiments of the graphical user interface 100 provides for widgets 910, 912, and 914 to adjust the rendered elements of the model. Widget 910 allows for rendering and presenting of the partially transparent overlay 916 of the complete heart to be disabled and/or enabled. Widget 912 allows for rendering and presenting of the right side of the heart model and the left side of the heart model to be toggled. To this end, embodiments of the graphical user interface 100 can present depictions of the model 902 with only the three-dimensional objects associated with the left-side segments of the heart model presented, or both the left-side segments and the right-side segments of the heart model presented, or no segments of the heart model presented. Widget 914 allows for the rendering and presenting of the coronary vessels 918 to be disabled and/or enabled. The detailed-view workspace 904 can be accessed by widget 920. In some embodiments, the detailed-view workspace 904 is assessed by selecting a widget 148 for the detailed 3D view (as, for example, shown in FIG. 1).

Figure 10:
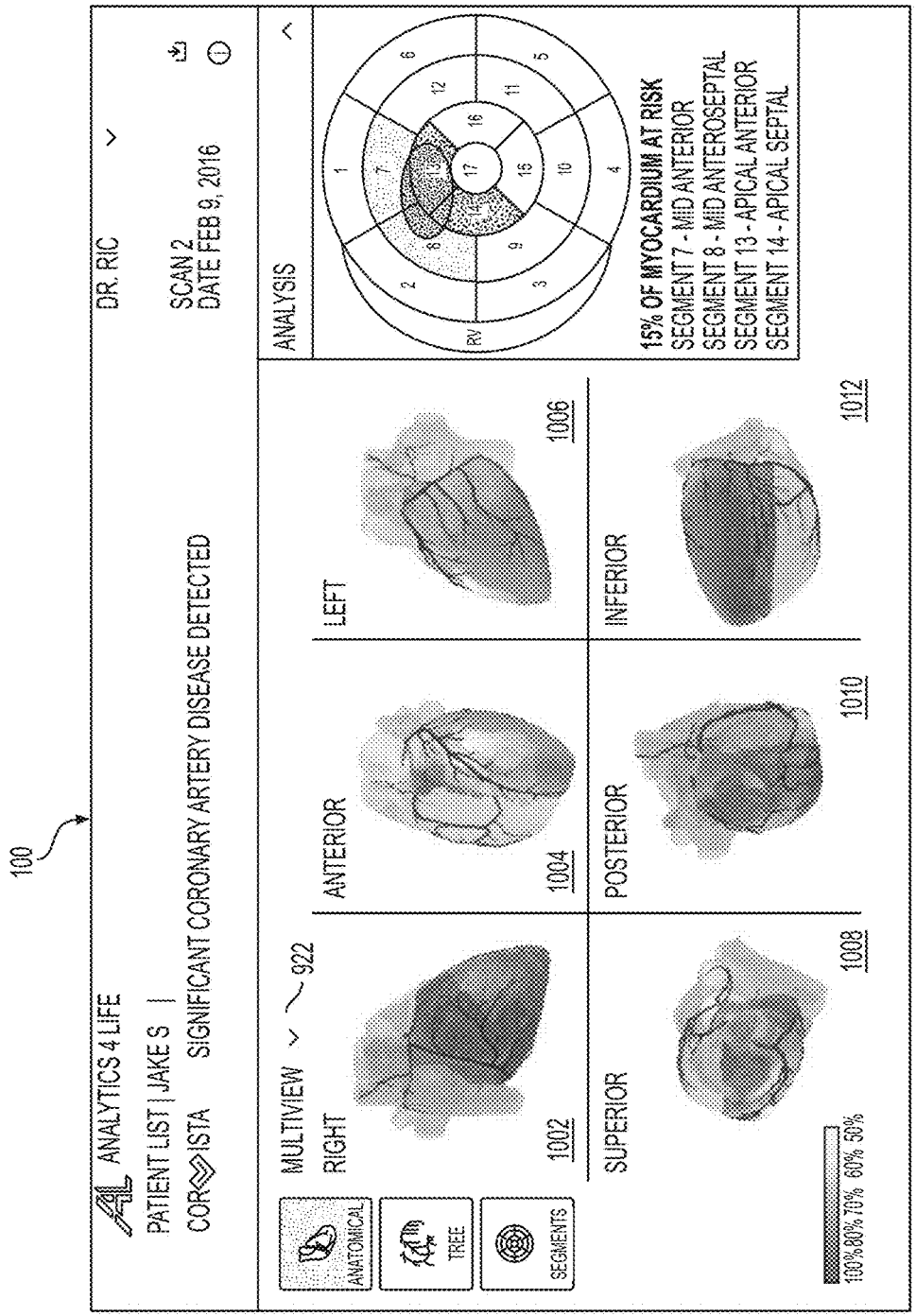
FIG. 10 shows a multiple view presentation of a depiction of the model of FIG. 9 in accordance with an illustrative embodiment.

Embodiment of the graphical user interface 100, in some embodiments, allows multiple pre-defined presentation views of depictions of the model 902 to be presented in the detailed-view workspace 904. FIG. 10 shows a multiple view presentation of the model 902 of FIG. 9 in accordance with an illustrative embodiment. As shown in the embodiment of FIG. 10, the graphical user interface 100 includes a right view (in pane 1002), an anterior view (in pane 1004), a left view (in pane 1006), a superior view (in pane 1008), a posterior view (in pane 1010), and a posterior view (in pane 1012) of the model 902. In FIGS. 9 and 10, the graphical user interface 100 includes widget 922 to allow the user to select between the single model view (as shown in the embodiment of FIG. 9) and the multiple model views (as shown in the embodiment of FIG. 10).

Figure 11:
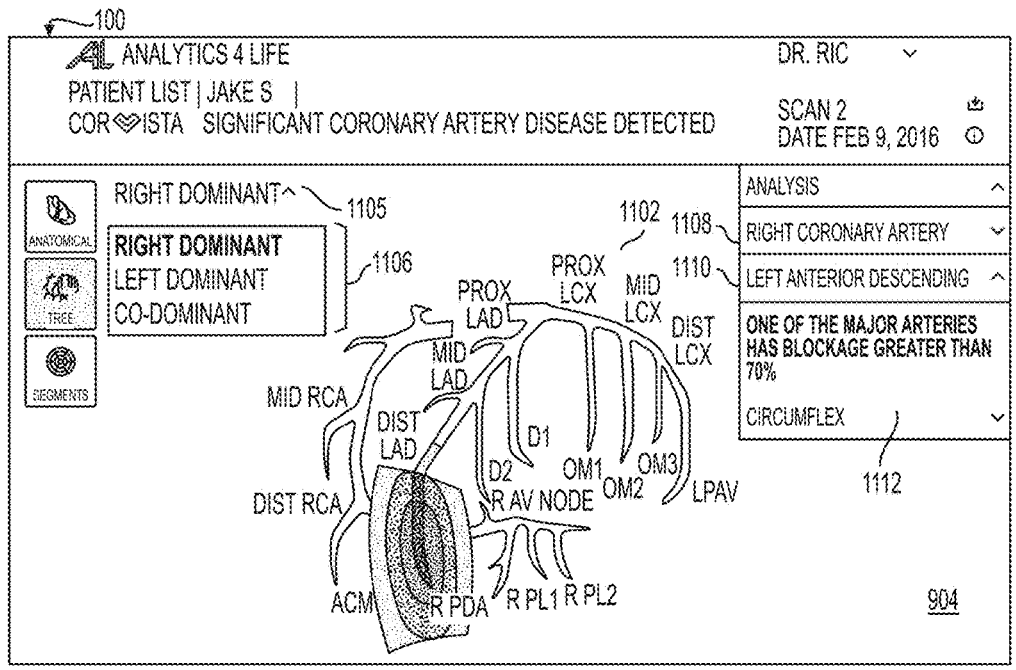
FIG. 11 shows a depiction of the two-dimensional view of the major coronary with emphasis and/or perspective from the right dominant side of the heart in accordance with an illustrative embodiment.
Figure 12:
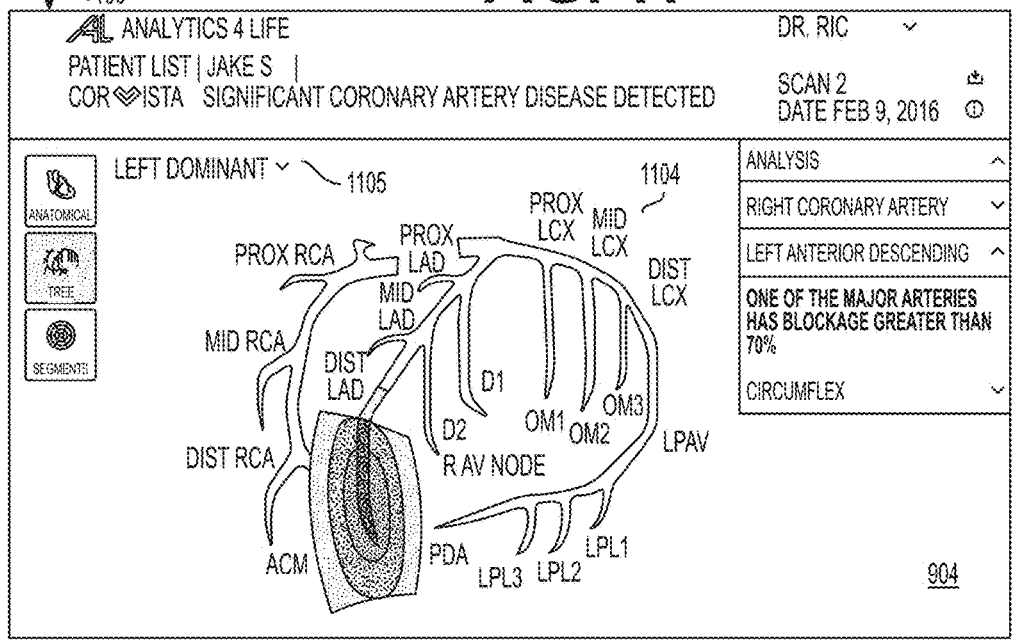
FIG. 12 shows a depiction of a two-dimensional view of the major coronary with emphasis and/or perspective from the left dominant side of the heart in accordance with an illustrative embodiment.
Figure 13:
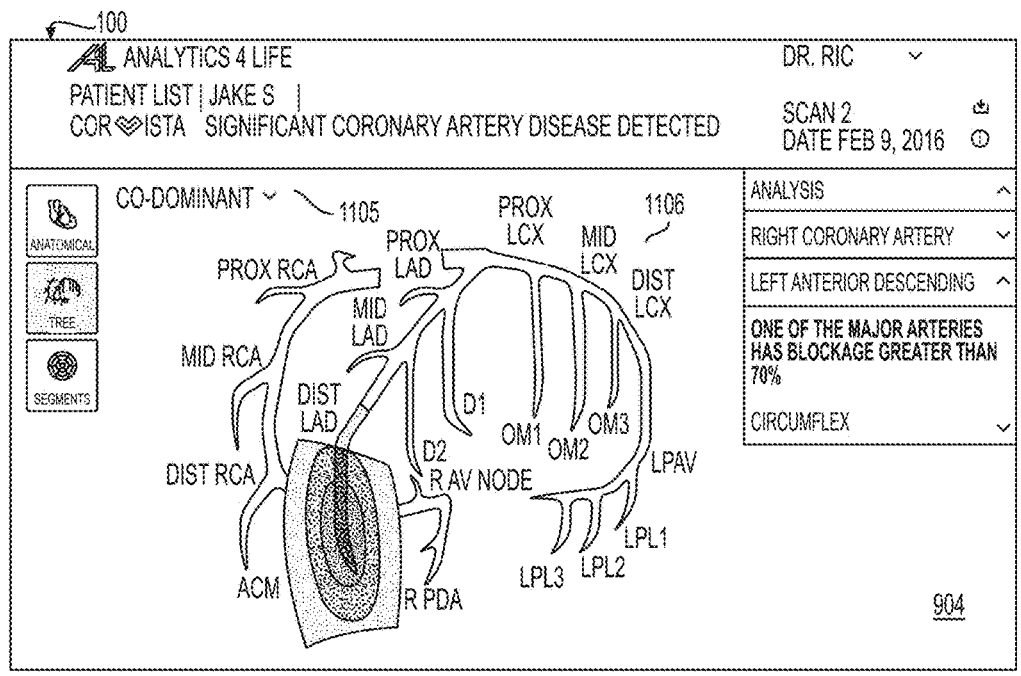
FIG. 13 show a depiction of a two-dimensional view of the major coronary that is do-dominant in accordance with an illustrative embodiment.

FIGS. 11-13 shows an embodiment of the graphical user interface 100 presenting depictions of the two-dimensional view of the major coronary artery 114 in the detailed-view workspace 904 in accordance with an illustrative embodiment. Specifically, FIG. 11 shows the two-dimensional view of the major coronary artery 114 (shown as 1102) with emphasis and/or perspective from the right dominant side of the heart in accordance with an illustrative embodiment. FIG. 12 shows the two-dimensional view of the major coronary artery 114 (shown as 1104) with emphasis and/or perspective from the left dominant side of the heart in accordance with an illustrative embodiment. FIG. 13 show the two-dimensional view of the major coronary artery 114 (shown as 1106) that is do-dominant in accordance with an illustrative embodiment. The detailed-view workspace 904 can be accessed by widget 924 (for example, as shown in the embodiment of FIG. 9). The various views of the major coronary artery 114 can be selected via widget 1105. FIG. 11 shows a drop-down selection box 1106 that is presented when widget 1105 is selected The embodiment of the graphical user interface 100, as shown in the embodiment of FIG. 11, may present analysis specific to the right coronary artery (1108), the left anterior descending artery (1110), and the circumflex artery (1112).

Figure 14:
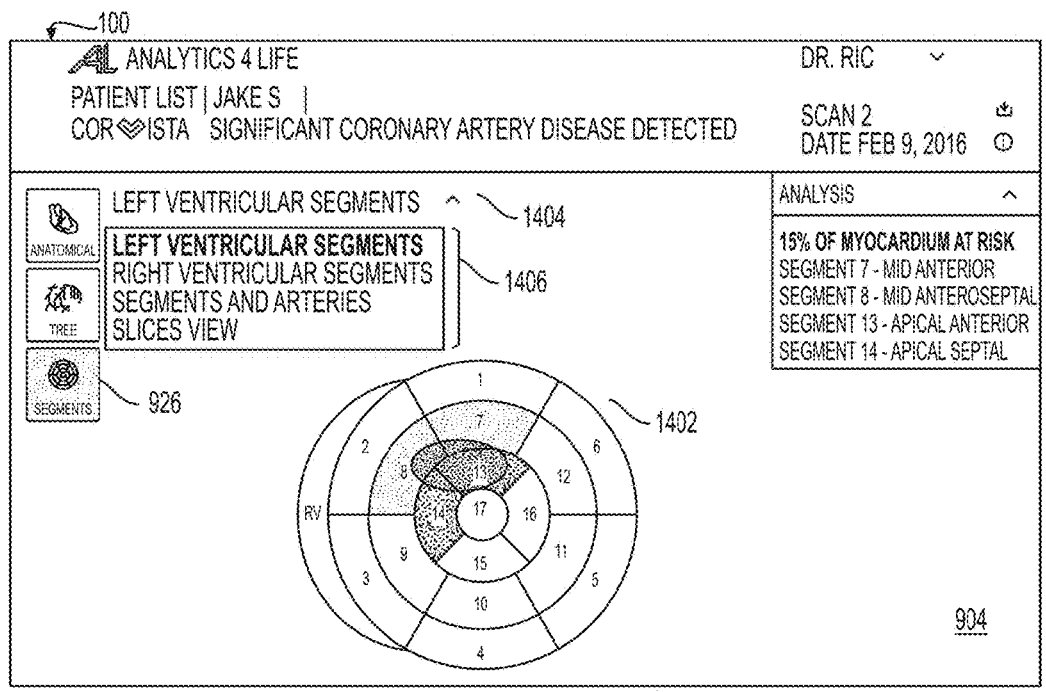
FIG. 14 shows a depiction of a two-dimensional 17-segment view of a left ventricular segment in accordance with an illustrative embodiment.
Figure 15:
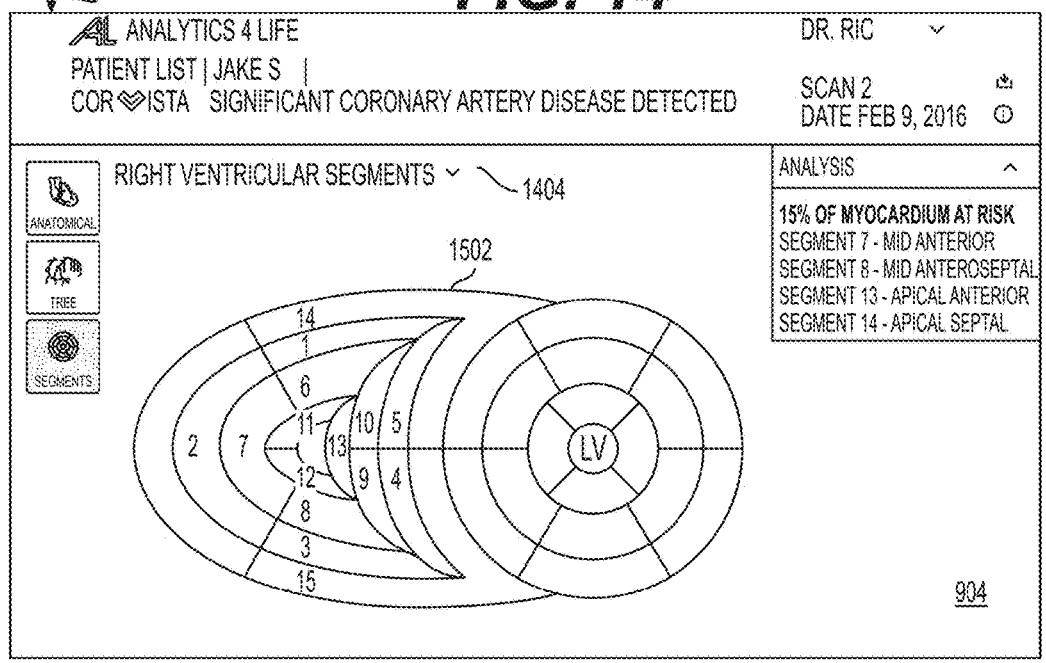
FIG. 15 shows a depiction of a two-dimensional 17-segment view of a right ventricular segment in accordance with an illustrative embodiment.
Figure 16:
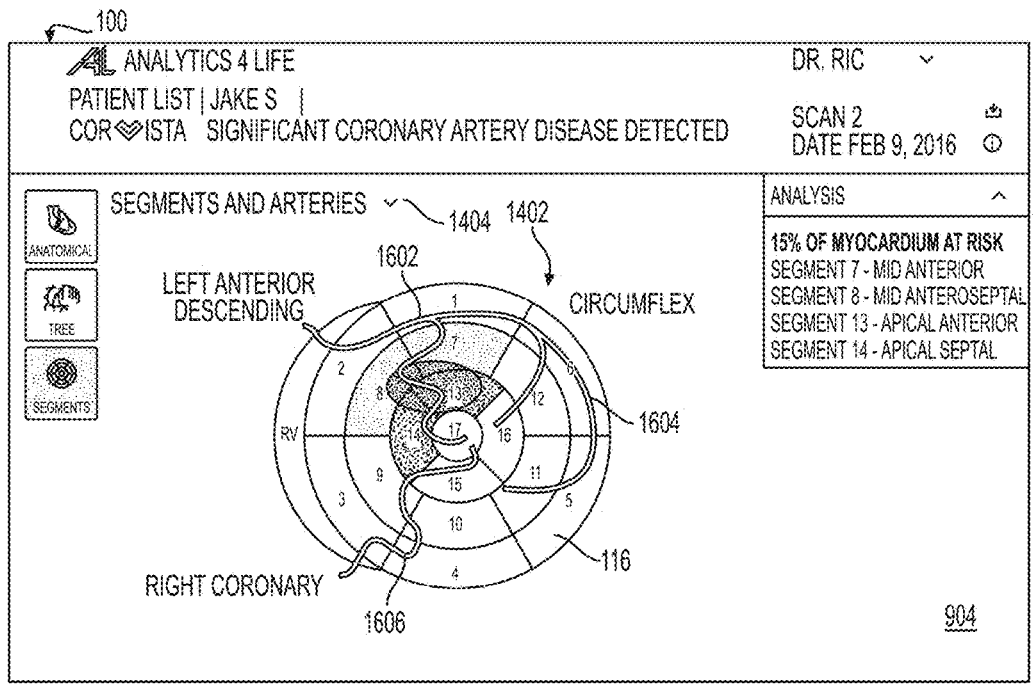
FIG. 16 shows a depiction of the left ventricular segment view overlaid with corresponding major arteries, as described in relation to FIG. 5A in accordance with an illustrative embodiment.

FIGS. 14-17 shows an embodiment of the graphical user interface 100 presenting the two-dimensional 17-segment view in the detailed-view workspace 904 in accordance with an illustrative embodiment. Specifically, FIG. 14 shows the two-dimensional 17-segment view 1402 of a left ventricular segment in accordance with an illustrative embodiment. FIG. 15 shows the two-dimensional 17-segment view 1502 of a right ventricular segment in accordance with an illustrative embodiment. In FIG. 16, the left ventricular segment view 1402 is shown overlaid with corresponding major arteries (shown as "Left Anterior Descending" artery 1602, "Circumflex" artery 1604, and "Right Coronary" artery 1606) mapped and/or overlaid over the segment, as described in relation to FIG. 5A in accordance with an illustrative embodiment. To this end, spatial locations for each given segment (e.g., those of 116) is projected and/or mapped to an anatomical rendering of the heart, and spatial locations of major arteries are projected and/or mapped in relation to the respective segments.

Figure 17:
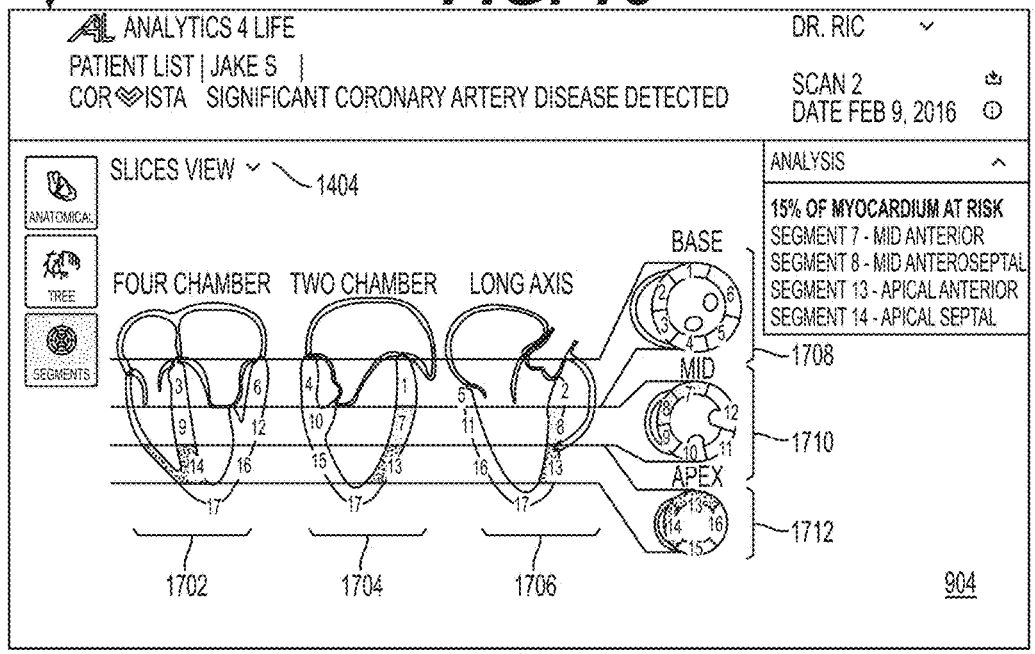
FIG. 17 shows a depiction of a two-dimensional slice view of the 17 segments in accordance with an illustrative embodiment

The two-dimensional 17-segment view 1402 can be accessed by widget 926 (for example, as shown in the embodiment of FIGS. 9 and 14). The various segment views can be selected via widget 1404. FIG. 14 shows a drop-down selection box 1406 that is presented for the views shown in FIGS. 14-17 when widget 1404 is selected FIG. 17 shows a two-dimensional slice view of the 17 segments in accordance with an illustrative embodiment. The slice view include a number of views of the heart, including a four chamber view (shown as "Four Chamber" 1702), a two chamber view (shown as "Two Chamber" 1704), and a long-axis view (shown as "Long-Axis 1706). The slice view further includes a number of views along a number of axial planes, including a base axial plane (shown as "Base" 1708), a mid-axial plane (shown as "Mid" 1710), and an apex axial plane (shown as "Apex" 1712).

It is noted that FIGS. 9-17 show visualizations of the same data set, which also correspond to the dataset shown and discussed in relation to FIG. 2. That is, as shown here, the same study data is shown among the different views in FIGS. 2 and 9-17.

In some embodiments, the report 400 includes all the views as discussed in relation to FIGS. 11-17.

Exemplary Visualizations of Blockage of Coronary Arteries

As described above, each of the depictions of the three-dimensional anatomical maps 108 and 110 and the two-dimensional view of the major coronary artery 114 in FIG. 2 shows blockages in three regions of the major arteries of the heart. The blockages may be shown as a pulsing animated sequence that varies in size and coloration that may correspond to, e.g., various pathologies of that portion of the heart (e.g. blockage and/or ischemic tissue) to varying degrees of severity.

FIGS. 18A and 18B illustrate an exemplary embodiment of a pulsing animated sequence in accordance with an illustrative embodiment. FIG. 18A shows an exemplary embodiment of a rendering of a beginning of the pulsing animated sequence. FIG. 18B shows an exemplary embodiment of a rendering of an end of the pulsing animated sequence. As shown in the embodiments of FIGS. 18A and 18B, an area 1802 corresponding the pulsing animated sequence varies in size and coloration that may correspond to, e.g., various pathologies of that portion of the heart (e.g. blockage and/or ischemic tissue) to varying degrees of severity.

Visualizations of Three-Dimensional Heart Model

As discussed above, the graphical user interface 100 can provide alternative visualization of the myocardium segments and arteries of interest in the rendered heart model.

Figure 19:
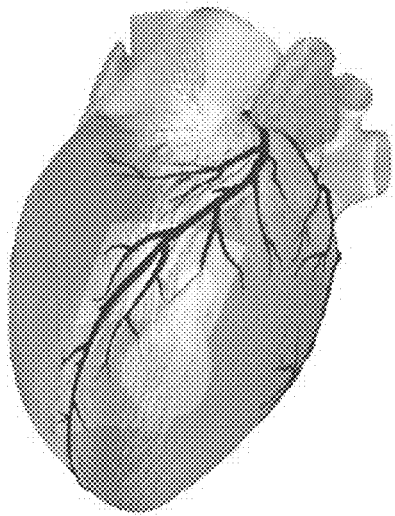
FIGS. 19, 20, and 21 each illustrates the alternative visualization of a depiction of the myocardium segments of the heart model in accordance with an illustrative embodiment.
Figure 20:
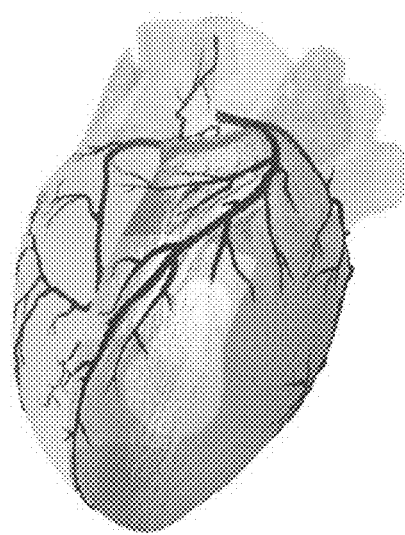
Figure 21:
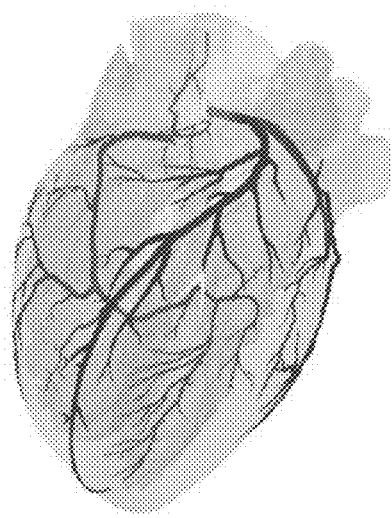

FIGS. 19-21 each illustrates the alternative visualization of the myocardium segments of the heart model in accordance with an illustrative embodiment. FIG. 19 shows both the left-side segments and the right-side segments of the heart model as discussed in relation to FIG. 9.

To this end, the graphical user interface 100 can present depictions of the model 902 with only the three-dimensional objects associated with the left-side segments of the heart model presented, or both the left-side segments and the right-side segments of the heart model presented, or no segments of the heart model presented. FIG. 20 shows a partial rendering in which only the left-side segments of the heart model is presented. That is, about half of an outside surface of the heart is shown with a higher degree of translucency to allow visualization into the inner tissues. FIG. 21 shows only the partially transparent tomographic representation of the complete heart (and the coronary arteries) and no left-side segments or right-side segments of the heart model. To this end, either separately or along with variations in size and coloration (in static depictions and/or pulsing heart animations) visualization into the inner tissues is further enhanced. It is noted that, in this view, the colorations associated with the blockage of the arteries are still shown.

Method of Operation

Figure 22:
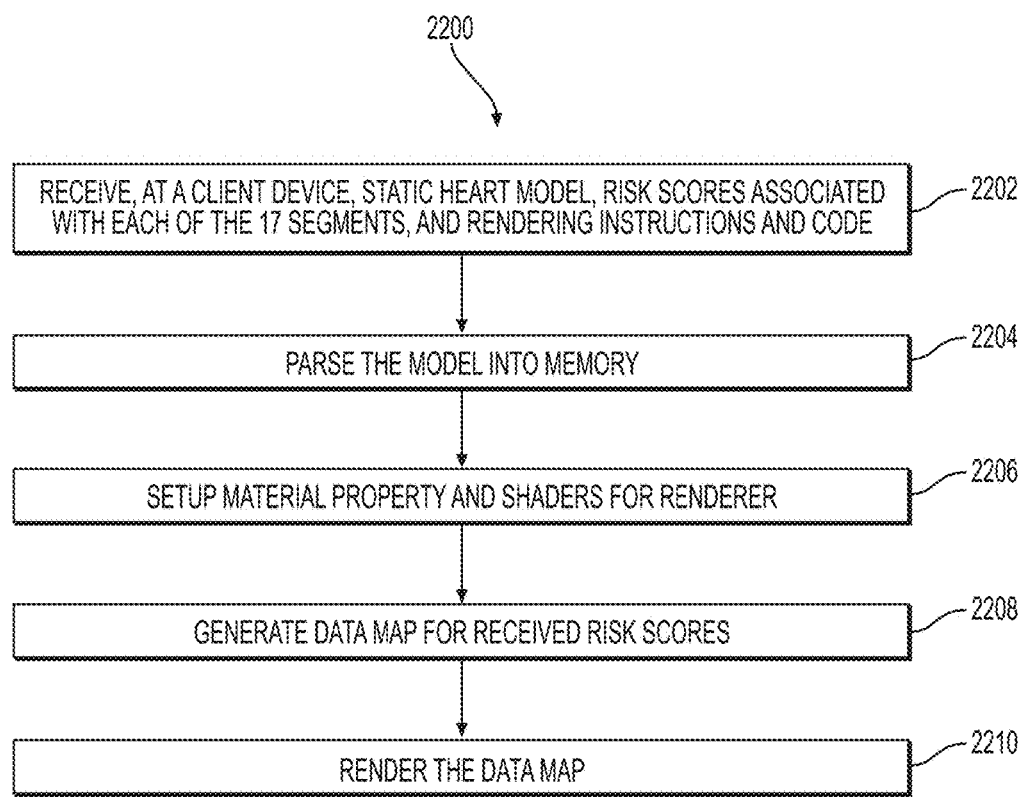
FIG. 22 is a flow diagram illustrating an exemplary method of rendering a depiction of the three-dimensional anatomical maps 106 in accordance with an illustrative embodiment.

FIG. 22 is a flow diagram illustrating a method of rendering the three-dimensional anatomical maps 106 in accordance with an illustrative embodiment. In some embodiments, the three-dimensional heart of the anatomical maps (e.g., 106) is a static heart model comprising 17 distinct meshes and texture images that correspond to each of the 17 segments of the left ventricle. Each of the mesh, in some embodiments, includes a grouping tree of the part elements in the mesh. In some embodiments, the distinct meshes and texture images are formatted in ThreeJS. Other WebGL framework can be also used.

The rendering pipeline for the heart model includes receiving (2202), at a client device, the ThreeJS static heart model, risk scores associated each of the 17 segments, and rendering instructions and code. In some embodiments, the ThreeJS static heart model are transmitted as an encrypted file. Upon receiving at a client device, the ThreeJS static heart model, the client device is configured to decode the model files associated with the ThreeJS static heart model and parse (2204) the static model files, e.g., into ThreeJS objects, in a browser memory.

The client device, in some embodiments, when executing the instruction code, configures (2206) the material properties of the surfaces of the parsed ThreeJS objects. The client device, in some embodiments, then setup the shaders. In some embodiments, the client device, when executing the instruction code, registers a vertex shader and a fragment shader to the ThreeJS renderer. The vertex shader and fragment shader modifies the color of each of the segmented model files based on the received risk scores. For example, the vertex shader and fragment shader is adjusted to generate varying colors between yellow and red based on received risk scores in the ranges between 0.5 and 1.0.

In some embodiments, the client device generates (2208) a data map for the risk score by interprets and maps the risk scores as colors onto the 17 segments in the client's memory. The client device then renders (2210) the data map. In some embodiments, the client device renders the data map by performing a series of steps defined by the ThreeJS WebGL renderer that handles the actual rendering of the parsed objects onto the client's browser, including setting up a scene, setting up and position the virtual cameras, setting up and position lightings in the scene, positioning and scaling the elements of the heart model into the scene.

Phase Space Transformation and Analysis

As described in U.S. patent application Ser. No. 15/248,838, an analysis system is configured to generate a phase space map to be used in subsequent phase space analysis. The output of the phase space analysis is then evaluated using machine learning analysis to assess parameters associated with a presence of a disease or physiological characteristic such as regional arterial flow characteristics. In some embodiments, the machine learning analysis may use a library of quantified FFR, stenosis, and ischemia data in the assessment of the obtained cardiac gradient signal data.

The output of a processor performing the analysis is then transmitted to a graphical user interface, such as, e.g., a touchscreen or other monitor, for visualization. The graphical user interface, in some embodiments, is included in a display unit configured to display parameters. In some embodiments, the graphical user interface displays intermediate parameters such as a 3D phase space plot representation of the biopotential signal data and virtual biopotential signal data. In other embodiments, the output of the processor is then transmitted to one or more non-graphical user interfaces (e.g., printout, command-line or text-only user interface), directly to a database or memory device for, e.g., later retrieval and/or additional analysis, or combinations thereof.

Figure 23:
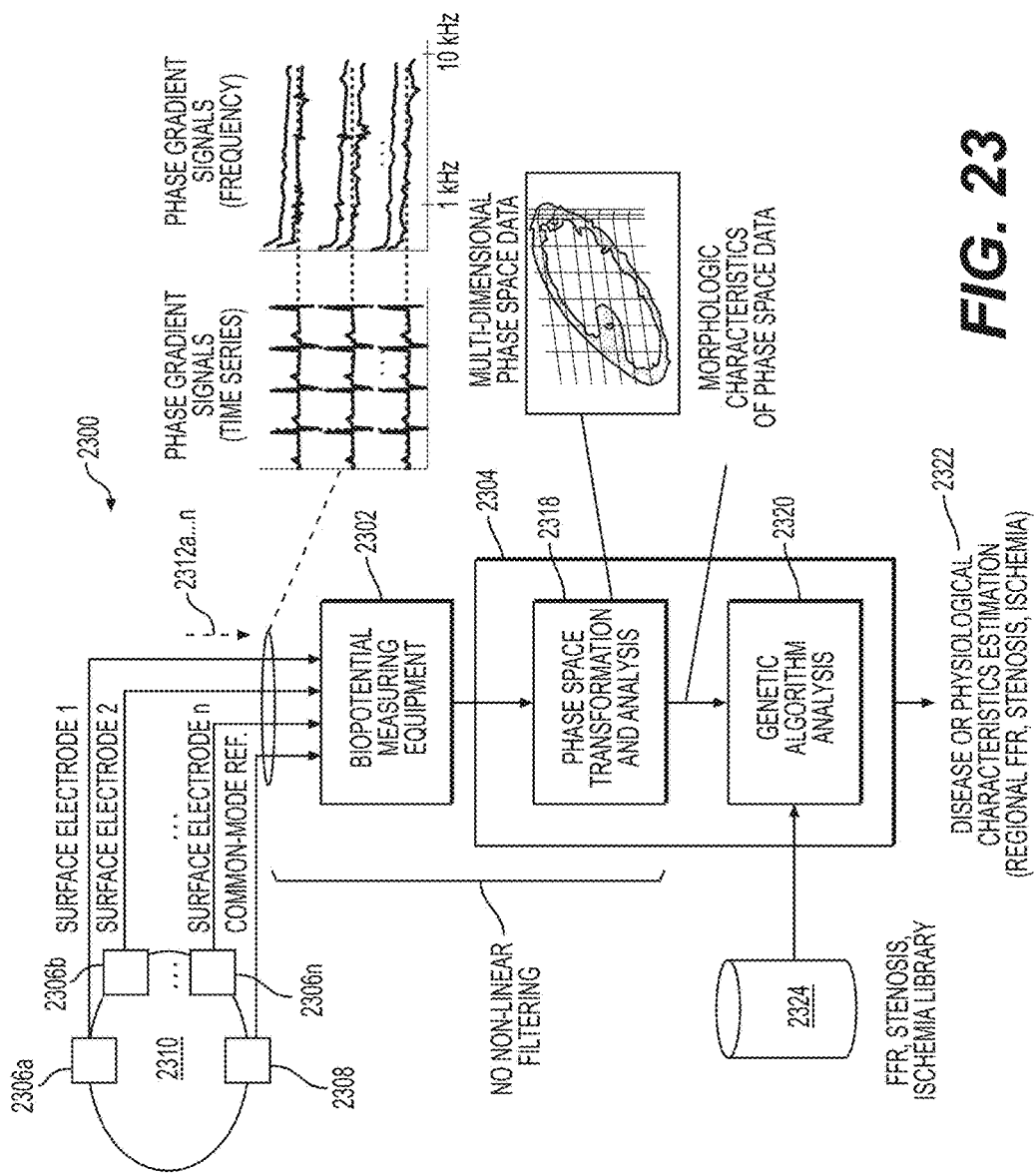
FIG. 23 is a diagram of a system for non-invasively determining arterial flow characteristics in the heart using cardiac gradient data in accordance with an illustrative embodiment.

FIG. 23 is a diagram of an exemplary system 2300 for non-invasively determining arterial flow characteristics in the heart using cardiac gradient data in accordance with an illustrative embodiment. As shown in FIG. 23, the system 2300 includes a biopotential measuring equipment 2302 and an analysis subsystem 2304. The biopotential measuring equipment 2302 collects biopotential signals 2312 (shown as 2312a . . . 2312n) (also referred to herein as cardiac gradient signal data 2312) from a subject or patient 2310, via at least one electrode 2306 (shown as surface electrodes 2306a, 2306b, . . . , 2306n), and corresponding common-mode reference lead 2308, all of which are, in the system of FIG. 23, attached to the surface of the mammalian subject or patient 2310 (e.g., the skin of an animal or a person).

The analysis system 2304 is configured to generate a phase space map to be used in subsequent phase space analysis 2318. The output of the phase space analysis is then evaluated using machine learning analysis 2320 to assess parameters 2322 associated with a presence of a disease or physiological characteristic such as regional arterial flow characteristics. In some embodiments, the machine learning analysis 2320 may use a library 2324 of quantified FFR, stenosis, and ischemia data in the assessment of the obtained cardiac gradient signal data 2312. The output 2322 of a processor performing the analysis 2304 is then transmitted to a graphical user interface, such as, e.g., a touchscreen or other monitor, for visualization. The graphical user interface, in some embodiments, is included in a display unit configured to display parameters 2322. In some embodiments, the graphical user interface displays intermediate parameters such as a 3D phase space plot representation of the biopotential signal data and virtual biopotential signal data. In other embodiments, the output of the processor is then transmitted to one or more non-graphical user interfaces (e.g., printout, command-line or text-only user interface), directly to a database or memory device for, e.g., later retrieval and/or additional analysis, or combinations thereof.

The machine learning process used for developing the predictors takes as its input signals from the PSR device that have been paired with clinical angiography data. In the machine learning operation, the clinical determination of presence or absence of significant CAD is used during the training process and during the verification step. The definition of significant CAD is: >70% blockage and/or FFR<0.8. Other definition of significant CAD can be used.

In some embodiments, a modified Gensini score for each patient is calculated and also used as the input for machine learning. Predictors developed through machine learning aims to manipulate the various features to return a high correlation across the learning sets to the Gensini score. Description of the Gensini scoring is provided in Gensini G. G., "The pathological anatomy of the coronary arteries of man," pp. 271-274 (1975), which is incorporated by reference herein in its entirety. As described, severity score of lesions, from 25% to 100%, processes from a score of 1 to a score of 32 in which each step change in lesion size is twice as large as a prior lesion size in the scoring. Further, a multiplying factor is assigned to each surgical segment or branch of the coronary arteries according to the individual contribution to the perfusion of a given area of myocardium.

In some embodiments, the specific threshold at which a claim that the patient has significant CAD is derived by adjusting the Gensini threshold over the outputs of the predictors to find an optimal balance of sensitivity and specificity exceeding a pre-defined clinical targets (e.g., Sn>75%, Sp>65%). In this way the clinical definitions of CAD (and hence an indication of blockage % or FFR) are incorporated by proxy through the application of the threshold on the predicted Gensini score.

The location of significant lesions is used to train predictors that aim to determine in which artery(ies) significant lesions are present. This training can work in an identical fashion to the calculation of the modified Gensini score and in the threshold determination.

The output imagery provides contextual information on cardiac health, as shown via the graphical user interface 100. The color and shape of the phase space tomographic image synthesizes and displays the electrical and functional status of the heart. The analysis of the physiological signals predicts the presence and location of significant coronary artery disease. The outcome is reported along with a display of the areas of affected myocardium associated with the underlying disease. These visualizations, together with a machine-learned prediction of CAD status are presented in the healthcare provider portal.

As used herein, the term "processor" refers to a physical hardware device that executes encoded instructions for performing functions on inputs and creating outputs. The processor may include one or more processors, each configured to execute instructions and process data to perform one or more functions associated with a computer for indexing images. The processor may be communicatively coupled to RAM, ROM, storage, database, I/O devices, and interface. The processor may be configured to execute sequences of computer program instructions to perform various processes.

In some embodiments, the phase space plot analysis uses geometrical contrast that arises from the interference in the phase plane of the depolarization wave with any other orthogonal leads. The presence of noiseless subspaces allows the recording of the phase of these waves. In general, the amplitude resulting from this interference can be measured; however, the phase of these orthogonal leads still carries the information about the structure and generates geometrical contrast in the image. The phase space plot analysis takes advantage of the fact that different bioelectric structures within, e.g., the heart and its various types of tissue have different impedances, and so spectral and non-spectral conduction delays and bends the trajectory of phase space orbit through the heart by different amounts. These small changes in trajectory can be normalized and quantified beat-to-beat and corrected for abnormal or poor lead placement and the normalized phase space integrals can be visualized on, or mapped to, a geometric mesh using a genetic algorithm to map 17 myocardial segments in the ventricle to various tomographic imaging modalities of the heart from retrospective data. Other number of myocardial segments may be used.

Exemplary Operations to Determine Predictor of Coronary Disease

Table 2 shown as equation of a predictor generated through machine learning on a first bolus of data from a coronary artery disease study conducted with 139 subjects.

TABLE 2

P = dpoly1V(5)^(polyc1Vz(1) + dpoly1V(5)) + (dpolyc3Vz(1) + B1ANTRVENT) residueLevelMeancomplexkickimpulsetensor − noisevectorRz − B1MIDRCA Per the equation of Table 2, if P>threshold, then the patient is determined to have significant coronary artery disease, else the patient is determined not to have significant coronary artery disease. As shown in the embodiment of Table 2, dpoly1V(5), polyc1Vz(1), dpolyc3Vz(1) are geometric parameters derived from the phase space model; and B1ANTRVENT and B1MIDRCA are machine-learned predictors optimized to predict the presence and location of occlusions in specific coronary arteries.

The predicator of Table 2 may be presented in the header region (shown as 140a, 140b) that identifies the presence, or no presence, of significant coronary artery disease being detected (shown as 115a and 115b).

Exemplary Operations to Determine Fractional Flow Reserve Estimates

Tables 3-6 show exemplary embodiment of non-linear functions to generate FFR estimations for several segments corresponding to major vessels in the heart. In Table 3, an exemplary embodiment of a function to determine a FFR estimation for the left main artery ("FFR_LEFTMAIN") is provided.

TABLE 3

FFR_LEFTMAIN = 0.128467341682411*noisevectorRz*atan2(Alpharatio, DensityV4)

As shown in the embodiment of Table 3, the FFR estimation for the left main artery is determined based on extracted metrics and variables such as a Z-component parameter associated with the noise subspace ("noisevectorRz"), a Alphahull ratio parameter ("Alpharatio"), and a signal density cloud volume 4 ("DensityV4").

In Table 4, an exemplary embodiment of a function to determine a FFR estimation for the mid right coronary artery ("FFR MIDRCA") is provided.

TABLE 4

FFR_MIDRCA = 0.0212870065789474*noisevectorRy*Alpharatio*DensityV3

As shown in the embodiment of Table 4, the FFR estimation for the mid right coronary artery is determined based on extracted metrics and variables such as a Y-component parameter associated with the noise subspace 706 ("noisevectorRy"), the Alphahull ratio parameter ("Alpha ratio"), and a signal density cloud volume 3 ("DensityV3").

In Table 5, an exemplary embodiment of a function to determine a FFR estimation for the mid left artery descending artery ("FFR MIDLAD") is provided.

TABLE 5

FFR_MIDLAD = atan2(AspectRatio3, residueLevelMean)

As shown in the embodiment of Table 5, the FFR estimation for the mid left artery descending anterior artery is determined based on extracted metrics and variables such as a ratio of volume to surface area for cloud cluster 3 ("AspectRatio3") and a wavelet residue mean XYZ ("residueLevelMean").

In Table 6, an exemplary embodiment of a function to determine a FFR estimation for the proximal left circumflex artery ("FFR_PROXLCX") is provided.

TABLE 6

FFR_PROXLCX = 0.408884581034257*atan2(residueLevelVolume+ vectorcloud6, DensityV4)

As shown in the embodiment of Table 6, the FFR estimation for the proximal left circumflex artery is determined based on extracted metrics and variables such as a wavelet residue volume XYZ ("residueLevelVolume"), vector cloud 6 volume ("vectorcloud6"), and a signal density cloud volume 4 ("DensityV4").

Further examples and description of the phase space processing that may be used with the exemplified method and system are described in U.S. Provisional Patent Application No. 62/184,796, title "Latent teratogen-induced heart deficits are unmasked postnatally with mathematical analysis and machine learning on ECG signals"; U.S. patent application Ser. No. 15/192,639, title "Methods and Systems Using Mathematical Analysis and Machine Learning to Diagnose Disease"; U.S. patent application Ser. No. 14/620,388, published as US2015/0216426, title "Method and system for characterizing cardiovascular systems from single channel data"; U.S. patent application Ser. No. 14/596,541, issued as U.S. Pat. No. 9,597,021, title "Noninvasive method for estimating glucose, glycosylated hemoglobin and other blood constituents"; U.S. patent application Ser. No. 14/077,993, published as US2015/0133803, title "Noninvasive electrocardiographic method for estimating mammalian cardiac chamber size and mechanical function"; U.S. patent application Ser. No. 14/295,615, title "Noninvasive electrocardiographic method for estimating mammalian cardiac chamber size and mechanical function"; U.S. patent application Ser. No. 13/970,582, issued as U.S. Pat. No. 9,408,543, title "Non-invasive method and system for characterizing cardiovascular systems and all-cause mortality and sudden cardiac death risk"; U.S. patent application Ser. No. 15/061,090, published as US2016/0183822, title "Non-invasive method and system for characterizing cardiovascular systems"; U.S. patent application Ser. No. 13/970,580, issued as U.S. Pat. No. 9,289,150, title "Non-invasive method and system for characterizing cardiovascular systems"; U.S. Patent Application No. 62/354,668, titled "Method and System for Phase Space Analysis to Determine Arterial Flow Characteristics"; and U.S. Provisional Patent Application No. 61/684,217, title "Non-invasive method and system for characterizing cardiovascular systems", which are each incorporated by reference in its entirety.

Exemplary Architecture of Healthcare Provider Portal

Figure 24:
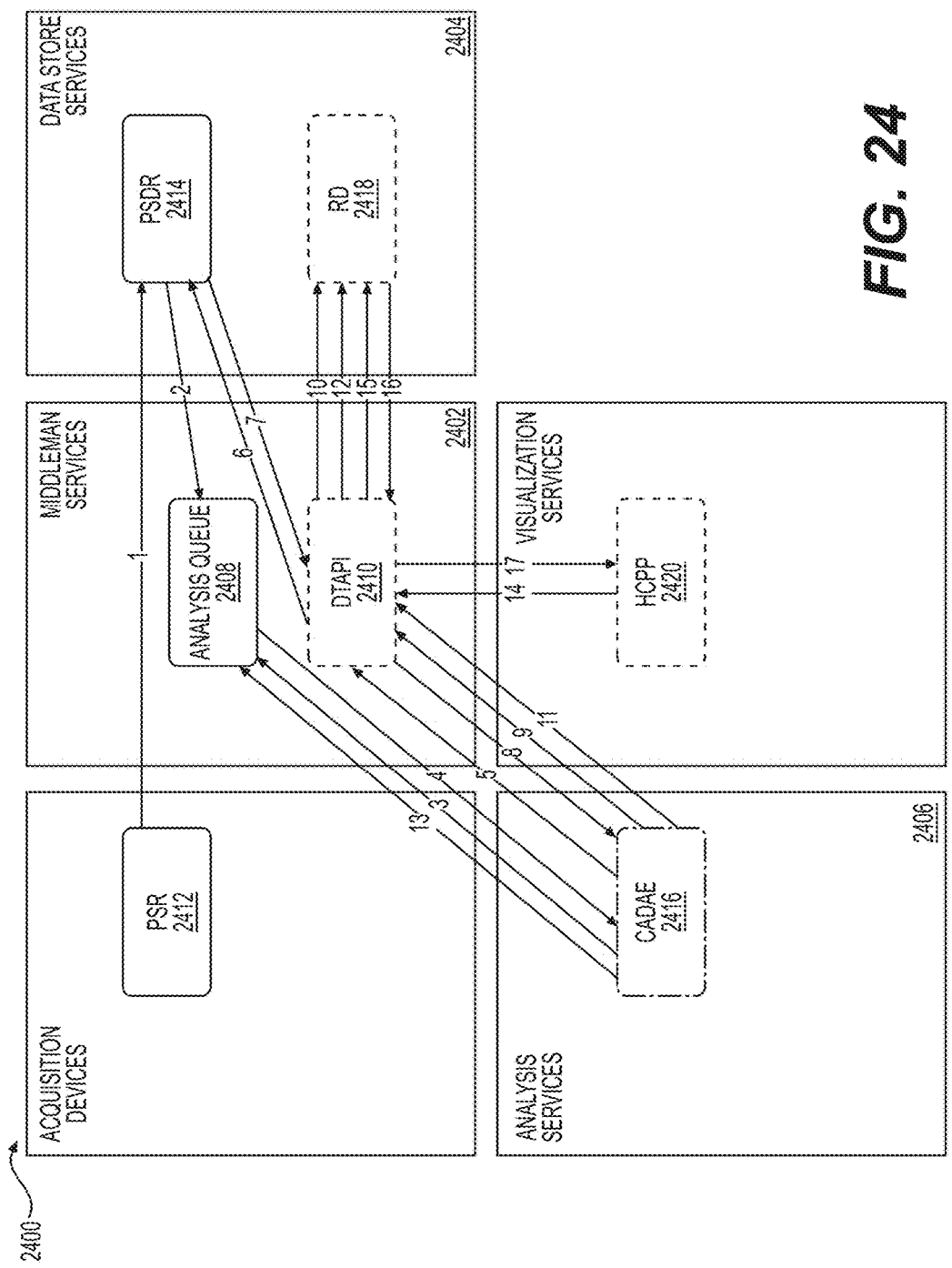
FIG. 24 is a diagram of the architecture of a healthcare provider portal and log database implemented in a cloud service module in accordance with an illustrative embodiment.

FIG. 24 is a diagram 2400 of the architecture of a healthcare provider portal and log database implemented in a cloud service module in accordance with an illustrative embodiment. The cloud services comprise middle-man services 2402, data store services 2404, and analysis services 2406. The middle-man services 2402 comprises an analysis queue 2408 and data transfer APIs ("DTAPI") 2410. The data transfer APIs 2410 is used to fetch signal data files, collected from acquisition devices 2412 (shown as phase space recorder "PSR" 2412), from the data repository 2414 (shown as "PSDR" 2414) to an analytical engine 2416 (shown as "CADAE" 2416) and to store analytical report data generated by the analytical engine 2416 onto a report database 2418 (shown as "RD" 2418). The data transfer APIs 2410 serves as a gateway for major component level data exchanges.

The report database 2418 is a database that stores functional information including a complete traceable set of records for signal acquisition, data accesses and signal analysis. The report database 2418 also stores the analytical reports generated by the analytical engine 2416.

The healthcare provider portal 2420 is a web-based single page application that is accessible by healthcare providers to visualize the output of the analytical engine 2416, e.g., via the graphical user interface 100 generated there-at. A user of the healthcare provider portal 2420 can select a patient, which triggers the healthcare provider portal 2420 to deliver subset or all of the acquired measurement and analysis for that patient. The analysis reports include, in some embodiments, an HTML templated report and interactive 3D objects.

As shown in the embodiment of FIG. 24, upon signal being acquired by the acquisition devices 2412, the data is pushed (shown as step "1") by the acquisition devices 2412 to the data repository 2414. Following the data being stored on the data repository 2414, web services trigger the collected file to be queued (shown as step "2") in the analysis queue 2408 via a simple queuing service (SQS). The analytical engine 2416, on an intermittent basis, send requests (shown as step "3") to de-queue the analysis queue 2408. The simple queuing service dequeues and sends (shown as step "4") the collected data file name and data identifier to the analytical engine 2416. When available to, the analytical engine 2416 generates (shown as step "5") a request to the data transfer APIs 2410 to retrieve the collected file. The data transfer APIs 2410 then communicates (shown as step "6") with the cloud data hosting service to obtain the collected file. The cloud data hosting service sends (shown as step "7") the collected files to the data transfer APIs 2410, which then forwards and/or streams (shown as step "8") the retrieved files to the analytical engine 2416.

The analytical engine 2416 decompresses (shown as step "9") and parses the received files and updates metadata information associated with the files through the data transfer APIs 2410, which parses and send (shown as step "10") the request the update to the data repository 2414.

If the commit succeeds, the analytical engine 2416 proceeds with the analysis and pushes (shown as step "11") the report to the data transfer APIs 2410 upon completion of the analysis. The data transfer APIs 2410 then pushes (shown as step "12") the report to the data repository 2414 to be stored there. The analytical engine 2416 then updates (shown as step "13") the analysis queue 2408 of the updated status for that collected data files.

When ready to be reviewed by the healthcare provider portal 2420, the portal 2420 initiates (shown as step "14") a request to down reports for visualization to the data transfer APIs 2410. The data transfer APIs 2410 queues (shown as step "15") the data repository 2414 to obtain the requested reports. The data repository 2414 retrieves and sends (shown as step "16") the requested reports and corresponding patient information to the data transfer APIs 2410, which then provides (shown as step "17") the data to the healthcare provider portal 2420. The client of the healthcare provider portal 2420, in some embodiments, is a single-threaded process running on a client browser that is running concurrently with a corresponding server processes. The client is responsible for synchronizing the sequence of resource retrieved and trigger updates for updating the renderings.

Figure 25:
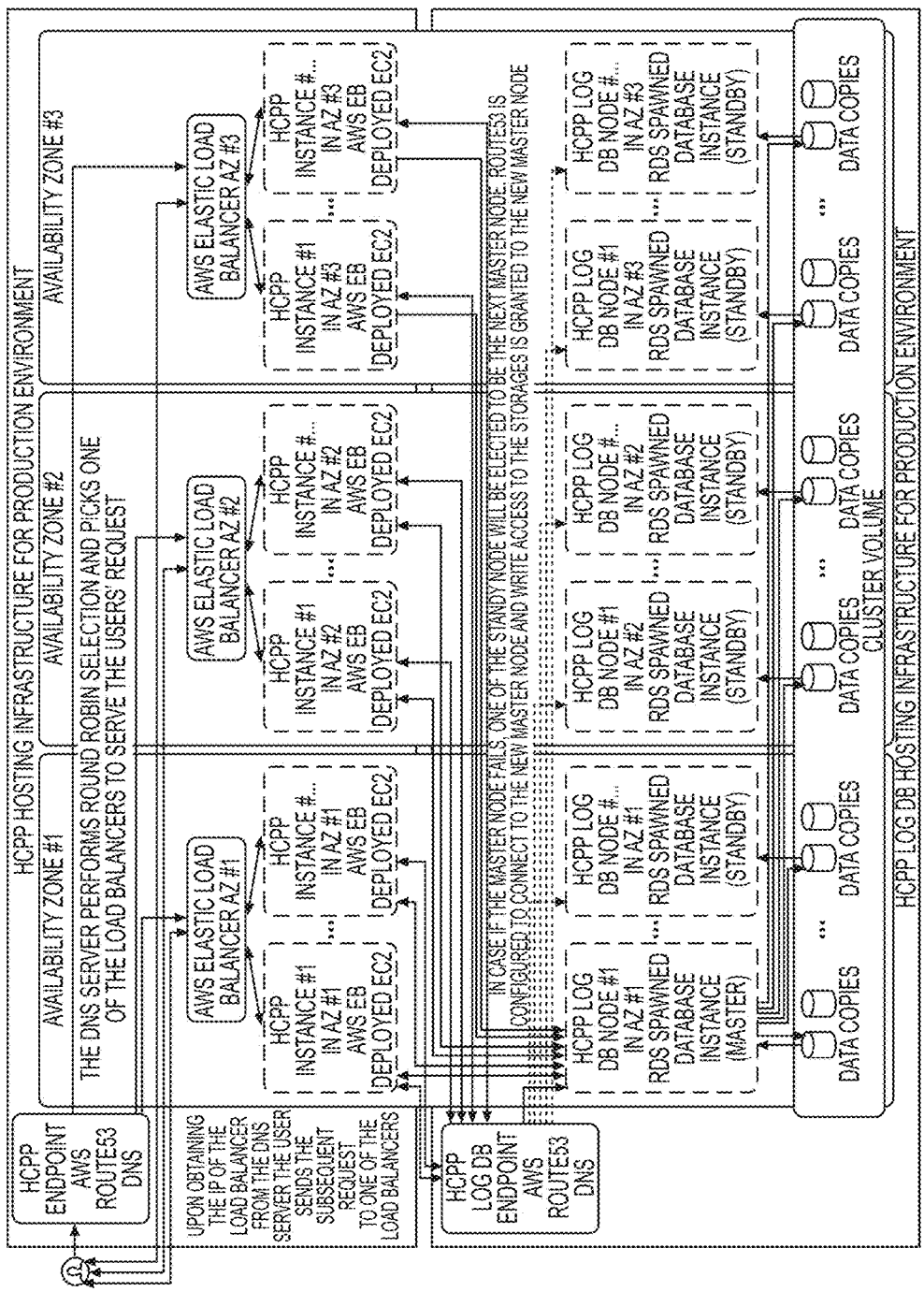
FIG. 25 illustrates an infrastructure layout overview for the healthcare provider portal in accordance with an illustrative embodiment.

FIG. 25 illustrates an infrastructure layout overview for the healthcare provider portal in accordance with an illustrative embodiment. As shown the infrastructure supports a number of instances and availability zones.

While the methods and systems have been described in connection with preferred embodiments and specific examples, it is not intended that the scope be limited to the particular embodiments set forth, as the embodiments herein are intended in all respects to be illustrative rather than restrictive.

The exemplified methods and systems may be used generate stenosis and FFR outputs for use with interventional system configured to use the FFR/stenosis outputs to determine and/or modify a number of stents and their placement intra operation.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

In some embodiments, the signal reconstruction processes is a universal signal decomposition and estimation processing method that is agnostic to a type of sensor/data.

Throughout this application, various publications are referenced. The disclosures of these publications in their entireties are hereby incorporated by reference into this application in order to more fully describe the state of the art to which the methods and systems pertain.

What is claimed is:

1. A computer-implemented method for formatting a display to present summary information and visualizations of myocardial tissue that identifies myocardium at risk and/or coronary arteries that are blocked, the method comprising:

generating, by one or more processors, for a graphical user interface or for a report, a plurality of graphical visualizations including a first graphical visualization and a second graphical visualization, from a data set that identifies myocardium at risk and coronary arteries that are blocked, the data set comprising a plurality of parameters each associated with a corresponding heart segment of a plurality of heart segments, wherein each of the heart segments correspond to an anatomical structure of the heart, wherein the first graphical visualization comprises:
a first graphical element corresponding to a first three-dimensional visualization of myocardial tissue, wherein the first three-dimensional visualization of myocardial tissue comprises a plurality of surface areas each associated with a heart segment of the plurality of heart segments, and
one or more second graphical elements that are overlaid over, or that replaces, a surface area of the plurality of surfaces areas of the first graphical element, the surface area corresponding a given heart segment having a parameter that identifies myocardium at risk, and wherein the second graphical visualization comprises:
a third graphical element corresponding to a first two-dimensional visualization of the plurality of heart segments, the first two-dimensional visualization comprising a plurality of surfaces each corresponding to a segment of the plurality of heart segments, and
one or more fourth graphical elements that are overlaid over, or that replaces, a surface of the plurality of surfaces of the third graphical element, the surface corresponding to the given heart segment having the parameter that identifies the myocardium at risk; and causing, by the one or more processors, the plurality of graphical visualizations to be presented on a display of a computing device or to be stored as a report file.

2. The method of claim 1, comprising:
generating, by the one or more processors, for the graphical user interface or for the report, a third graphical visualization and a fourth graphical visualization of the plurality of graphical visualizations, from a second data set that identifies myocardium at risk and coronary arteries that are blocked, the second data set comprising a second plurality of parameters associated with the plurality of heart segments, wherein the third graphical visualization comprises:
a fifth graphical element corresponding to a second three-dimensional visualization of myocardial tissue, wherein the second three-dimensional visualization of myocardial tissue comprises a second plurality of surface areas associated with the plurality of heart segments, and
one or more sixth graphical elements that are overlaid over, or that replaces, a second surface area of the second plurality of surfaces areas of the fifth graphical element, the second surface area corresponding a given heart segment having a parameter of the second data set that identifies myocardium at risk, and wherein the fourth graphical visualization comprises:
a seventh graphical element corresponding to a second two-dimensional visualization of the plurality of heart segments, the second two-dimensional visualization comprising a second plurality of surfaces corresponding to the plurality of heart segments, and
one or more eight graphical elements that are overlaid over, or that replaces, a second surface of the second plurality of surfaces, the second surface corresponding to the given heart segment having the parameter of the second data that identifies the myocardium at risk; and causing, by the one or more processors, the third graphical visualization and the fourth graphical visualization to be presented on the display of the computing device or to be stored as a part of the report file.

3. The method of claim 1, wherein the first graphical visualization further comprises
a third three-dimensional visualization of myocardial tissue, wherein the third three-dimensional visualization of myocardial tissue is the same as the first three-dimensional visualization,
wherein the first three-dimensional visualization is rendered in accordance with a first viewing perspective, and
wherein the third three-dimensional visualization is rendered in accordance with a second viewing perspective, wherein the first viewing perspective is different from the second viewing perspective.

4. The method of claim 1, wherein the one or more second graphical elements and the one or more fourth graphical elements are selected from the group consisting of a coloration, a surface texture, and an animation.

5. The method of claim 1, wherein the first two-dimensional visualization corresponds to a coronary map comprises a plurality of elongated graphical elements collectively forming a coronary tree, wherein each of the plurality of elongated graphical elements corresponds to a heart segment of the plurality of heart segments.

6. The method of claim 1, wherein the first two-dimensional visualization corresponds to a visualization of a 17-segment map of the myocardial tissue comprising:
a center graphical element;
a first set of graphical elements corresponding to four distinct segments each having a radial area that extends between a first radius value and a second radius value and that collectively surrounds the center graphical element;
a second set of graphical elements corresponding to six distinct segments each having a radial area that extends between the second radius value and a third radius value and that collectively surrounds the first set of graphical elements; and
a third set of graphical elements corresponding to six distinct segments each having a radial area that extends between the third radius value and a fourth radius value and that collectively surrounds the second set of graphical elements.

7. The method of claim 1, wherein the visualization of the 17-segment map comprise one or more fourth set of graphical elements each corresponding to a major artery of the heart, wherein the one or more fourth set of graphical elements are each displayed as a direct projection of the major artery onto a standard heart, each of the one or more fourth set of graphical elements connects portions of the first set of graphical elements, portions of the second set of graphical elements, and/or portions of the third set of graphical elements in a serpentine manner.

8. The method of claim 1,
wherein the first two-dimensional visualization comprises an coronary map comprising a plurality of elongated graphical elements collectively forming a coronary tree, wherein each of the plurality of elongated graphical elements corresponds to a heart segment of the plurality of heart segments; and
wherein the second graphical visualization further comprises a second two-dimensional visualization of a 17-segment map of the myocardial tissue, the second two-dimensional visualization comprising a plurality of surfaces each corresponding to a segment of the plurality of heart segments, and
wherein the second two-dimensional visualization comprises:
a center graphical element;
a first set of graphical elements corresponding to four distinct segments each having a radial area that extends between a first radius value and a second radius value and that collectively surrounds the center graphical element;
a second set of graphical elements corresponding to six distinct segments each having a radial area that extends between the second radius value and a third radius value and that collectively surrounds the first set of graphical elements; and
a third set of graphical elements corresponding to six distinct each having a radial area that extends between the third radius value and a fourth radius value and that collectively surrounds the second set of graphical elements.

9. The method of claim 1, wherein the graphical user interface and the report is caused to be displayed on a stationary or a mobile computing device associated with a client.

10. The method of claim 1, wherein the report is caused to be stored as a non-transitory file.

11. The method of claim 1, wherein the plurality of parameters comprise a predictor of significant coronary disease being present.

12. The method of claim 1, wherein the plurality of parameters comprise a predictor of myocardium of a portion of heart having a pre-defined risk of coronary heart disease.

13. The method of claim 1, wherein the data set is collected and analyzed via phase space tomography analysis.

14. The method of claim 1, wherein the data set is collected from an angiographic study.

15. The method of claim 1, wherein the first three-dimensional visualization of myocardial tissue comprises a standardized rendered 3D model derived from one or more medical scans.

16. The method of claim 1, wherein the first three-dimensional visualization of myocardial tissue comprises a customized rendered 3D model derived from one or more medical scans associated with the patient.

17. The method of claim 1, wherein the first three-dimensional visualization of myocardial tissue comprises an animated rendered 3D model of the heart.

18. A method of claim 1, wherein each of the three-dimensional visualization and the second graphical visualization graphically presents a point of interest in the heart tissue based on the data set.

19. A method of claim 1, comprising:
generating, by one or more processors, contemporaneous with generation of the plurality of graphical visualizations, the report for storage as a file, the report comprising the plurality of graphical visualizations.

20. A method of claim 1, comprising:
generating, by the one or more processors, an audible output, wherein the audible output corresponds to presence of myocardium at risk and/or presence of coronary arteries that are blocked.

21. A system comprising:
a processor; and
a memory having instructions stored thereon, wherein execution of the instructions, cause the processor to:
generate for a graphical user interface or for a report, a plurality of graphical visualizations including a first graphical visualization and a second graphical visualization, from a data set that identifies myocardium at risk and coronary arteries that are blocked, the data set comprising a plurality of parameters each associated with a corresponding heart segment of a plurality of heart segments, wherein each of the heart segments correspond to an anatomical structure of the heart,
wherein the first graphical visualization comprises (i) a first graphical element corresponding to a first three-dimensional visualization of myocardial tissue, wherein the first three-dimensional visualization of myocardial tissue comprises a plurality of surface areas each associated with a heart segment of the plurality of heart segments, and (ii) one or more second graphical elements that are overlaid over, or that replaces, a surface area of the plurality of surfaces areas of the first graphical element, the surface area corresponding a given heart segment having a parameter that identifies myocardium at risk, and
wherein the second graphical visualization comprises (iii) a third graphical element corresponding to a first two-dimensional visualization of the plurality of heart segments, the first two-dimensional visualization comprising a plurality of surfaces each corresponding to a segment of the plurality of heart segments, and (iv) one or more fourth graphical elements that are overlaid over, or that replaces, a surface of the plurality of surfaces of the third graphical element, the surface corresponding to the given heart segment having the parameter that identifies the myocardium at risk; and
cause the plurality of graphical visualizations to be presented on a display of a computing device or to be stored as a report file.

22. A non-transitory computer readable medium having instructions stored thereon, wherein execution of the instructions by a processor, cause the processor to:
generate for a graphical user interface or for a report, a plurality of graphical visualizations including a first graphical visualization and a second graphical visualization, from a data set that identifies myocardium at risk and coronary arteries that are blocked, the data set comprising a plurality of parameters each associated with a corresponding heart segment of a plurality of heart segments, wherein each of the heart segments correspond to an anatomical structure of the heart,
wherein the first graphical visualization comprises (i) a first graphical element corresponding to a first three-dimensional visualization of myocardial tissue, wherein the first three-dimensional visualization of myocardial tissue comprises a plurality of surface areas each associated with a heart segment of the plurality of heart segments, and (ii) one or more second graphical elements that are overlaid over, or that replaces, a surface area of the plurality of surfaces areas of the first graphical element, the surface area corresponding a given heart segment having a parameter that identifies myocardium at risk, and wherein the second graphical visualization comprises (iii) a third graphical element corresponding to a first two-dimensional visualization of the plurality of heart segments, the first two-dimensional visualization comprising a plurality of surfaces each corresponding to a segment of the plurality of heart segments, and (iv) one or more fourth graphical elements that are overlaid over, or that replaces, a surface of the plurality of surfaces of the third graphical element, the surface corresponding to the given heart segment having the parameter that identifies the myocardium at risk; and cause the plurality of graphical visualizations to be presented on a display of a computing device or to be stored as a report file.

\* \* \* \* \*